(12) United States Patent
Kim et al.

(10) Patent No.: US 10,134,997 B2
(45) Date of Patent: *Nov. 20, 2018

(54) INDENOPYRIDINE-BASED COMPOUND AND ORGANIC LIGHT-EMITTING DEVICE INCLUDING THE SAME

(71) Applicants: SAMSUNG DISPLAY CO., LTD., Yongin, Gyeonggi-Do (KR); Sungkyunkwan University Foundation for Corporate Collaboration, Suwon, Gyeonggi-do (KR)

(72) Inventors: Soung-Wook Kim, Yongin (KR); Myeong-Suk Kim, Yongin (KR); Jae-Hong Kim, Yongin (KR); Sam-Il Kho, Yongin (KR); Seung-Soo Yoon, Yongin (KR)

(73) Assignees: Samsung Display Co., Ltd., Yongin, Gyeonggi-do (KR); Sungkyunkwan University Foundation for Corporate Collaboration, Suwon, Gyeonggi-do (KR)

( * ) Notice: Subject to any disclaimer, the term of this patent is extended or adjusted under 35 U.S.C. 154(b) by 223 days.

This patent is subject to a terminal disclaimer.

(21) Appl. No.: 14/457,533

(22) Filed: Aug. 12, 2014

(65) Prior Publication Data

US 2015/0060808 A1 Mar. 5, 2015

(30) Foreign Application Priority Data

Aug. 30, 2013 (KR) ........................ 10-2013-0104502

(51) Int. Cl.
| | | |
|---|---|---|
| *H01L 51/50* | (2006.01) | |
| *H01L 51/00* | (2006.01) | |
| *C07D 221/16* | (2006.01) | |

(52) U.S. Cl.
CPC ........ *H01L 51/0052* (2013.01); *C07D 221/16* (2013.01); *H01L 51/0067* (2013.01);
(Continued)

(58) Field of Classification Search
None
See application file for complete search history.

(56) References Cited

U.S. PATENT DOCUMENTS 6,251,531 B1 * 6/2001 Enokida ................ C07C 211/61
313/504
9,722,191 B2 * 8/2017 Kim .................... H01L 51/0085
(Continued)

FOREIGN PATENT DOCUMENTS

JP         2010114180 A  *  5/2010
KR    10-2009-0098646 A       9/2009
(Continued)

OTHER PUBLICATIONS

Machine English translation of JP 2010-114180 A. Jun. 16, 2016.*

*Primary Examiner* — Jay Yang
(74) *Attorney, Agent, or Firm* — Lee & Morse, P.C.

(57) ABSTRACT

Provided are an indenopyridine-based compound and an organic light-emitting device including the same. The indenopyridine-based compound is represented by Formula 1:

<Formula 1>

19 Claims, 1 Drawing Sheet

(52) U.S. Cl.
 CPC ........ *H01L 51/006* (2013.01); *H01L 51/0054* (2013.01); *H01L 51/5012* (2013.01)

(56) References Cited

U.S. PATENT DOCUMENTS

| | | | |
|---|---|---|---|
| 2004/0197600 A1* | 10/2004 | Thompson | H01L 51/0087 428/690 |
| 2008/0154040 A1* | 6/2008 | Kosuge | C07D 221/16 546/111 |
| 2009/0230857 A1 | 9/2009 | Choi et al. | |
| 2009/0278118 A1* | 11/2009 | Ohrui | C07D 215/04 257/40 |
| 2010/0327270 A1 | 12/2010 | Buesing et al. | |
| 2012/0104379 A1 | 5/2012 | Kawakami et al. | |
| 2014/0131664 A1* | 5/2014 | Yen | C07C 13/62 257/40 |
| 2015/0311450 A1* | 10/2015 | Park | C07D 403/04 257/40 |

FOREIGN PATENT DOCUMENTS

| | | |
|---|---|---|
| KR | 10-2010-0110895 A | 10/2010 |
| KR | 10-2011-0032373 A | 3/2011 |
| KR | 10-2012-0089223 A | 8/2012 |
| WO | WO-2015/053463 A1 * | 4/2015 |

\* cited by examiner

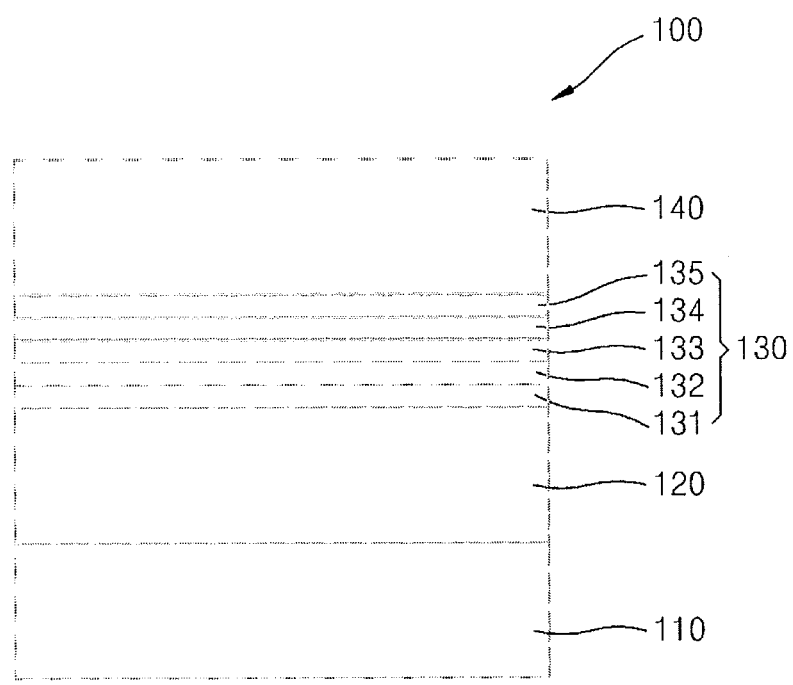

INDENOPYRIDINE-BASED COMPOUND AND ORGANIC LIGHT-EMITTING DEVICE INCLUDING THE SAME

CROSS-REFERENCE TO RELATED APPLICATION

Korean Patent Application No. 10-2013-0104502, filed on Aug. 30, 2013, in the Korean Intellectual Property Office, and entitled: "Indenopyridine-Based Compound and Organic Light-Emitting Device Including The Same," is incorporated by reference herein in its entirety.

BACKGROUND

1. Field

One or more embodiments relate to an indenopyridine-based compound and an organic light-emitting device including the same.

2. Description of the Related Art

Organic light-emitting devices (OLEDs) are self-emitting devices that may have wide viewing angle, excellent contrast, quick response, high brightness, and excellent driving voltage, and can provide multicolored images.

SUMMARY

Embodiments are directed to an indenopyridine-based compound represented by Formula 1:

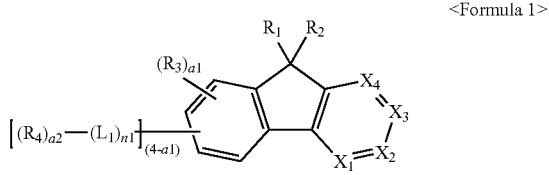

<Formula 1> wherein, in Formula 1, $X_1$ is a nitrogen atom (N) or $C(R_{11})$; $X_2$ is N or $C(R_{12})$; $X_3$ is N or $C(R_{13})$; $X_4$ is N or $C(R_{14})$; wherein at least one of $X_1$ to $X_4$ is N;

$L_1$ is selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, a substituted or unsubstituted $C_2$-$C_{10}$ heterocycloalkylene group, a substituted or unsubstituted $C_2$-$C_{10}$ heterocycloalkenylene group, and a substituted or unsubstituted $C_2$-$C_{60}$ heteroarylene group;

n1 is selected from an integer of 0, 1, 2, and 3;

$R_1$ and $R_2$ are each independently selected from a hydrogen atom, a deuterium atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, and a substituted or unsubstituted $C_2$-$C_{30}$ heteroaryl group, wherein $R_1$ and $R_2$ are optionally connected to each other to form a substituted or unsubstituted $C_6$-$C_{20}$ saturated ring or a substituted or unsubstituted $C_6$-$C_{20}$ unsaturated ring;

$R_{11}$ to $R_{14}$, $R_3$, and $R_4$ are each independently selected from a hydrogen atom, a deuterium atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, and a substituted or unsubstituted $C_2$-$C_{30}$ heteroaryl group; and a1 and a2 are each independently selected from an integer of 0, 1, 2 and 3.

Also provided is an organic light-emitting device (OLED), including a first electrode; a second electrode facing the first electrode; and an organic layer that is disposed between the first electrode and the second electrode and includes an emission layer. The organic layer includes at least one indenopyridine-based compound represented by Formula 1.

BRIEF DESCRIPTION OF THE DRAWINGS

Features will become apparent to those of skill in the art by describing in detail exemplary embodiments with reference to the attached drawings in which:

FIG. 1 illustrates a schematic diagram illustrating an organic light-emitting device (OLED) according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. As used herein, the term "and/or" includes any and all combinations of one or more of the associated listed items. Expressions such as "at least one of," when preceding a list of elements, modify the entire list of elements and do not modify the individual elements of the list.

Provided is an indenopyridine-based compound represented by Formula 1:

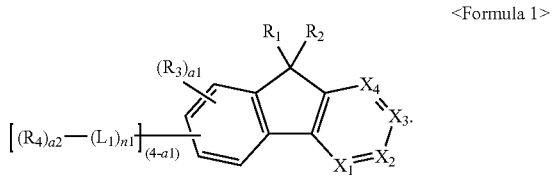

<Formula 1>

In Formula 1, $X_1$ is N or $C(R_{11})$; $X_2$ is N or $C(R_{12})$; $X_3$ is N or $C(R_{13})$; $X_4$ is N or $C(R_{14})$; wherein at least one of $X_1$ to $X_4$ may be N.

In one embodiment, in Formula 1, $X_1$ may be N; $X_2$ may be $C(R_{12})$; $X_3$ may be $C(R_{13})$; and $X_4$ may be $C(R_{14})$.

In another embodiment, in Formula 1, $X_1$ may be $C(R_{11})$; $X_2$ may be N; $X_3$ may be $C(R_{13})$; and $X_4$ may be $C(R_{14})$.

In another embodiment, in Formula 1, $X_1$ may be $C(R_{11})$; $X_2$ may be $C(R_{12})$; $X_3$ may be N; and $X_4$ may be $C(R_{14})$.

In another embodiment, in Formula 1, $X_1$ may be $C(R_{11})$; $X_2$ may be $C(R_{12})$; $X_3$ may be $C(R_{13})$; and $X_4$ may be N.

In Formula 1, $L_1$ may be selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, a substituted or unsubstituted $C_2$-$C_{10}$ heterocycloalkylene group, a substituted or unsubstituted $C_2$-$C_{10}$ heterocycloalkenylene group, and a substituted or unsubstituted $C_2$-$C_{60}$ heteroarylene group.

In one embodiment, in Formula 1, $L_1$ may be selected from:

i) a $C_3$-$C_{10}$ cycloalkylene group, a $C_3$-$C_{10}$ cycloalkenylene group, a $C_6$-$C_{60}$ arylene group, a $C_2$-$C_{10}$ heterocycloalkylene group, a $C_2$-$C_{10}$ heterocycloalkenylene group, and a $C_2$-$C_{60}$ heteroarylene group; and ii) a $C_3$-$C_{10}$ cycloalkylene group, a $C_3$-$C_{10}$ cycloalkenylene group, a $C_6$-$C_{60}$ arylene group, a $C_2$-$C_{10}$ heterocycloalkylene group, a $C_2$-$C_{10}$ heterocycloalkenylene group, and a $C_2$-$C_{60}$ heteroarylene group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, and a $C_1$-$C_{10}$ alkyl group;

a $C_1$-$C_{10}$ alkyl group substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, and a phosphoric acid group or a salt thereof;

a $C_6$-$C_{16}$ aryl group and a $C_2$-$C_{16}$ heteroaryl group; and a $C_6$-$C_{16}$ aryl group and a $C_2$-$C_{16}$ heteroaryl group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{16}$ aryl group, and a $C_2$-$C_{16}$ heteroaryl group.

In another embodiment, in Formula 1, L1 may be selected from:

i) a phenylene group, a pentalenylene group, an indenylene group, a naphthylene group, an azulenylene group, a heptalenylene group, an indacenylene group, an acenaphtylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isooxazolylene group, an oxazolylene group, a triazolylene group, a tetrazolylene group, an oxzdiazolylene group, a triazinylene group, a benzooxazolylene group, a dibenzofuranylene group, a dibenzothiophenylene group, and a benzocarbazolyl group; and ii) a phenylene group, a pentalenylene group, an indenylene group, a naphthylene group, an azulenylene group, a heptalenylene group, an indacenylene group, an acenaphtylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isooxazolylene group, an oxazolylene group, a triazolylene group, a tetrazolylene group, an oxzdiazolylene group, a triazinylene group, a benzooxazolylene group, a dibenzofuranylene group, a dibenzothiophenylene group, and a benzocarbazolyl group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, and a $C_1$-$C_{10}$ alkyl group;

a $C_1$-$C_{10}$ alkyl group substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, and a phosphoric acid group or a salt thereof;

a $C_6$-$C_{16}$ aryl group and a $C_2$-$C_{16}$ heteroaryl group; and a $C_6$-$C_{16}$ aryl group and a $C_2$-$C_{16}$ heteroaryl group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{16}$ aryl group, and a $C_2$-$C_{16}$ heteroaryl group.

In another embodiment, in Formula 1, L1 may be selected from:

i) a phenylene group, a naphthylene group, an anthracenylene group, a chrysenylene group, and a pyrenylene group; and ii) a phenylene group, a naphthylene group, an anthracenylene group, a chrysenylene group, and a pyrenylene group, each substituted with at least one selected from
a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, and a $C_1$-$C_{10}$ alkyl group;

a $C_1$-$C_{10}$ alkyl group substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, and a phosphoric acid group or a salt thereof;

a $C_6$-$C_{16}$ aryl group and a $C_2$-$C_{16}$ heteroaryl group; and a $C_6$-$C_{16}$ aryl group and a $C_2$-$C_{16}$ heteroaryl group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{16}$ aryl group, and a $C_2$-$C_{16}$ heteroaryl group.

In another embodiment, in Formula 1, L1 may be selected from:

i) a phenylene group, an anthracenylene group, a chrysenylene group, and a pyrenylene group; and ii) a phenylene group, an anthracenylene group, a chrysenylene group, and a pyrenylene group, each substituted with at least one selected from
a deuterium atom, a halogen atom, a hydroxyl group, a cyano group, a nitro group, a methyl group, an ethyl group, an n-propyl group, an iso-propyl group, an n-butyl group, a sec-butyl group, an iso-butyl group, and a tert-butyl group;

a phenyl group, a naphthyl group, a pyridyl group, and a triazinyl group; and a phenyl group, a naphthyl group, a pyridyl group, and a triazinyl group, each substituted with at least one selected from a deuterium atom, a halogen atom, a hydroxyl group, a cyano group, a nitro group, a methyl group, an ethyl group, an n-propyl group, an iso-propyl group, an n-butyl group, a sec-butyl group, an iso-butyl group, and a tert-butyl group.

In another embodiment, in Formula 1, L1 may be selected from a phenylene group, an anthracenylene group, a chrysenylene group, and a pyrenylene group.

In Formula 1, n1 denotes the number of L1, and n1 is an integer of 0 to 3. When n1 is an integer of 2 or greater, L1 s may be identical to or different from each other.

In some embodiments, in Formula 1, n1 may be an integer of 1 or 2.

In one embodiments, in Formula 1, a moiety represented by $(L_1)_{n1}$ may be one selected from Formulae 2-1 to 2-4:

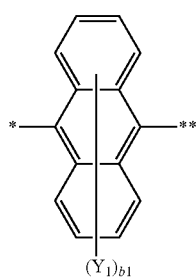

2″1

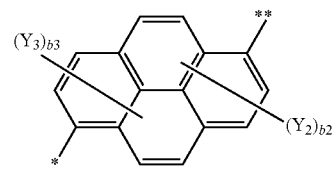

2″2

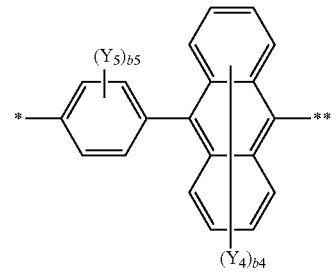

2″3

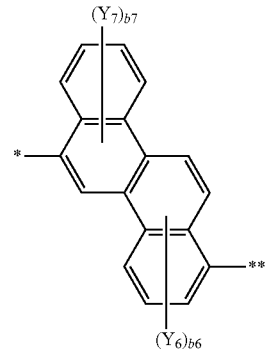

2″4

In Formulae 2-1 to 2-4, $Y_1$ to $Y_7$ are each independently selected from i) a hydrogen atom, a deuterium atom, a halogen atom, a hydroxyl group, a cyano group, a nitro group, a methyl group, an ethyl group, an n-propyl group, an iso-propyl group, an n-butyl group, a sec-butyl group, an iso-butyl group, and a tert-butyl group;

ii) a phenyl group, a naphthyl group, a pyridyl group, and a triazinyl group; and iii) a phenyl group, a naphthyl group, a pyridyl group, and a triazinyl group, each substituted with at least one selected from a deuterium atom, a halogen atom, a hydroxyl group, a cyano group, a nitro group, a methyl group, an ethyl group, an n-propyl group, an iso-propyl group, an n-butyl group, a sec-butyl group, an iso-butyl group, and a tert-butyl group;

b1 to b7 are each independently an integer of 0 to 4;

* is a binding site with $R_4$; and

** is a binding site with an indenopyridine ring.

In another embodiment, in Formula 1, a moiety represented by $(L_1)_{n1}$ may be one selected from Formulae 2-1 to 2-4:

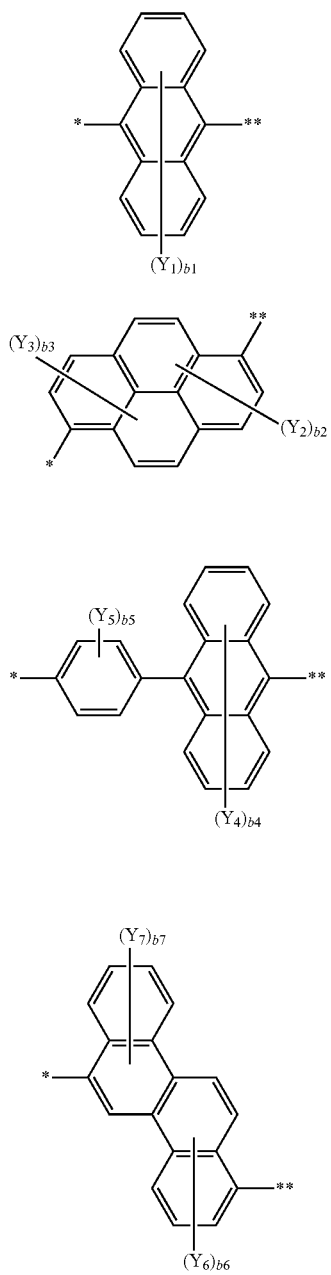

In Formulae 2-1 to 2-4,

Y$_1$ to Y$_7$ are each independently selected from a hydrogen atom, a deuterium atom, a fluorine atom, a hydroxyl group, a cyano group, a nitro group, a methyl group, an ethyl group, an n-propyl group, an iso-propyl group, a tert-butyl group, a phenyl group, a naphthyl group, a pyridyl group, and a triazinyl group;

b1 to b7 are each independently an integer of 0 or 1;

* is a binding site with R$_4$; and

** is a binding site with an indenopyridine ring.

In another embodiment, in Formula 1, a moiety represented by (L$_1$)$_{n1}$ may be one selected from Formulae 3-1 to 3-4:

In Formulae 3-1 to 3-4,

* is a binding site with R$_4$; and

** is a binding site with an indenopyridine ring.

In Formula 1, R$_1$ and R$_2$ may each independently be selected from a hydrogen atom, a deuterium atom, a halogen atom, a hydroxyl group, a cyano group, a nitro group, an amino group, a carboxyl group, a substituted or unsubstituted C$_1$-C$_{30}$ alkyl group, a substituted or unsubstituted C$_2$-C$_{30}$ alkenyl group, a substituted or unsubstituted C$_2$-C$_{30}$ alkynyl group, a substituted or unsubstituted C$_1$-C$_{30}$ alkoxy group, a substituted or unsubstituted C$_3$-C$_{30}$ cycloalkyl group, a substituted or unsubstituted C$_3$-C$_{30}$ cycloalkenyl group, a substituted or unsubstituted C$_6$-C$_{30}$ aryl group, a substituted or unsubstituted C$_6$-C$_{30}$ aryloxy group, a substituted or unsubstituted C$_6$-C$_{30}$ arylthio group, and a substituted or unsubstituted C$_2$-C$_{30}$ heteroaryl group, wherein R$_1$ and R$_2$ may be optionally linked to each other and form a substituted or unsubstituted C$_6$-C$_{20}$ saturated ring or a substituted or unsubstituted C$_6$-C$_{20}$ unsaturated ring.

In one embodiment, in Formula 1, R$_1$ and R$_2$ are each independently selected from a hydrogen atom, a deuterium atom, a halogen atom, a hydroxyl group, a cyano group, a nitro group, a substituted or unsubstituted C$_1$-C$_{10}$ alkyl group, and a substituted or unsubstituted C$_6$-C$_{16}$ aryl group, wherein R$_1$ and R$_2$ may be optionally linked to each other and form a substituted or unsubstituted C$_6$-C$_{20}$ saturated ring or a substituted or unsubstituted C$_6$-C$_{20}$ unsaturated ring.

In another embodiment, in Formula 1, $R_1$ and $R_2$ are each independently selected from a hydrogen atom, a deuterium atom, a fluorine atom, a hydroxyl group, a cyano group, a nitro group, a methyl group, an ethyl group, an n-propyl group, an iso-propyl group, a tert-butyl group, a phenyl group, and a naphthyl group, wherein $R_1$ and $R_2$ may be optionally linked to each other and form an unsubstituted $C_6$-$C_{20}$ saturated ring or an unsubstituted $C_6$-$C_{20}$ unsaturated ring.

In another embodiment, in Formula 1, $R_1$ and $R_2$ may each independently be selected from a hydrogen atom, a deuterium atom, a methyl group, and a phenyl group, or $R_1$ and $R_2$ combined are Formula 5:

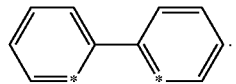

<Formula 5>

In Formula 5, * is a binding site with an indenopyridine ring.

In Formula 1, $R_{11}$ to $R_{14}$, $R_3$, and $R_4$ may each independently be selected from a hydrogen atom, a deuterium atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, and a substituted or unsubstituted $C_2$-$C_{30}$ heteroaryl group.

In one embodiment, in Formula 1, $R_{11}$ to $R_{14}$ and $R_3$ may each independently be selected from i) a hydrogen atom, a deuterium atom, a halogen atom, a hydroxyl group, a cyano group, a nitro group, a methyl group, an ethyl group, an n-propyl group, an iso-propyl group, an n-butyl group, a sec-butyl group, an iso-butyl group, and a tert-butyl group;

ii) a phenyl group, a naphthyl group, a pyridyl group, and a triazinyl group; and iii) a phenyl group, a naphthyl group, a pyridyl group, and a triazinyl group, each substituted with at least one selected from a deuterium atom, a halogen atom, a hydroxyl group, a cyano group, a nitro group, a methyl group, an ethyl group, an n-propyl group, an iso-propyl group, an n-butyl group, a sec-butyl group, an iso-butyl group, and a tert-butyl group.

In another embodiment, in Formula 1, $R_{11}$ to $R_{14}$ and $R_3$ may each independently be selected from a hydrogen atom, a deuterium atom, a fluorine atom, a cyano group, a nitro group, a methyl group, an ethyl group, an n-propyl group, an iso-propyl group, an n-butyl group, a sec-butyl group, and an iso-butyl group.

In another embodiment, in Formula 1, $R_{11}$ to $R_{14}$ and $R_3$ may each independently be selected from a hydrogen atom, a deuterium atom, a fluorine atom, a cyano group, a nitro group, a methyl group, and a tert-butyl group.

In one embodiment, in Formula 1, $R_4$ may be selected from a substituted or unsubstituted $C_6$-$C_{20}$ aryl group, and a substituted or unsubstituted $C_2$-$C_{20}$ heteroaryl group.

In another embodiment, in Formula 1, $R_4$ may be selected from:

i) a $C_6$-$C_{20}$ aryl group and a $C_2$-$C_{20}$ heteroaryl group; and ii) a $C_6$-$C_{20}$ aryl group and a $C_2$-$C_{20}$ heteroaryl group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, and a $C_1$-$C_{10}$ alkyl group;

a $C_1$-$C_{10}$ alkyl group substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, and a phosphoric acid group or a salt thereof;

a $C_6$-$C_{16}$ aryl group and a $C_2$-$C_{16}$ heteroaryl group; and a $C_6$-$C_{16}$ aryl group and a $C_2$-$C_{16}$ heteroaryl group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{16}$ aryl group, and a $C_2$-$C_{16}$ heteroaryl group.

In another embodiment, in Formula 1, $R_4$ may be selected from:

i) a phenyl group, a pentalenyl group, a naphthyl group, an azulenyl group, a heptalenyl group, an indacenyl group, an acenaphtyl group, a fluorenyl group, a spiro-fluorenyl group, a phenalenyl group, a phenathrenyl group, an anthryl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzooxazolyl group, a dibenzopuranyl group, a dibenzothiophenyl group, and a carbazolyl group; and ii) a phenyl group, a pentalenyl group, a naphthyl group, an azulenyl group, a heptalenyl group, an indacenyl group, an acenaphtyl group, fluolenyl group, a spiro-fluorenyl group, a phenalenyl group, a phenathrenyl group, an anthryl group, fluoranthenyl group, a triphenylenyl group, a pyrenyl group, a chrysenyl group, a naphthacenyl group. a picenyl group, a perylenyl group, a pentaphenyl group, a hexacenyl group, a pyrrolyl group, an imidazolyl group, a pyrazolyl group, a pyridyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzooxazolyl group, a dibenzopuranyl group, a dibenzothiophenyl group, and a carbazolyl group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, and a $C_1$-$C_{10}$ alkyl group;

a $C_1$-$C_{10}$ alkyl group substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, and a phosphoric acid group or a salt thereof;

a $C_6$-$C_{16}$ aryl group and a $C_2$-$C_{16}$ heteroaryl group; and a $C_6$-$C_{16}$ aryl group and a $C_2$-$C_{16}$ heteroaryl group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{16}$ aryl group, and a $C_2$-$C_{16}$ heteroaryl group.

In another embodiment, in Formula 1, $R_4$ may be selected from:

i) a phenyl group, a naphthyl group, and an anthryl group; and ii) a phenyl group, a naphthyl group, and an anthryl group, each substituted with at least one selected from a hydrogen atom, a deuterium atom, a halogen atom, a hydroxyl group, a cyano group, a nitro group, a methyl group, an ethyl group, an n-propyl group, an iso-propyl group, a tert-butyl group, a phenyl group, a naphthyl group, and an anthryl group.

In another embodiment, in Formula 1, $R_4$ may be selected from a phenyl group, 1-a naphthyl group, and 2-a naphthyl group.

In Formula 1, a1 is the number of R3 which may be an integer of 0 to 3. When a1 is an integer of 2 or greater, R3s may be identical to or different from each other.

In Formula 1, a2 is the number of R4 which may be an integer of 0 to 3. When a2 is an integer of 2 or greater, R4s may be identical to or different from each other.

In some embodiments, in Formula 1, a1 may be an integer of 0 or 1.

In some embodiments, in Formula 1, a2 may be an integer of 0 or 1.

In Formula 1, the number of moiety represented by $[(R_4)_{a2}$-$(L_1)_{n1}]$ may be represented by (4-a1).

In one embodiment, a1 may be an integer of 2 or 3.

In another embodiment, a2 may be 1 or n1 may be 1, and a1 may be 3.

In one embodiment, the indenopyridine-based compound may be represented by Formula 1a:

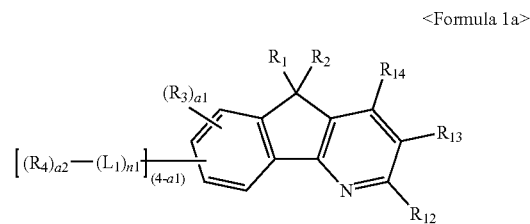

<Formula 1a> wherein, in Formula 1a, a moiety represented by $(L_1)_{n1}$ may be one selected from Formulae 3-1 to 3-4:

3"1

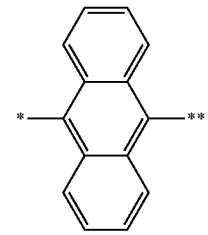

3"2

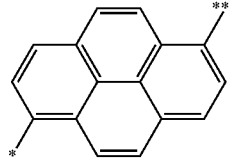

3"3

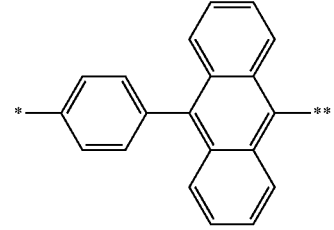

3"4

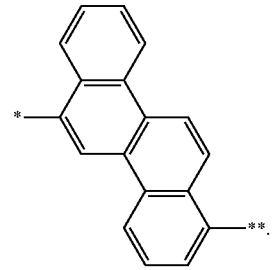

wherein, in Formulae 3-1 to 3-4,
* is a binding site with $R_4$; ** is a binding site with an indenopyridine ring; and
$R_1$ and $R_2$ are each independently selected from a hydrogen atom, a deuterium atom, a methyl group, and a phenyl group, or $R_1$ and $R_2$ combined are Formula 5:

<Formula 5>

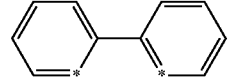

wherein, in Formula 5,

* is a binding site with an indenopyridine ring;

$R_3$ and $R_{12}$ to $R_{14}$ are each independently selected from a hydrogen atom, a deuterium atom, a fluorine atom, a cyano group, a nitro group, and a methyl group;

$R_4$ is selected from a phenyl group, a 1-naphthyl group, and a 2-naphthyl group;

a1 is 3; and a2 is an integer of 0 or 1.

In another embodiment, the indenopyridine-based compound may be represented by one selected from Formulae 1b to 1e:

<Formula 1b>

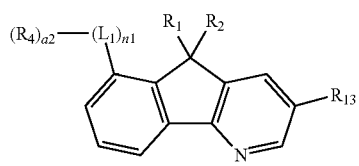

<Formula 1c>

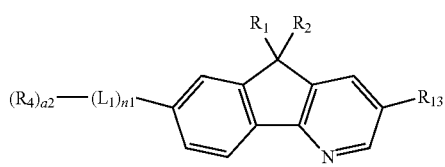

<Formula 1d>

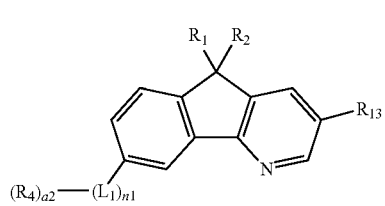

<Formula 1e>

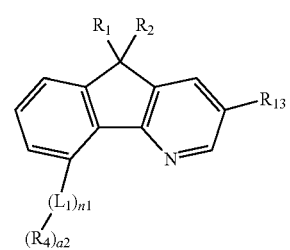

wherein, in Formulae 1b to 1e, a moiety represented by $(L_1)_{n1}$ is one selected from Formulae 3-1 to 3-4:

3-1

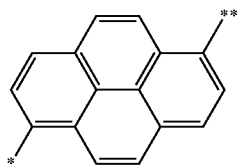

3-2

3-3

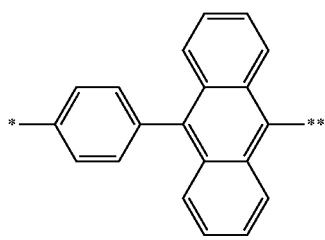

3-4

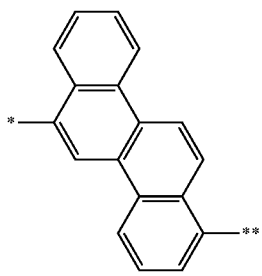

wherein, in Formulae 3-1 to 3-4,

* is a binding site with $R_4$; ** is a binding site with an indenopyridine ring; and $R_1$ and $R_2$ are each independently selected from a hydrogen atom, a deuterium atom, a methyl group, and a phenyl group, or $R_1$ and $R_2$ combined are Formula 5:

<Formula 5>

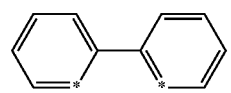

wherein, in Formula 5,

* is a binding site with an indenopyridine ring;

$R_{13}$ is selected from a hydrogen atom, a deuterium atom, a fluorine atom, a cyano group, a nitro group, and a methyl group;

$R_4$ is selected from a phenyl group, a 1-naphthyl group, and a 2-naphthyl group; and a2 is an integer of 0 or 1.

In some embodiments, the indenopyridine-based compound may be selected from Compounds 1 to 25:

1

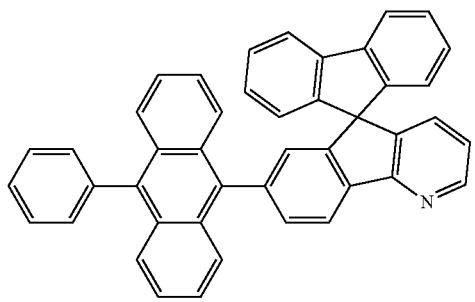

2
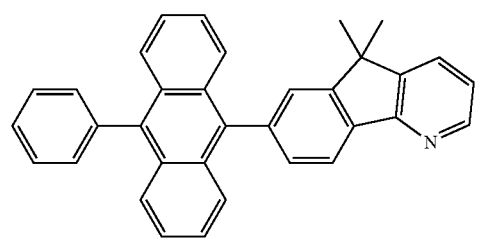
3
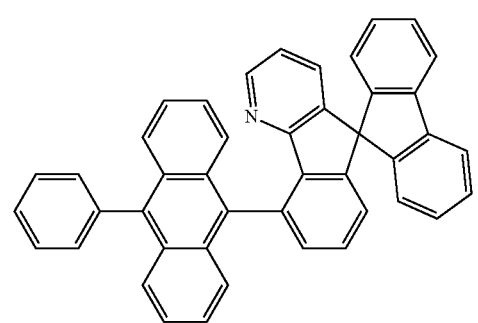
4
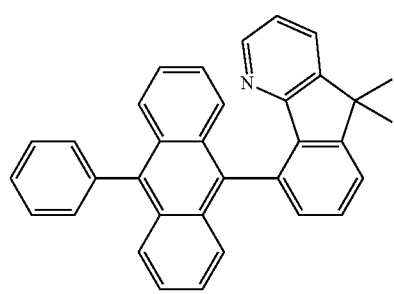
5
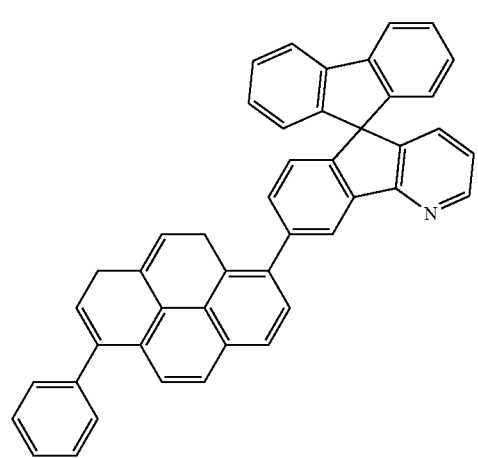
6
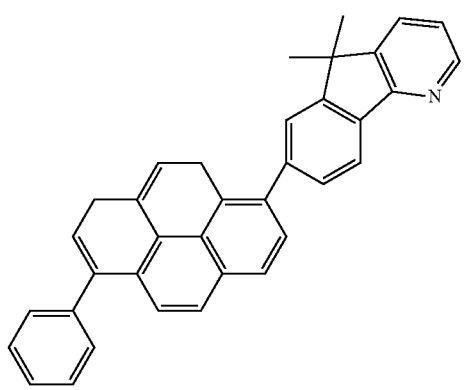
7
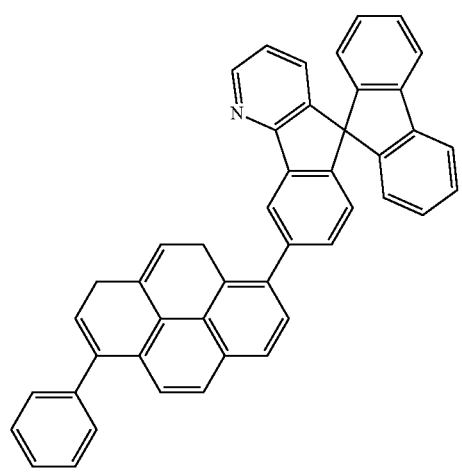
8
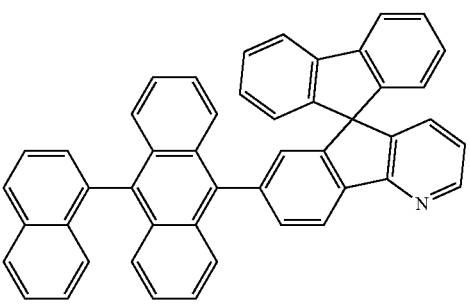
9
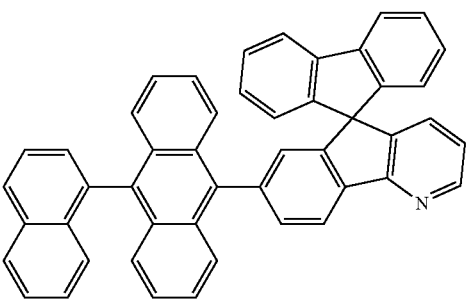

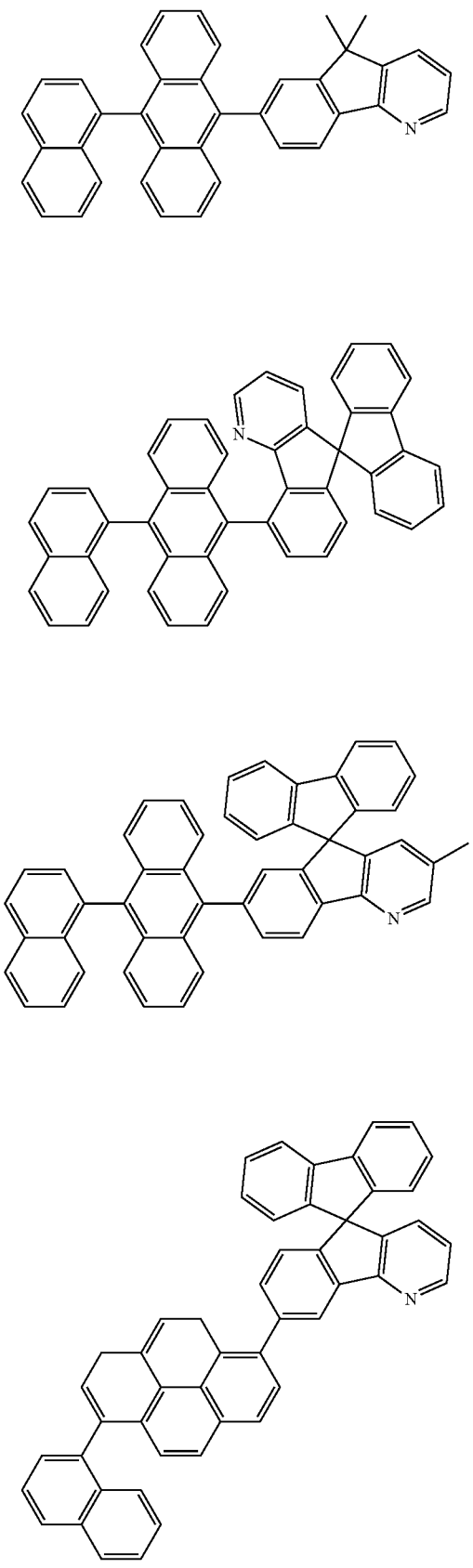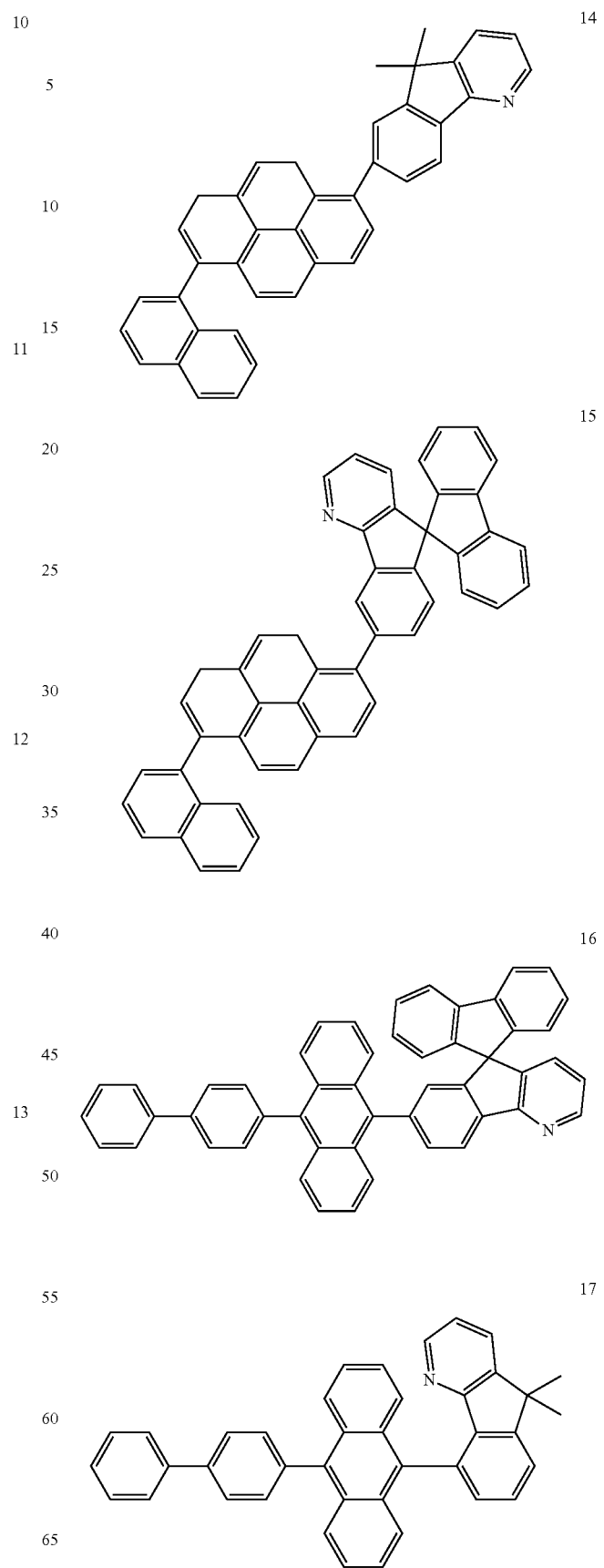

-continued

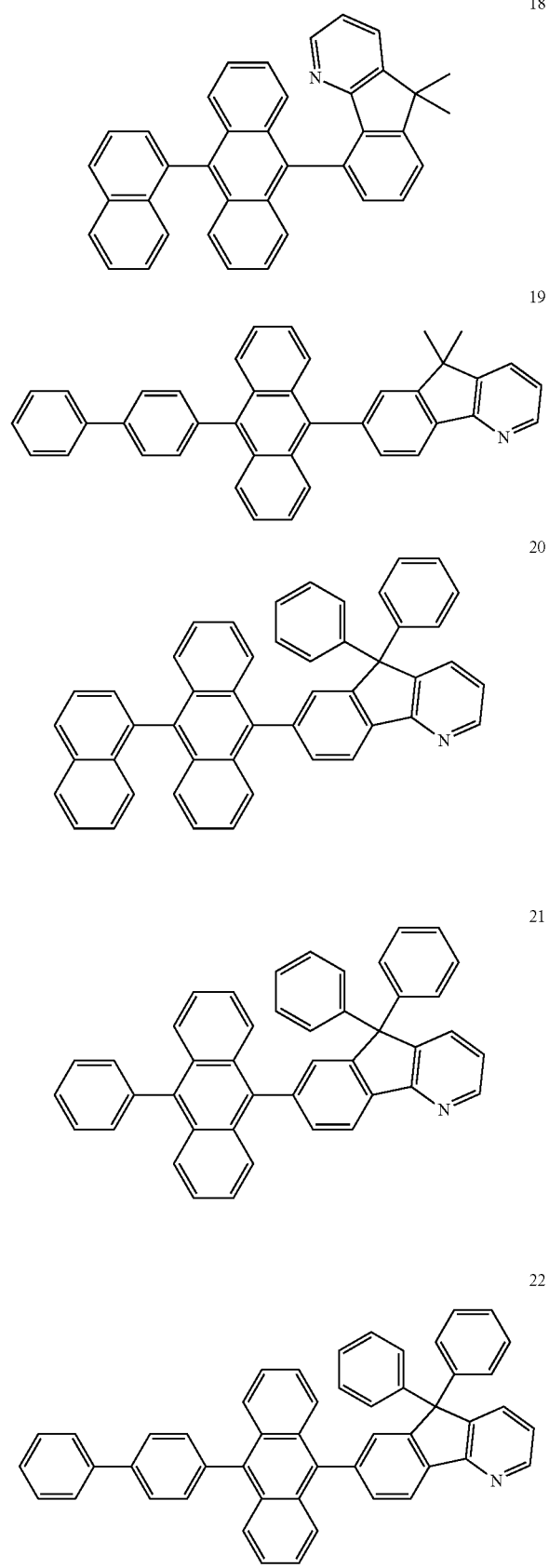

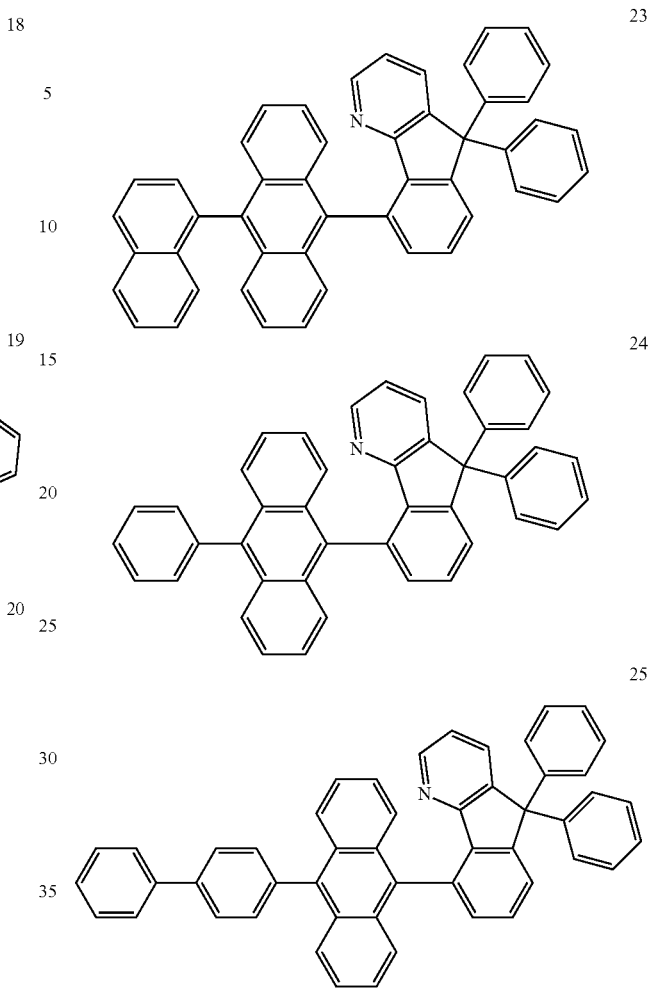

An indenopyridine-based compound represented by Formula 1 may have a high glass transition temperature (Tg) and excellent thermal stability, and an OLED including an indenopyridine-based compound represented by Formula 1 may have a thin film that exhibits high stability.

An indenopyridine-based compound represented by Formula 1 may increase a formation ratio of excitons by increasing a trapping ratio of holes and electrons in an OLED. Also, an indenopyridine-based compound represented by Formula 1 may have a relatively high resistance against a charge exposure, and an OLED including an indenopyridine-based compound represented by Formula 1 may have an improved efficiency and an improved lifespan.

An indenopyridine-based compound represented by Formula 1 may have a band gap that is narrower than that of a carbazole-based compound, and may help provide improved emission of fluorescent light compared to a carbazole-based compound. In addition, the indenopyridine-based compound may have excellent hole transporting properties, and the indenopyridine-based compound may help provide an OLED with an improved efficiency compared to a carbazole-based compound, which may hinder control of charge balance in an emission layer.

Also, an indenopyridine-based compound represented by Formula 1 may have a higher amorphous degree than a compound including pyridine, and the indenopyridine-based compound may produce excitons with better efficiency in an emission layer. An organic-light emitting device including the indenopyridine-based compound may have a relatively high efficiency.

Moreover, an indenopyridine-based represented by Formula 1 includes a nitrogen atom (N) in an indenopyridine ring, and charges may be easily trapped in the indenopyridine-based compound. Therefore, when the indenopyridine-based compound serves as a host, a large amount of charges trapped in the host may be transported to a dopant, and efficiency of the OLED may increase.

An indenopyridine-based compound represented by Formula 1 may be synthesized by using an organic synthesis method. The synthesis method of the indenopyridine-based compound may be easily understood by one of skill in the art with reference to examples, which will be described below.

As used herein, the expression "organic layer" refers to a single layer and/or multiple layers disposed between a first electrode and a second electrode of an OLED.

At least one indenopyridine-based compound represented by Formula 1 may be included in an organic layer disposed between a pair of electrodes of an OLED. For example, the at least one indenopyridine-based compound represented by Formula 1 may be included in an emission layer. The at least one indenopyridine-based compound represented by Formula 1 may serve as a host of the emission layer.

In an embodiment, provided is an OLED including a first electrode; a second electrode facing the first electrode; and an organic layer that is disposed between the first electrode and the second electrode and includes an emission layer, wherein the organic layer includes the indenopyridine-based compound represented by Formula 1.

As used herein, the expression "(the organic layer) may include at least one indenopyridine-based compound of Formula 1" may be understood as "(the organic layer) may include one indenopyridine-based compound represented by Formula 1 or at least two different compounds selected from indenopyridine-based compounds represented by Formula 1".

In some embodiments, the organic layer may only include Compound 1 as the indenopyridine-based compound. For example, Compound 1 may be included in the emission layer of the organic light-emitting device. Alternatively, the organic layer may include Compound 1 and Compound 2 as the indenopyridine-based compound. For example, Compound 1 and Compound 2 may be included in the same layer or respectively included in two different layers (e.g., an emission layer or a first emission layer and a second emission layer).

FIG. 1 illustrates a schematic cross-sectional view of an OLED 100 according to an embodiment. Hereinafter, a structure and a manufacturing method of an OLED will be described in more detail with reference to FIG. 1.

A substrate 110 may be a substrate used in a general OLED, and may be a glass substrate or a transparent plastic substrate having excellent mechanical strength, thermal stability, transparency, surface smoothness, ease of handling, and waterproofness.

A first electrode 120 may be formed by applying a first electrode material on the substrate 110 by deposition or sputtering. In an embodiment, the first electrode 120 is an anode, and the first electrode material may be selected from materials having a high work function to facilitate hole injection. The first electrode 120 may be a reflective electrode or a transparent electrode. Examples of the first electrode material may include indium-tin oxide (ITO), Indium-zinc-oxide (IZO), tin oxide ($SnO_2$), and zinc oxide (ZnO). Also, in an embodiment, magnesium (Mg), aluminum (Al), aluminum-lithium (Al—Li), calcium (Ca), magnesium-indium (Mg—In), or magnesium-silver (Mg—Ag) is used as the first electrode material, and the first electrode 120 may be formed as a reflective electrode.

The first electrode 120 may be formed as a single layer or may have a multi-layered structure having at least two layers. For example, the first electrode 120 may have a three-layered structure, e.g., ITO/Ag/ITO.

An organic layer 130 is formed on the first electrode 120.

The organic layer 130 may sequentially include a hole injection layer (HIL) 131, a hole transport layer (HTL) 132, a H-functional layer, a buffer layer, an emission layer (EML) 133, an electron transport layer (ETL) 134, and an electron injection layer (EIL) 135.

The HIL 131 may be formed on the first electrode 120 by using various methods such as vacuum deposition, spin coating, casting, or LB deposition.

When the HIL 131 is formed by vacuum deposition, the deposition conditions may vary according to a compound used as a material for forming the HIL 131 and a structure and thermal characteristics of a desired HIL. For example, the deposition condition may be a deposition temperature of about 100 to about 500° C., a degree of vacuum of about $10^{-8}$ to about $10^{-3}$ torr, and a deposition speed of about 0.01 to about 100 Å/sec.

When the HIL 131 is formed by spin coating, the coating condition may vary according to a compound used as a material for forming the HIL 131, a structure of a desired HIL, and thermal characteristics. For example, the coating condition may be a coating speed of about 2,000 to about 5,000 rpm and a heat treatment temperature for removing a solvent after coating of about 80 to about 200° C.

Exemplary materials for forming the HIL 131 include N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino) triphenylamine (m-MTDATA), N,N'-di(1-naphthyl)-N,N'-diphenylbenzidine (NPB), 4,4',4"-tris(N,N-diphenylamino)triphenylamine) (TDATA), 4,4',4"-tris[2-naphthyl(phenyl)amino]triphenylamine) (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonicacid (PANI/CSA), and polyaniline/poly(4-styrenesulfonate) (PANI/PSS):

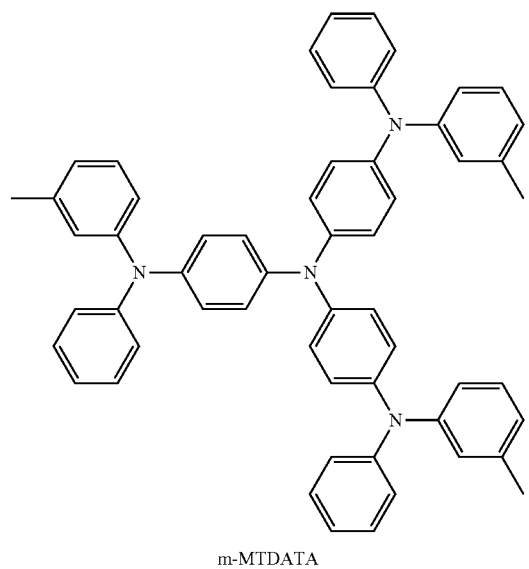

m-MTDATA

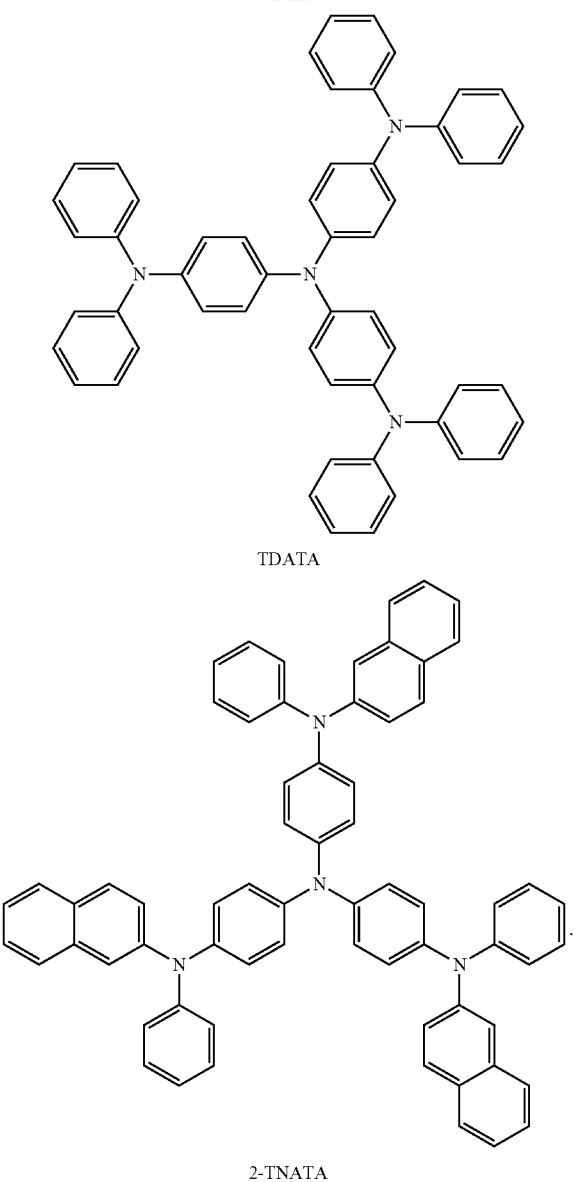

TDATA

2-TNATA

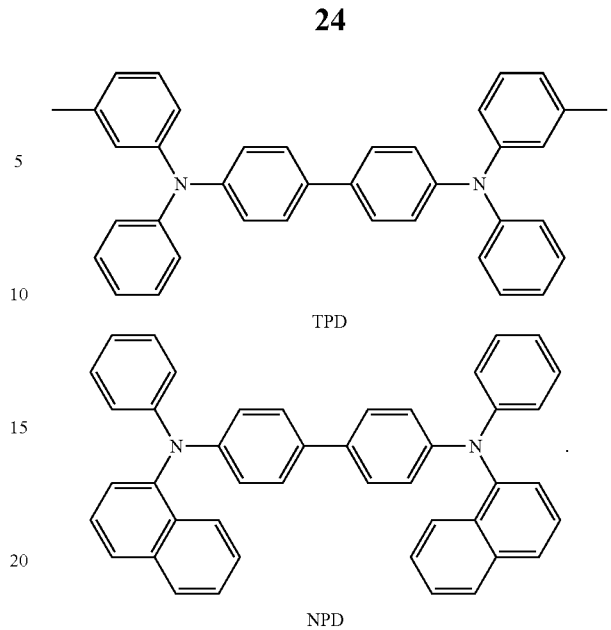

TPD

NPD

A thickness of the HTL 132 may be in a range of about 50 Å to about 2,000 Å, for example, in a range of about 100 Å to about 1,500 Å. Maintaining a thickness of the HTL 132 within this range may help provide satisfactory hole transporting properties without a substantial increase in driving voltage.

The H-functional layer (a functional layer having both hole injection and transport abilities) may include at least one of the HIL materials and the HTL materials stated above, and a thickness of the H-functional layer may be in a range of about 500 Å to about 10,000 Å, for example, in a range of about 100 Å to about 1,000 Å. Maintaining a thickness of the H-functional layer within this range may help provide satisfactory hole injecting and transporting properties without a substantial increase in driving voltage.

At least one of the HIL 131, the HTL 132, and the H-functional layer may include at least one of a compound represented by Formula 300 and a compound represented by Formula 350:

<Formula 300>

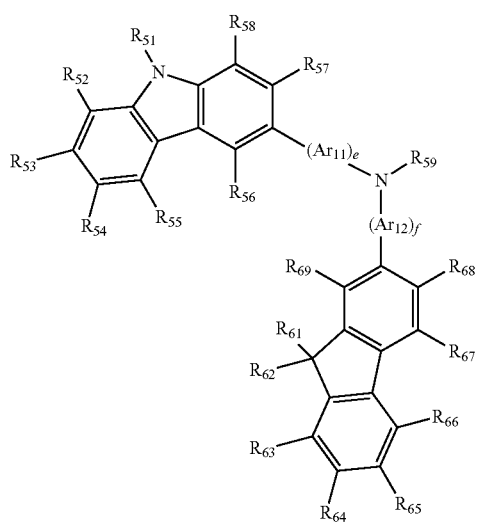

A thickness of the HIL 131 may be in a range of about 100 Å to about 10,000 Å, for example, in a range of about 100 Å to about 1,000 Å. Maintaining a thickness of the HIL 131 within this range may help provide satisfactory hole injecting properties without a substantial increase in driving voltage.

Next, the HTL 132 may be formed on the HTL 131 by vacuum deposition, spin coating, casting, or LB deposition. When the HTL is formed by vacuum deposition or spin coating, the deposition and coating conditions vary depending on a used compound, but generally the conditions may be about the same as the conditions for forming the HIL 131.

Exemplary materials for forming the HTL 131 include carbazole derivatives, such as N-phenylcarbazole and polyvinylcarbazole, N,N'-bis(3-methylphenyl)-N,N'-diphenyl-[1,1-biphenyl]-4,4'-diamine (TPD), 4,4',4''-tris(N-carbazolyl)triphenylamine (TCTA), and N,N'-di(1-naphthyl)-N,N'-diphenylbenzidine (NPB):

<Formula 350>

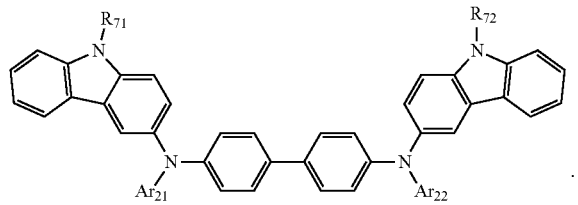

In Formulae 300 and 350, $Ar_{11}$, $Ar_{12}$, $Ar_{21}$, and $Ar_{22}$ are each independently a substituted or unsubstituted $C_5$-$C_{60}$ arylene group. Detailed descriptions about $Ar_{11}$, $Ar_{12}$, $Ar_{21}$, and $Ar_{22}$ may be referred to the detailed description of $L_1$ stated above.

In Formula 300, e and f are each independently an integer of 0 to 5, for example, 0, 1, or 2. In one embodiment, e may be 1, and f may be 0.

In Formulae 300 and 350, $R_{51}$ to $R_{58}$, $R_{61}$ to $R_{69}$, $R_{71}$, and $R_{72}$ may each independently be a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. In some embodiments, $R_{51}$ to $R_{58}$, $R_{61}$ to $R_{69}$, $R_{71}$, and $R_{72}$ may each independently be one of:

a hydrogen atom; a deuterium atom; a halogen atom; a hydroxyl group; a cyano group; a nitro group; an amino group; an amidino group; a hydrazine group; a hydrazone group; a carboxyl group or a salt thereof; a sulfonic acid group or a salt thereof; a phosphoric acid group or a salt thereof; a $C_1$-$C_{10}$ alkyl group (e.g., a methyl group, an ethyl group, a propyl group, a butyl group, a pentyl group, or a hexyl group); and a $C_1$-$C_{10}$ alkoxy group (e.g., a methoxy group, an ethoxy group, a propoxy group, a butoxy group, or a pentoxy group);

a $C_1$-$C_{10}$ alkyl group and a a $C_1$-$C_{10}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, and a phosphoric acid group or a salt thereof;

a phenyl group; a naphthyl group; an anthryl group; a fluolenyl group; and a pyrenyl group; and a phenyl group, a naphthyl group, an anthryl group, a fluolenyl group, and a pyrenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{59}$ may be one of:
a phenyl group; a naphthyl group; an anthryl group; a biphenyl group; and a pyridyl group; and a phenyl group, a naphthyl group, an anthryl group, a biphenyl group, and a pyridyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In some embodiments, a compound represented by Formula 300 may be represented by Formula 300A:

<Formula 300A>

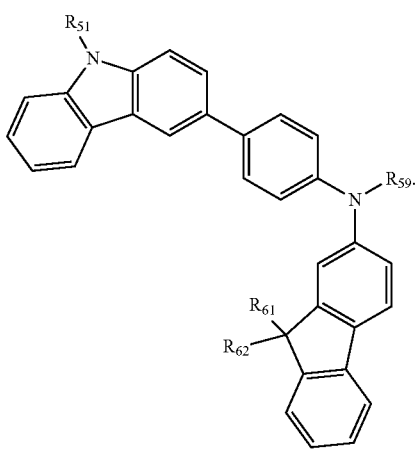

In Formula 300A, detailed descriptions about $R_{51}$, $R_{61}$, $R_{62}$, and $R_{59}$ are as stated above.

In some embodiments, at least one of the HIL 131, the HTL 132, and the H-functional layer may include at least one of Compounds 301 to 320:

301

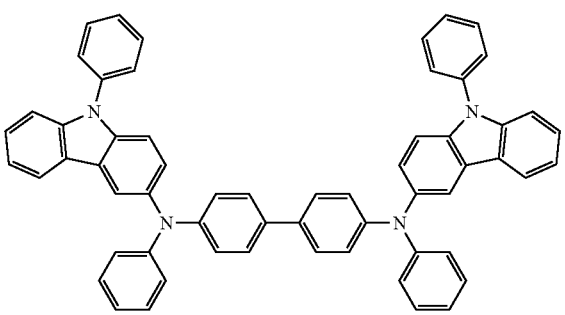

302

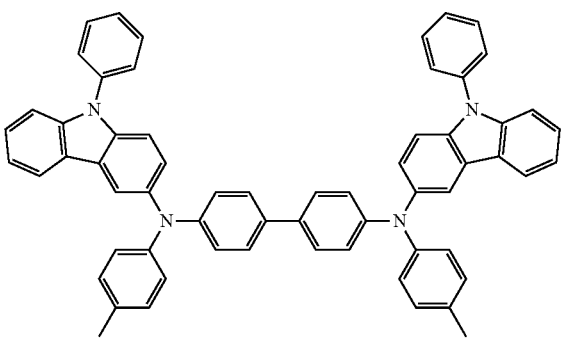

303
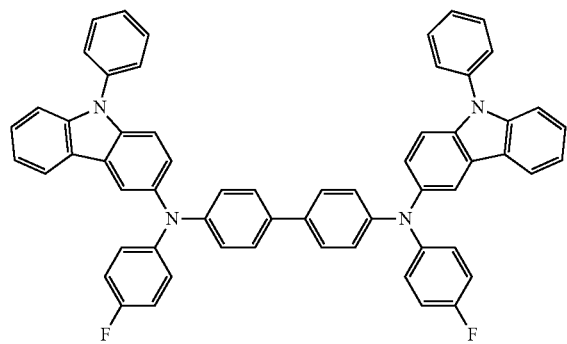
304
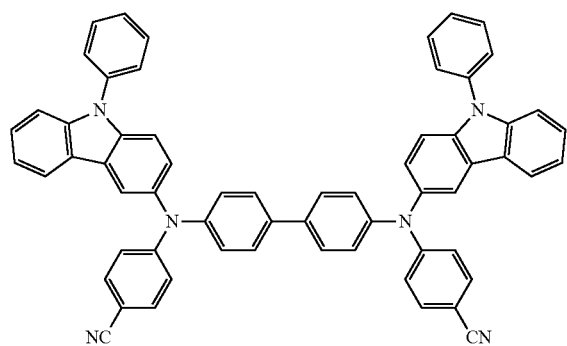
305
306
307
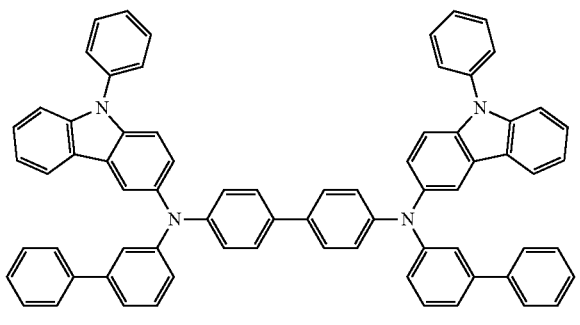
308
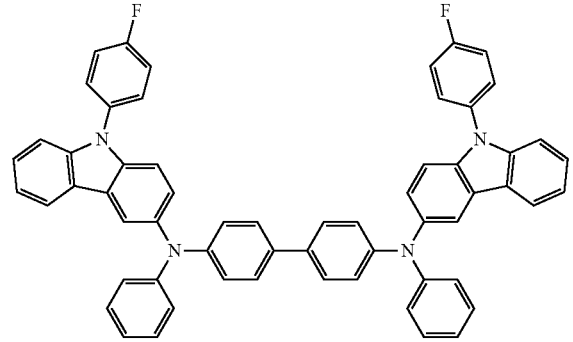
309
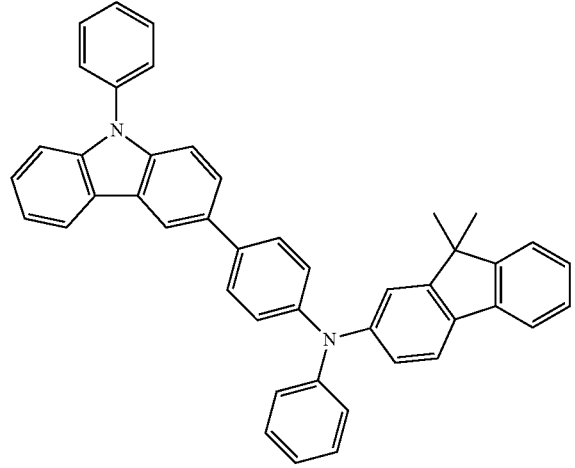

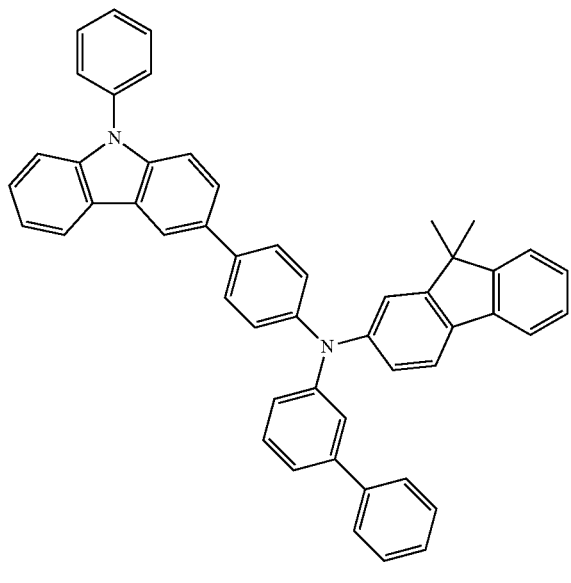
310
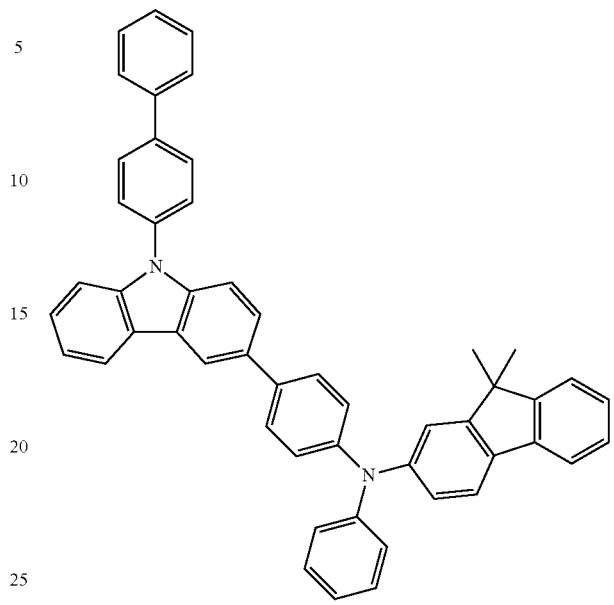
312
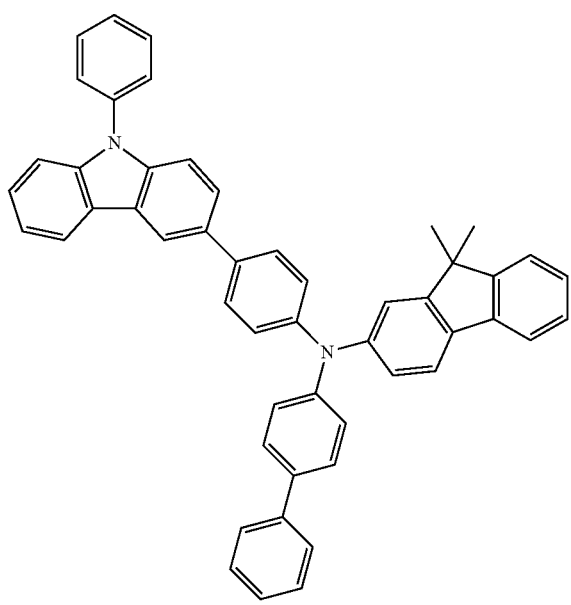
311
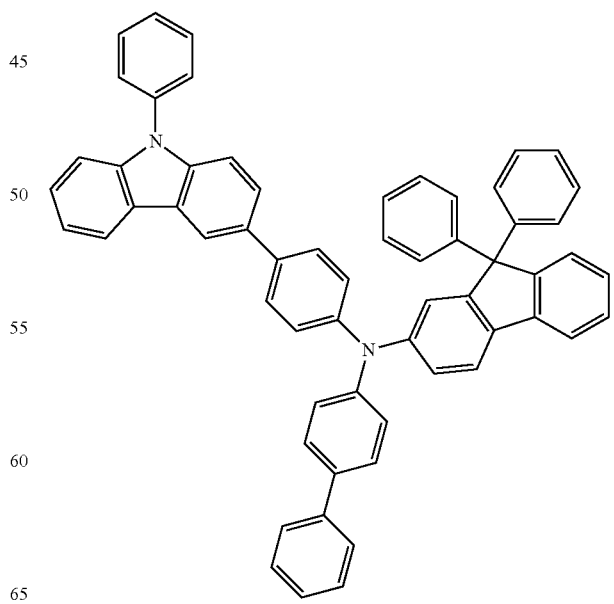
313

314
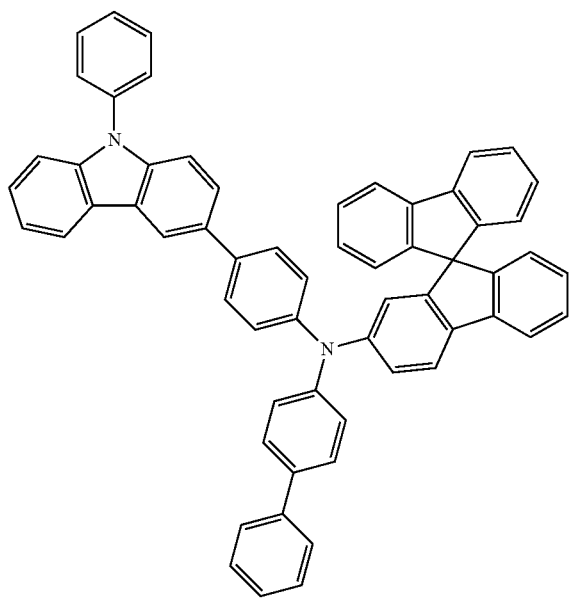
315
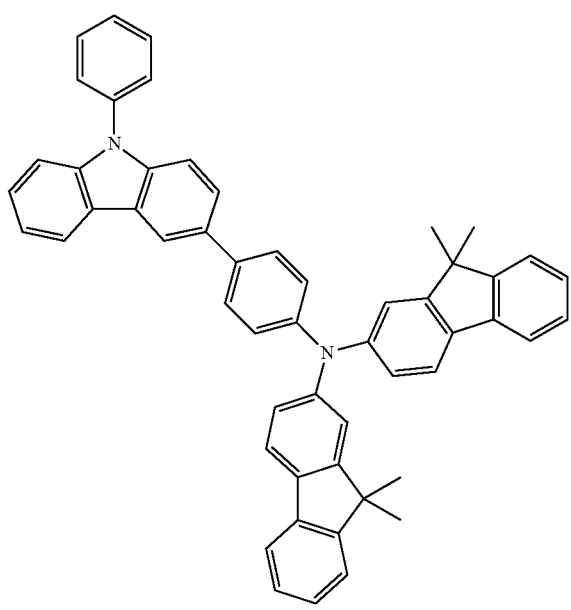
316
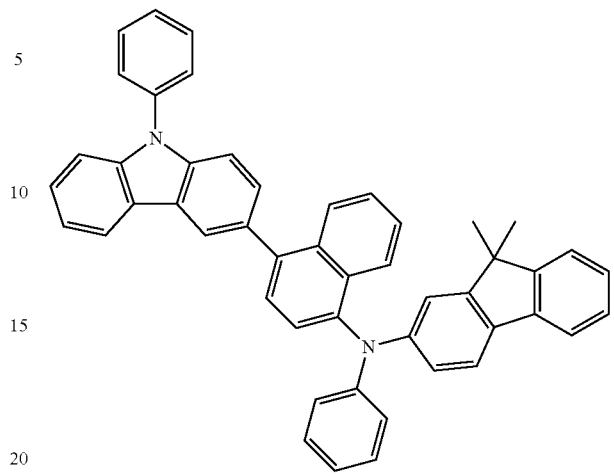
317
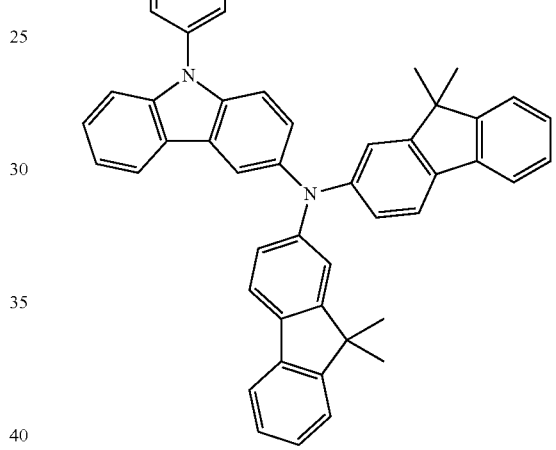
318
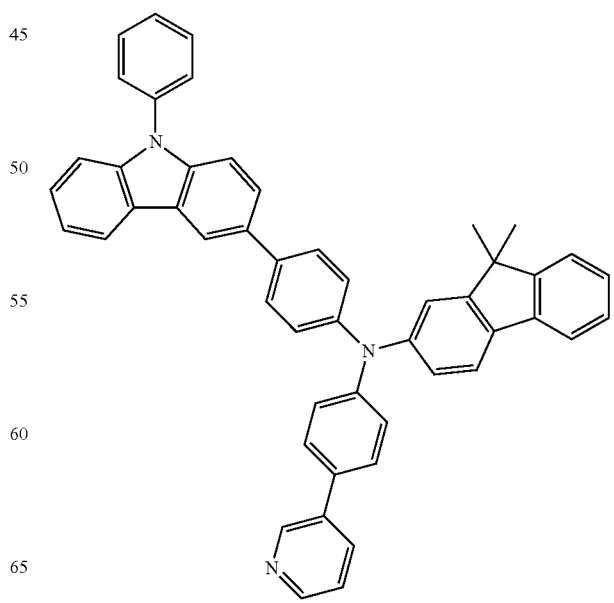

-continued

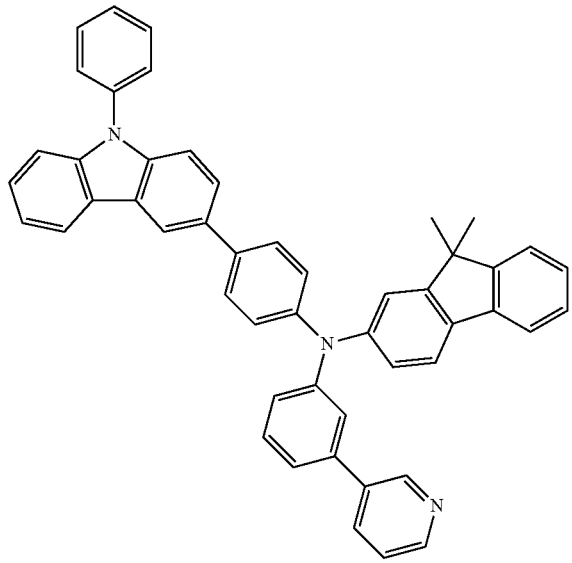
319

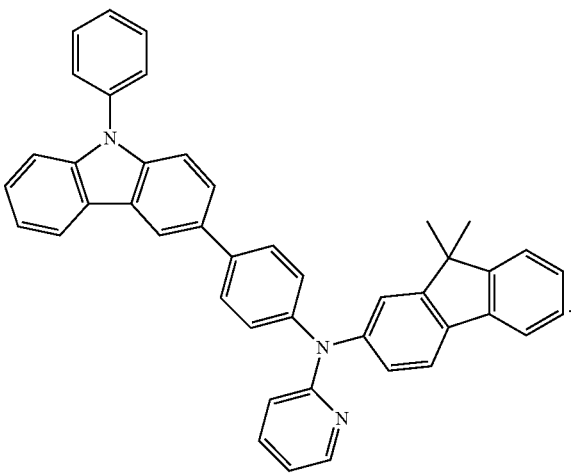
320

The at least one of the HIL 131, the HTL 132, and the H-functional layer may further include a charge-generating material in addition to the HIL material, the HTL material, and/or a material having both hole injecting and transporting capabilities to increase conductivity of the layers.

The charge-generating material may be, for example, one of a quinine derivative, a metal oxide, and a cyano-containing compound. Examples of charge-generating material include quinone derivatives, such as tetra-cyanoquinodimethane (TCNQ) and 2,3,5,6-tetrafluoro-tetracyano-1,4-benzoquinodimethane (F4-TCNQ); metal oxides, such as a tungsten oxide and a molybdenum oxide; and cyano-containing compounds, such as Compound 100 (HAT-CN):

<Compound 100>

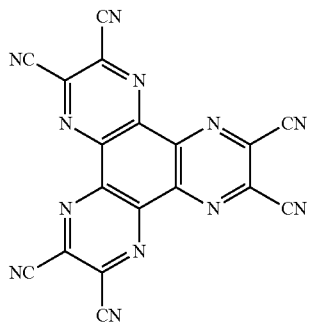

When the HIL 131, the HTL 132, and the H-functional layer further include the charge-generating material, the charge-generating material may be homogeneously or unhomogeneously dispersed in the HIL 131, the HTL 132, and the H-functional layer.

The buffer layer may be disposed between the at least one of the HIL 131, the HTL 132, and the H-functional layer and the EML 133. The buffer layer increases efficiency by compensating an optical resonance distance according to the wavelength of light emitted from the EML 133. The buffer layer may include an HIL material and an HTL material. Also, the buffer layer may include the same material as one of the materials included in the HIL 131, the HTL 132, and the H-functional layer formed under the buffer layer.

The EML 133 may be formed on the HIL 131, the HTL 132, the H-functional layer, or the buffer layer by vacuum deposition, spin coating, casting, or LB deposition. When the EML is formed by vacuum deposition or spin coating, the deposition and coating conditions vary according to a used compound, but generally the condition may be about the same as the condition for forming the HIL 131.

The EML 133 may include an EML material. In some embodiments, the EML 133 may include an indenopyridine-based compound represented by Formula 1. The indenopyridine-based compound represented by Formula 1 may serve as a host.

Also, the EML 133 may further include a host and a dopant.

Examples of the host include Alq$_3$, 4,4'-N,N'-dicabazole-biphenyl (CBP), poly(n-vinylcabazole) (PVK), 9,10-di(naphthalene-2-yl)anthracene (DNA), TCTA, 1,3,5-tris(N-phenylbenzimidazole-2-yl)benzene (TPBI), 3-tert-butyl-9,10-di(naphth-2-yl) anthracene (TBADN), E3, and distyrylarylene (DSA), dmCBP (refer to the formula below), and Compounds 501 through 509 below:

TPBI

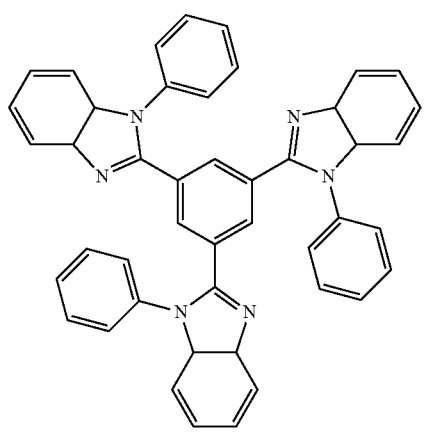

TBADN
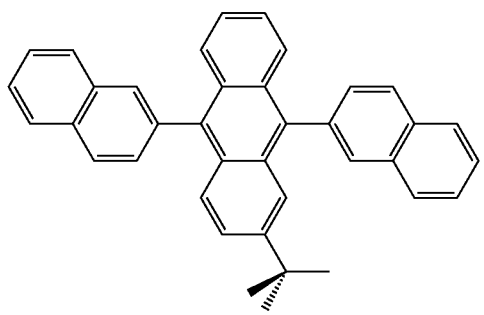
E3
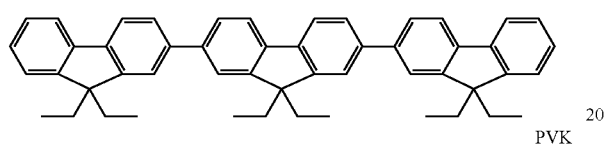
PVK
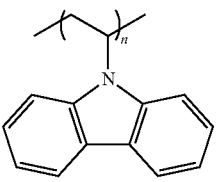
ADN
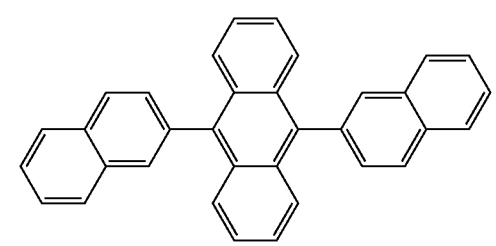
CBP
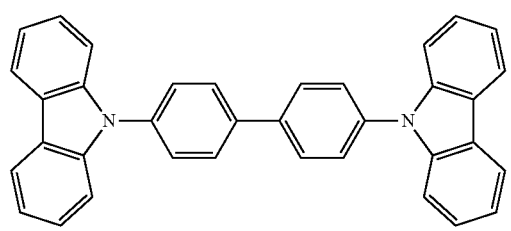
dmCBP
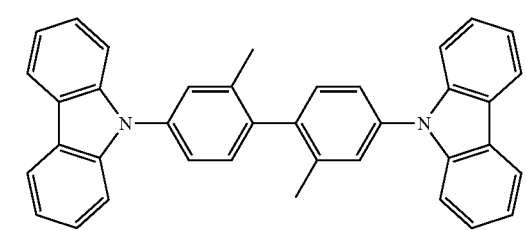
501
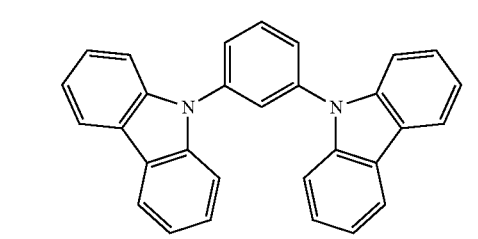
502
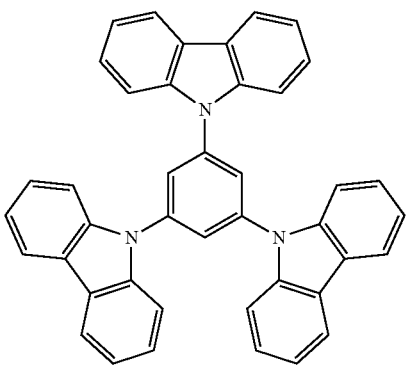
503
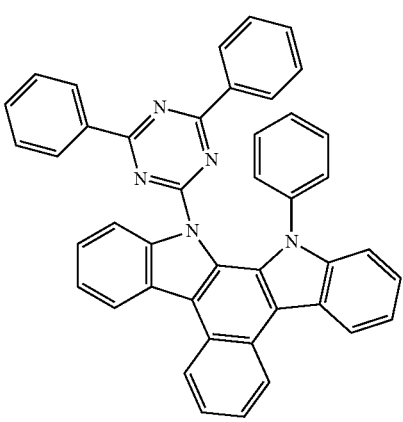
504
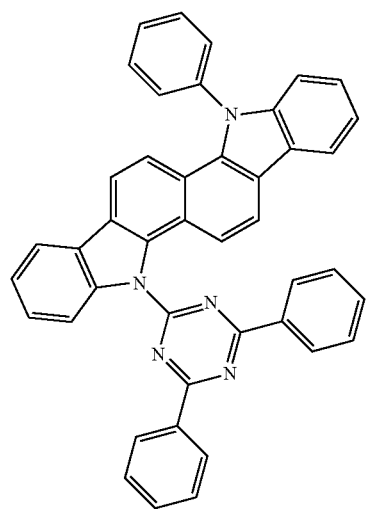

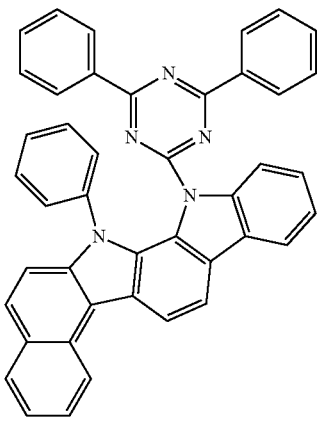

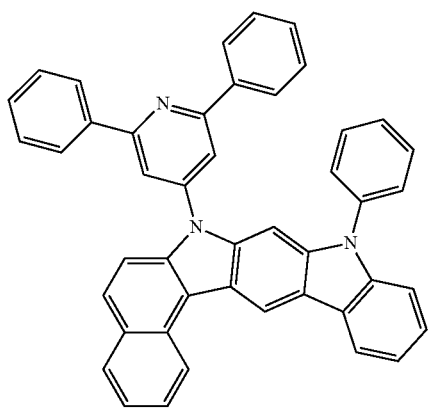

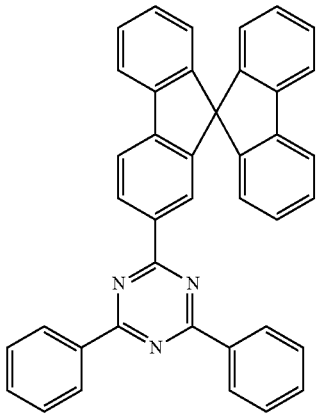

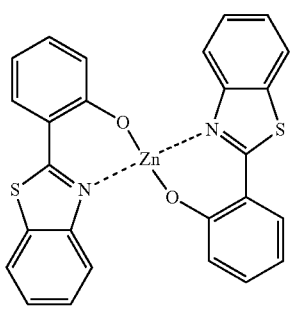

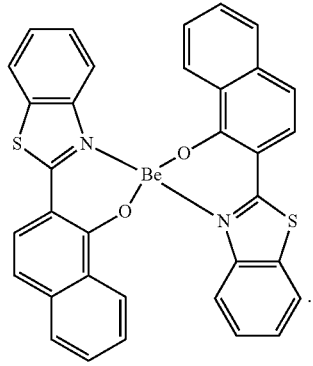

Also, the host may be an anthracene-based compound represented by Formula 400 below:

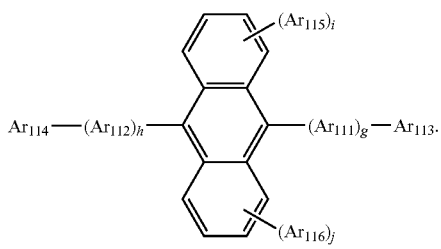

<Formula 400>

In Formula 400, $Ar_{111}$ and $Ar_{112}$ may each independently be a substituted or unsubstituted $C_5$-$C_{60}$ arylene group; $Ar_{113}$ through $Ar_{116}$ may each independently be selected from a substituted or unsubstituted $C_1$-$C_{10}$ alkyl group and a substituted or unsubstituted $C_5$-$C_{60}$ aryl group; and g, h, i, and j may each independently be an integer of 0 to 4.

For example, in Formula 400, $Ar_{111}$ and $Ar_{112}$ may each independently be:

a phenylene group, a naphthylene group, a phenanthrenylene group or a pyrenylene group; or a phenylene group, a naphthylene group, a phenanthrenylene group, fluolenyl group, or a pyrenylene group, each substituted with at least one of a phenyl group, a naphthyl group, and an anthryl group.

In Formula 400, g, h, i, and j are each independently an integer of 0, 1, or 2.

In Formula 400, $Ar_{113}$ to $Ar_{116}$ may each independently be one of:

a $C_1$-$C_{10}$ alkyl group substituted with at least one of a phenyl group, a naphthyl group, and an anthryl group;

a phenyl group; a naphthyl group; an anthryl group; a pyrenyl group; a phenathrenyl group; a fluolenyl group;

a phenyl group, a naphthyl group, an anthryl group, a pyrenyl group, a phenathrenyl group, and a fluolenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenathrenyl group, and a fluolenyl group; and

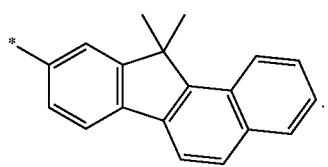 [SMILES: *c1ccc2c(c1)C(C)(C)c1c-2ccc2ccccc12]
In some embodiments, the anthracene-based compound of Formula 400 may be one of the compounds below:
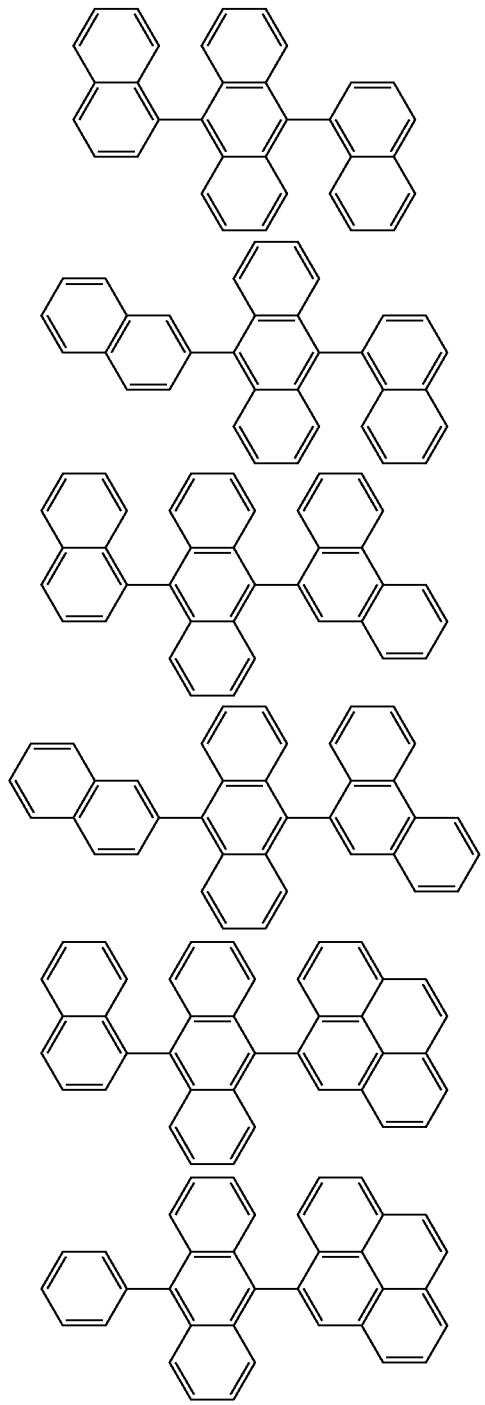
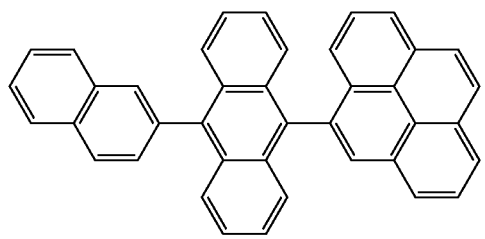
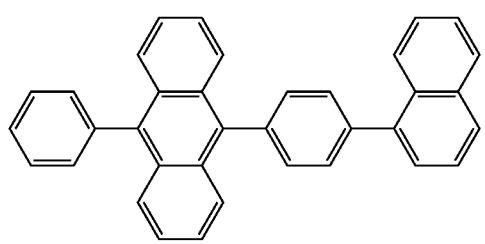
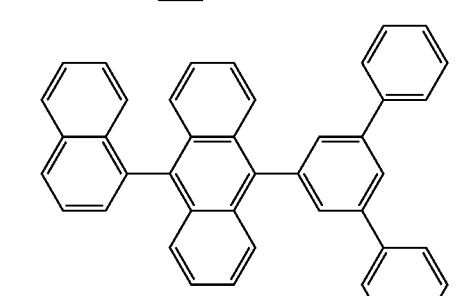
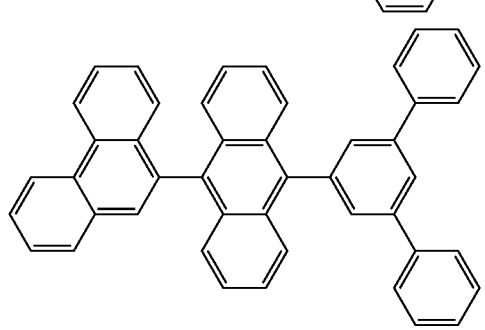
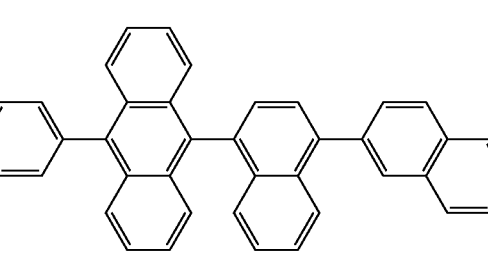
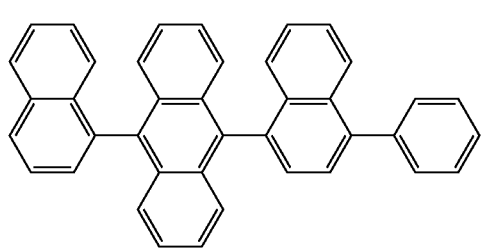

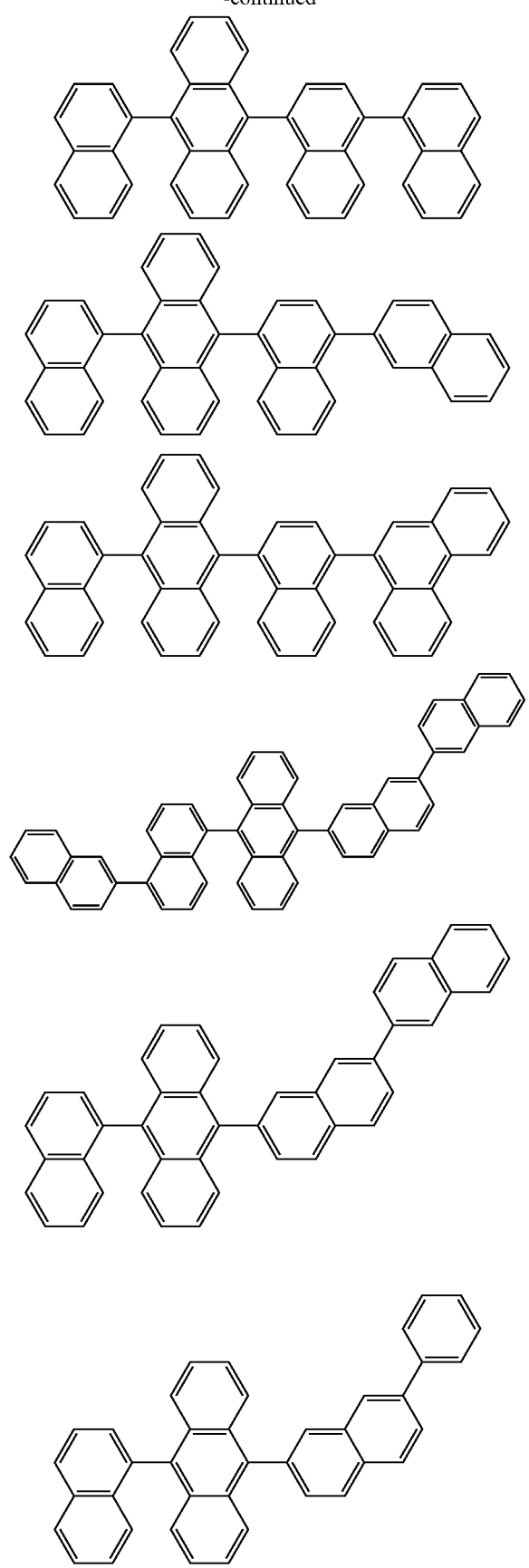
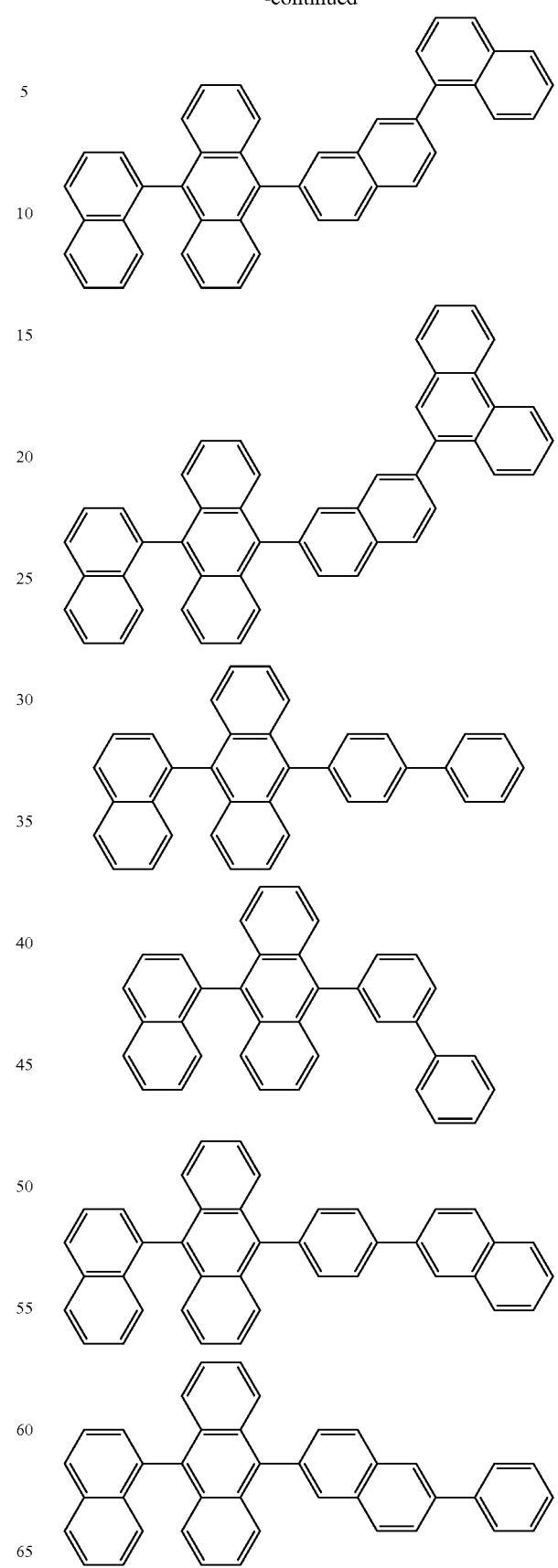

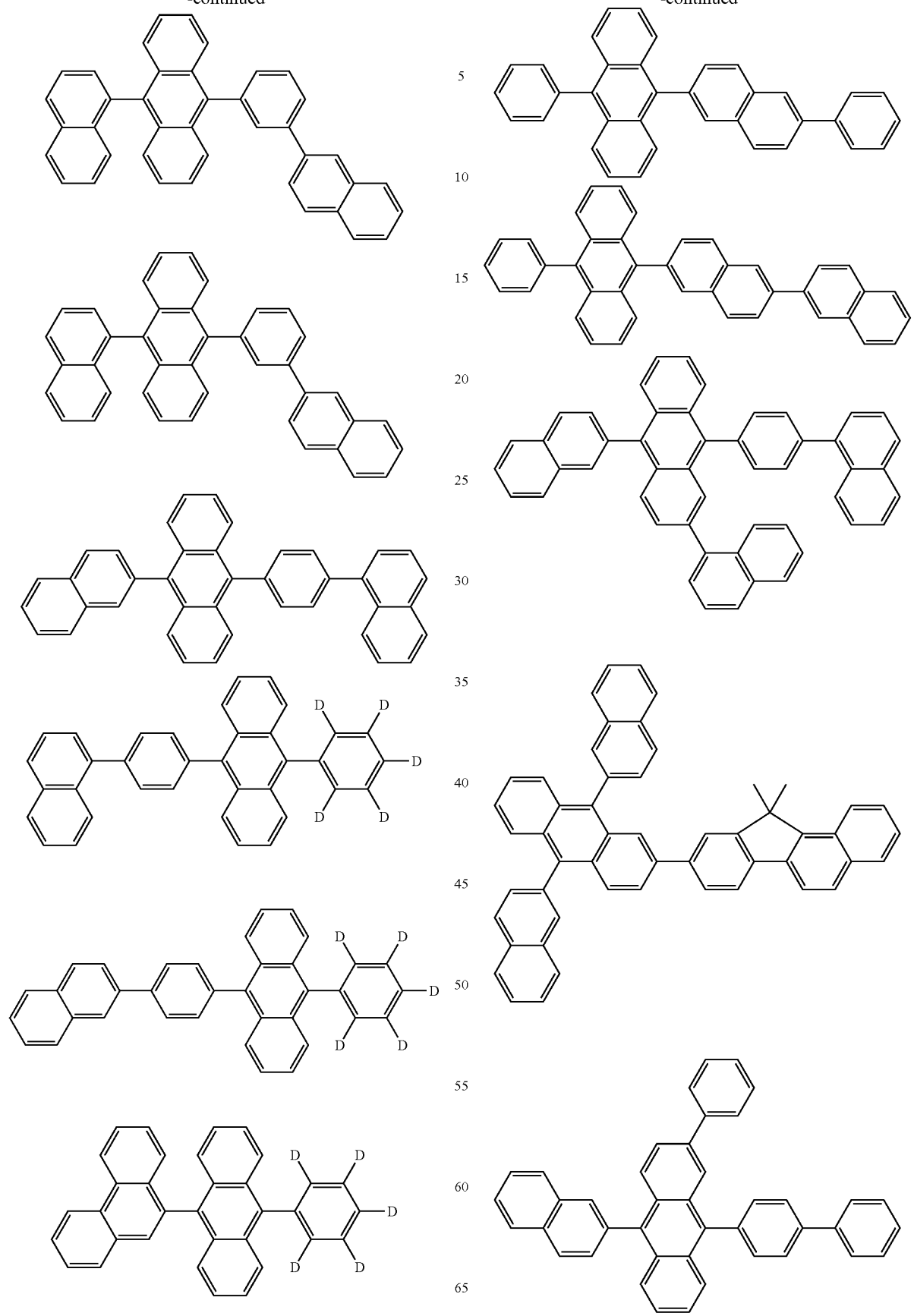

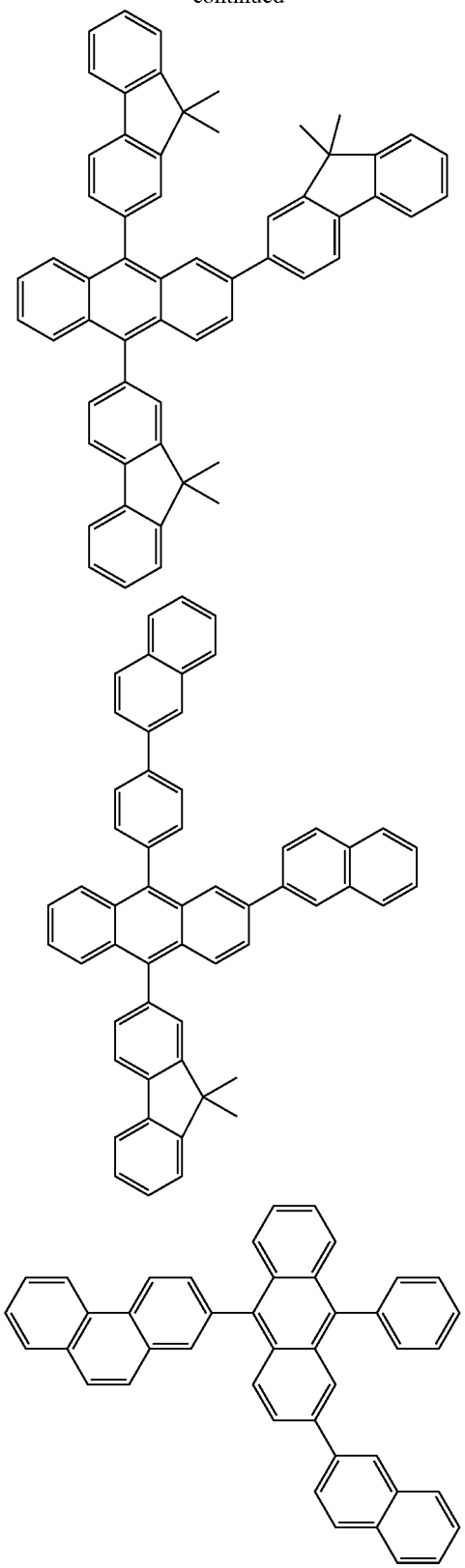

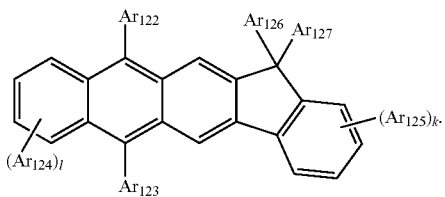
<Formula 401>

In Formula 401, detailed descriptions of $Ar_{122}$ through $Ar_{125}$ may be referred to the description of $Ar_{113}$ of Formula 400 stated above.

In Formula 401, $Ar_{126}$ and $Ar_{127}$ may each independently be a $C_1$-$C_{10}$ alkyl group (e.g., a methyl group, an ethyl group, or a propyl group).

In Formula 401, k and l may each independently be an integer of 0 to 4. For example, k and l may each independently be 0, 1, or 2.

For example, the anthrecene-based compound of Formula 401 may be one of the following compounds:

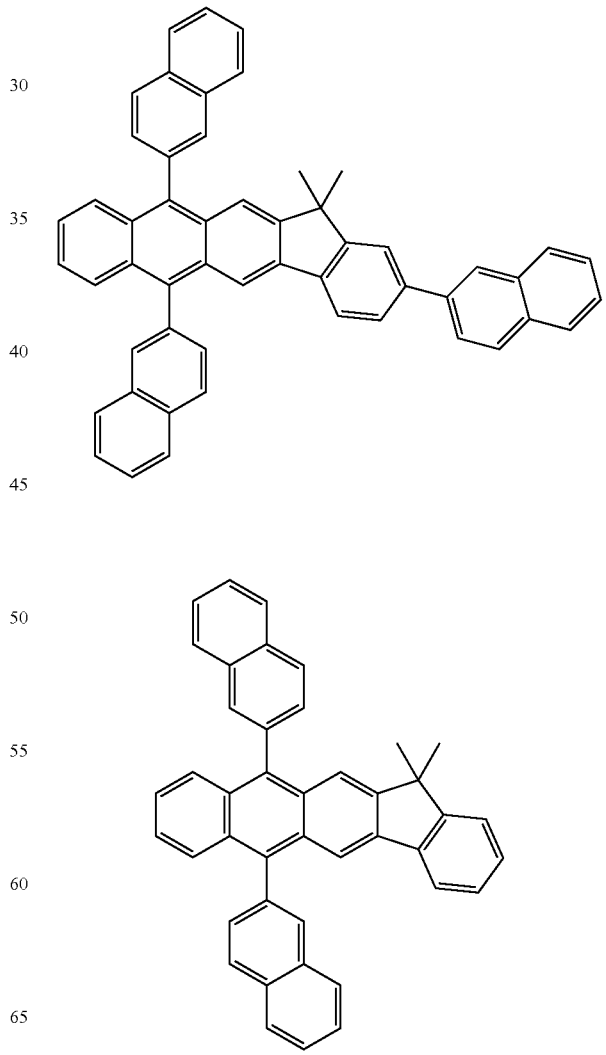

Also, an anthracene-based compound represented by Formula 401 below may be used as the host:

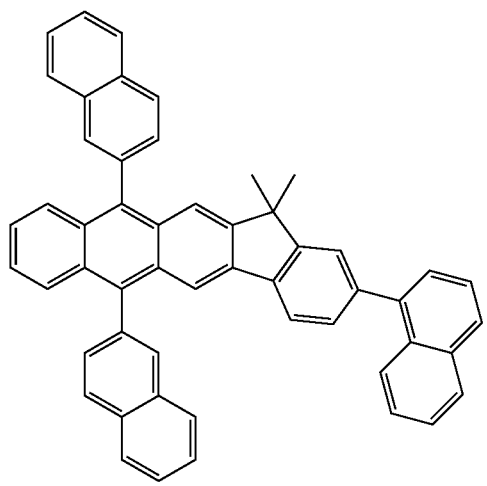
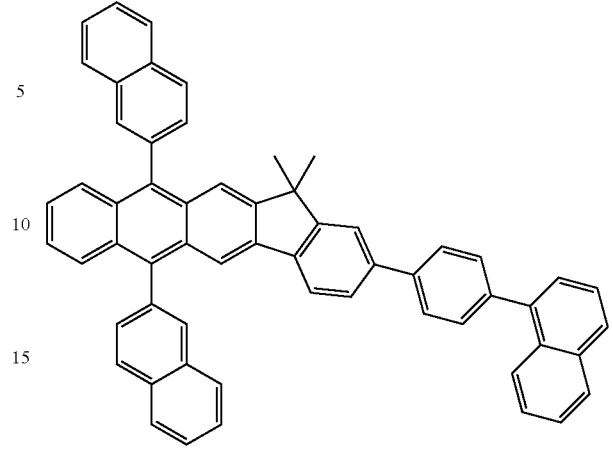
For example, a blue dopant may be one of terfluorene and compounds represented by the formulae below:
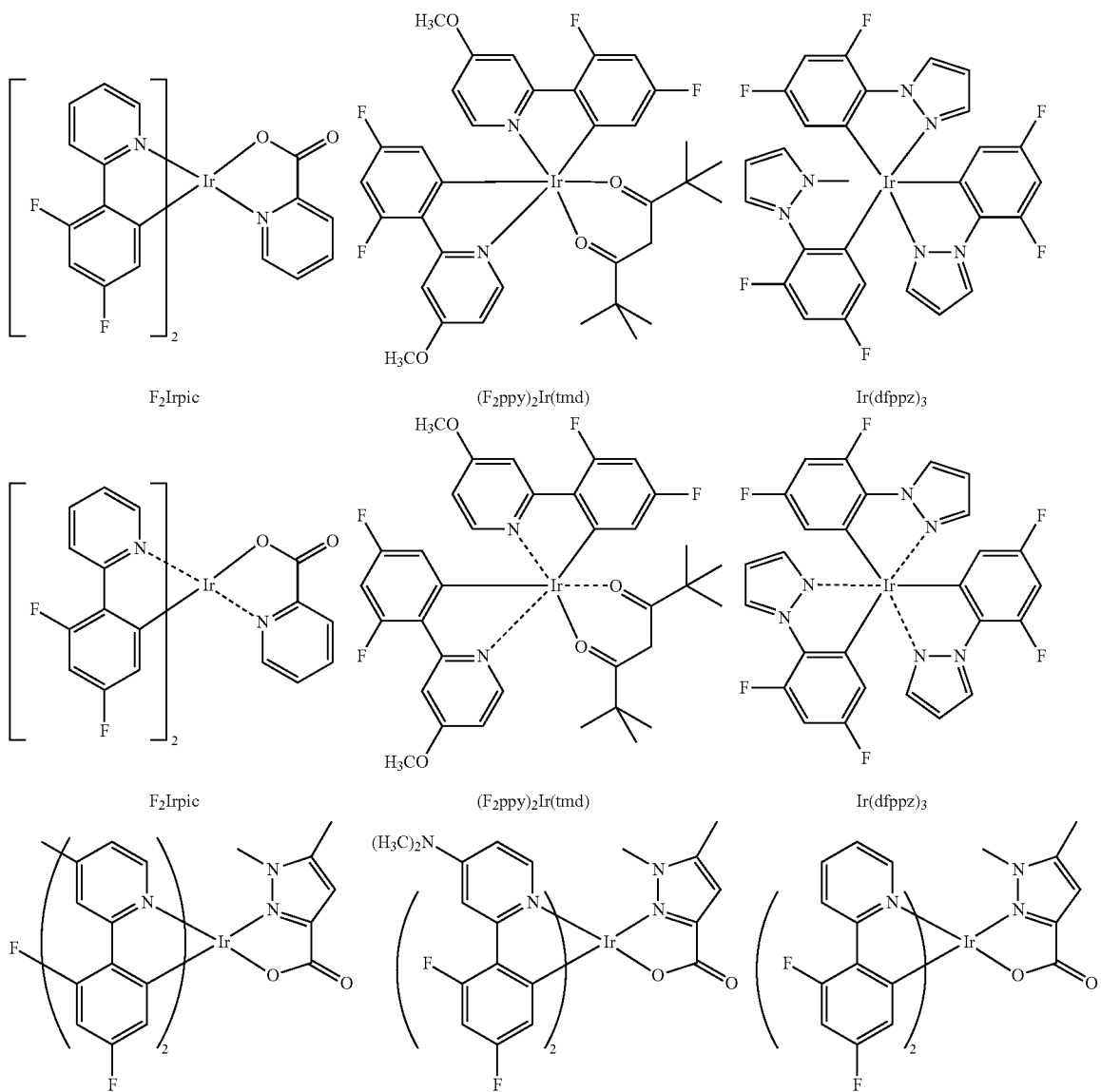

-continued
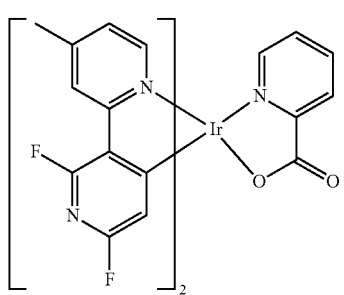
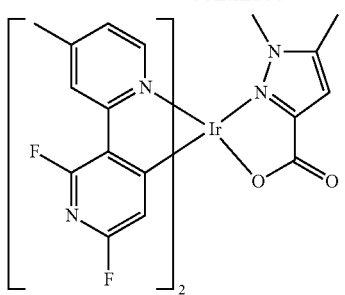
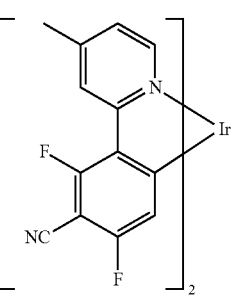
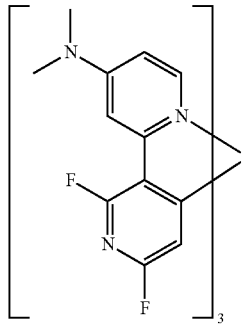
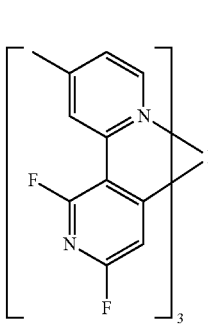
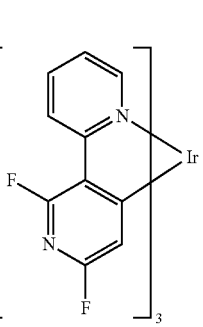
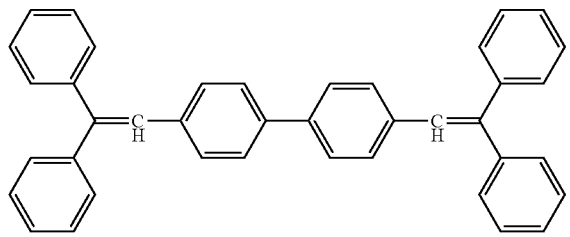
DPVBi
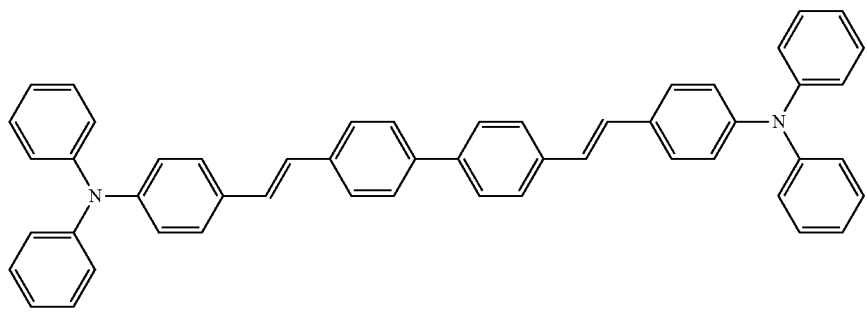
DPAVBi
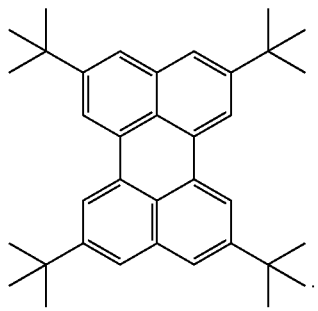
TBPe For example, a red dopant may be one of the compounds below:
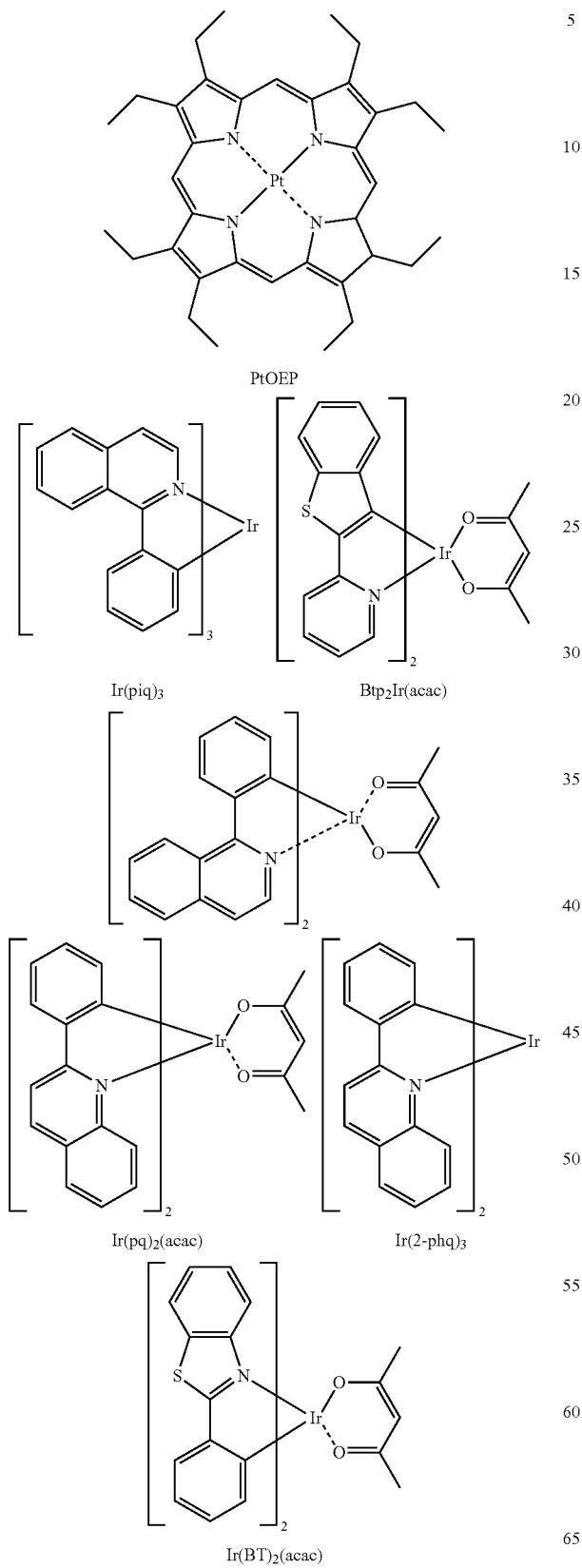
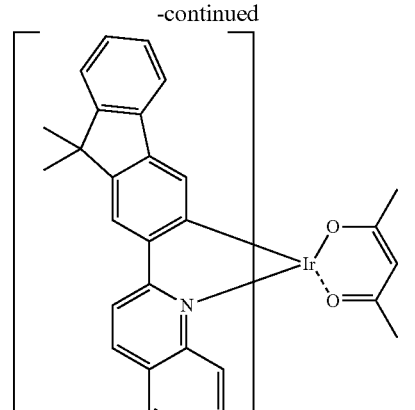
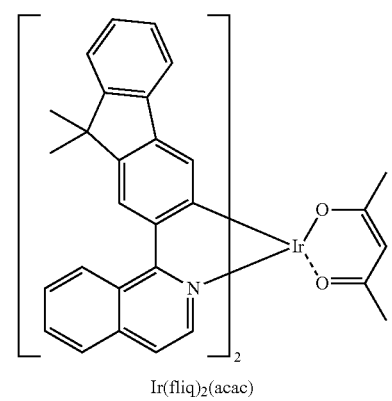
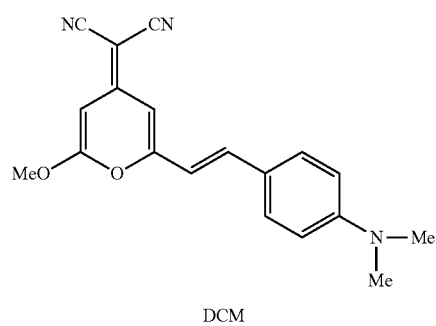
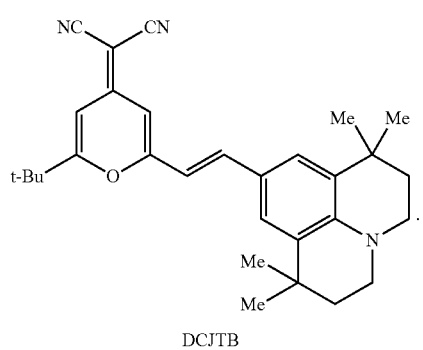
For example, a green dopant may be one of the compounds below:

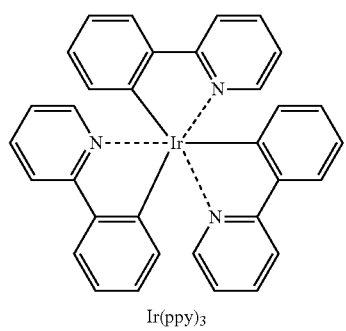
Ir(ppy)₃
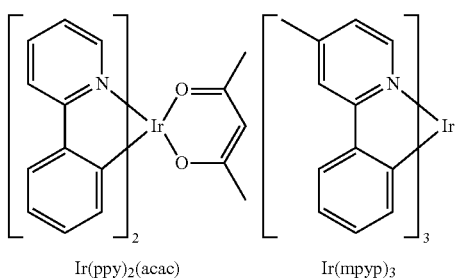
Ir(ppy)₂(acac)    Ir(mpyp)₃
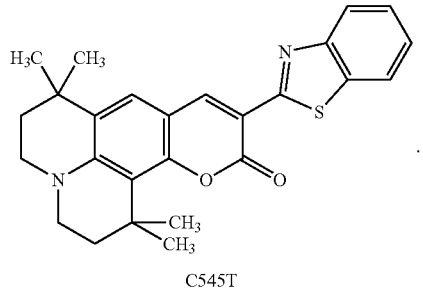
C545T
Examples of a dopant included in the EML include the organic metal complexes below:
D1
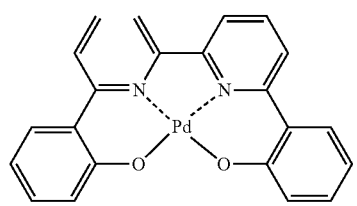
D2
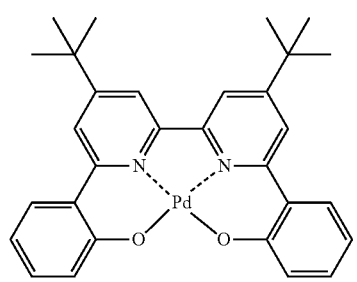
D3
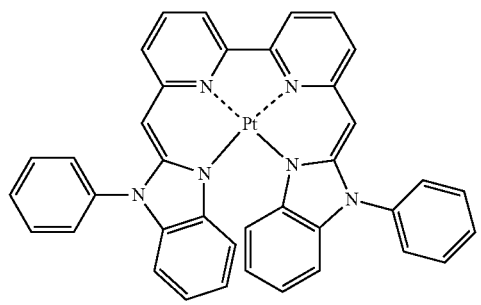
D4
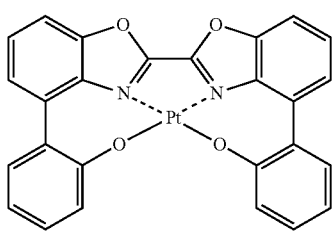
D5
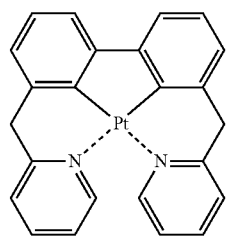
D6
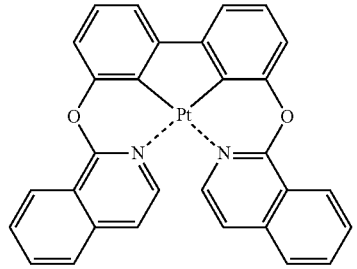
D7
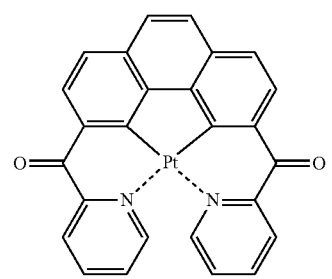
D8
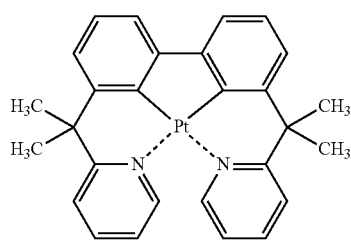

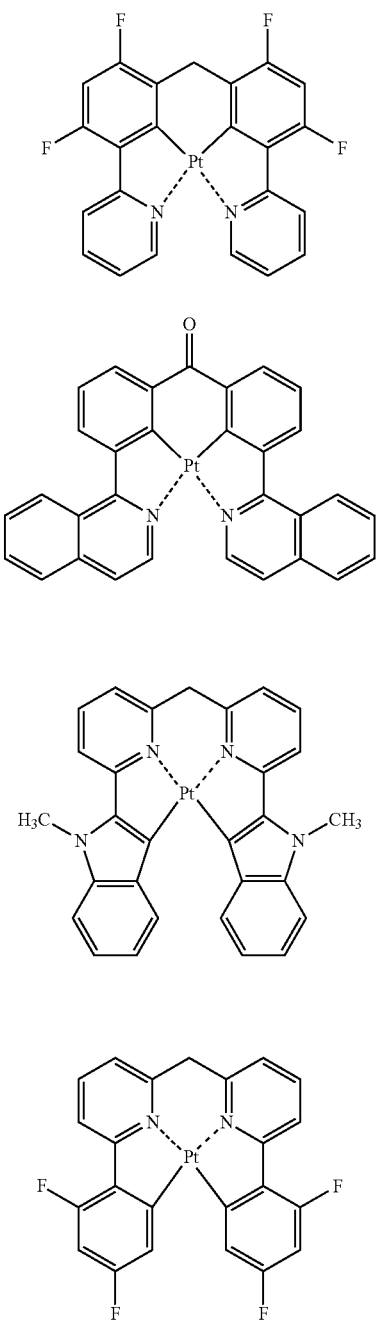
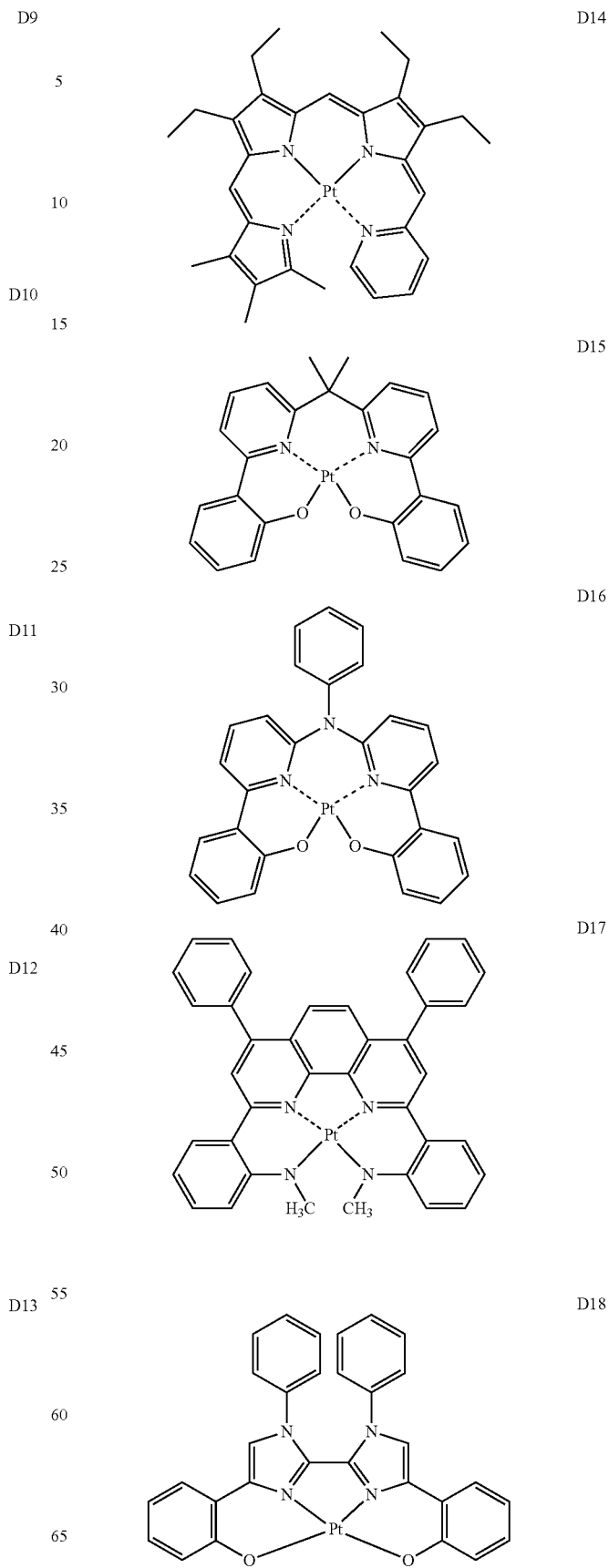

-continued
D19
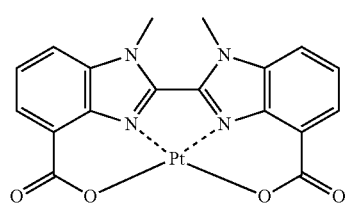
D20
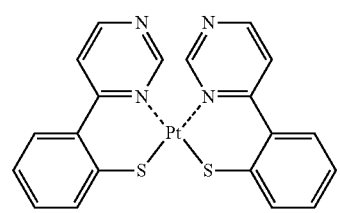
D21
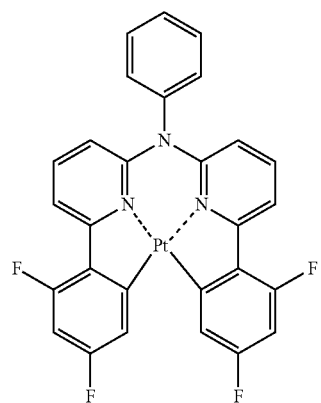
D22
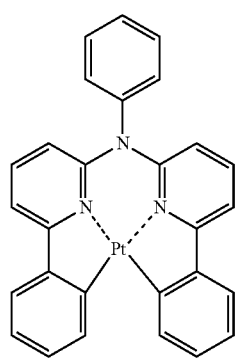
D23
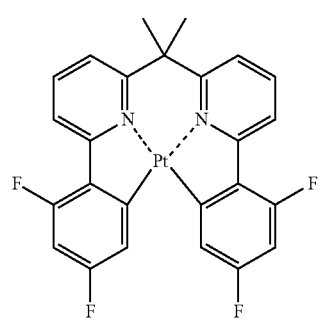
-continued
D24
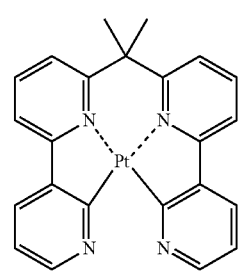
D25
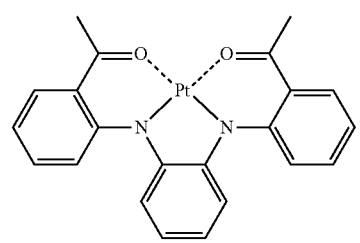
D26
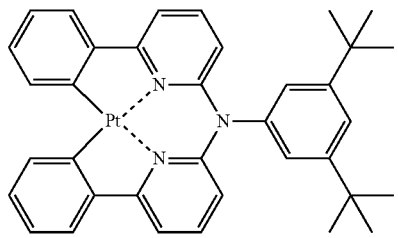
D27
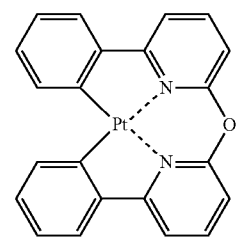
D28
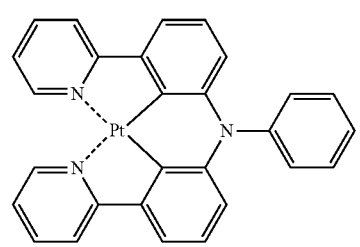
D29

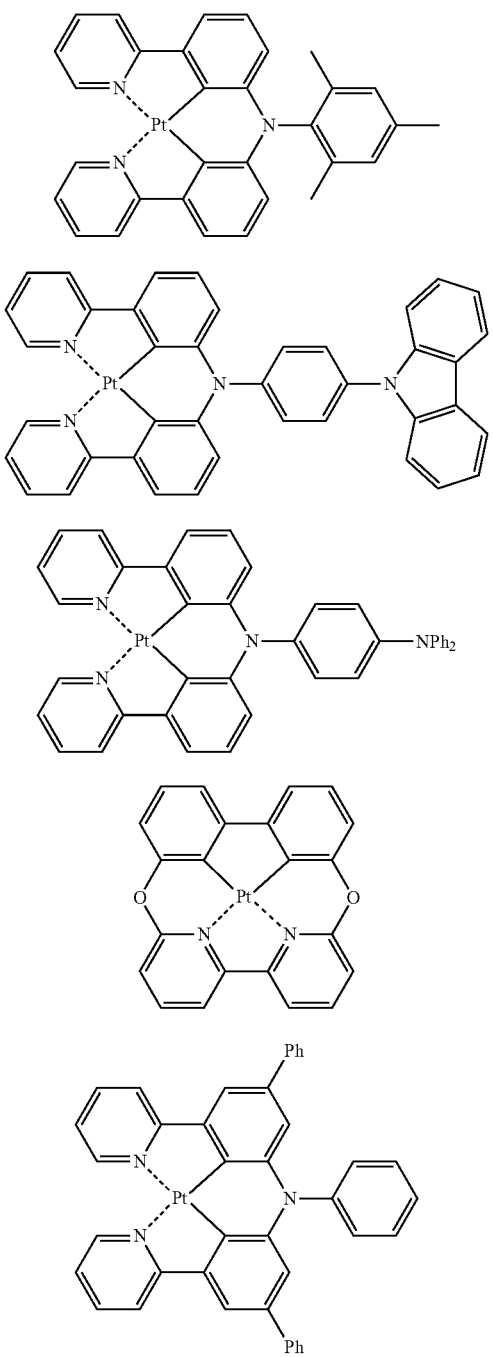
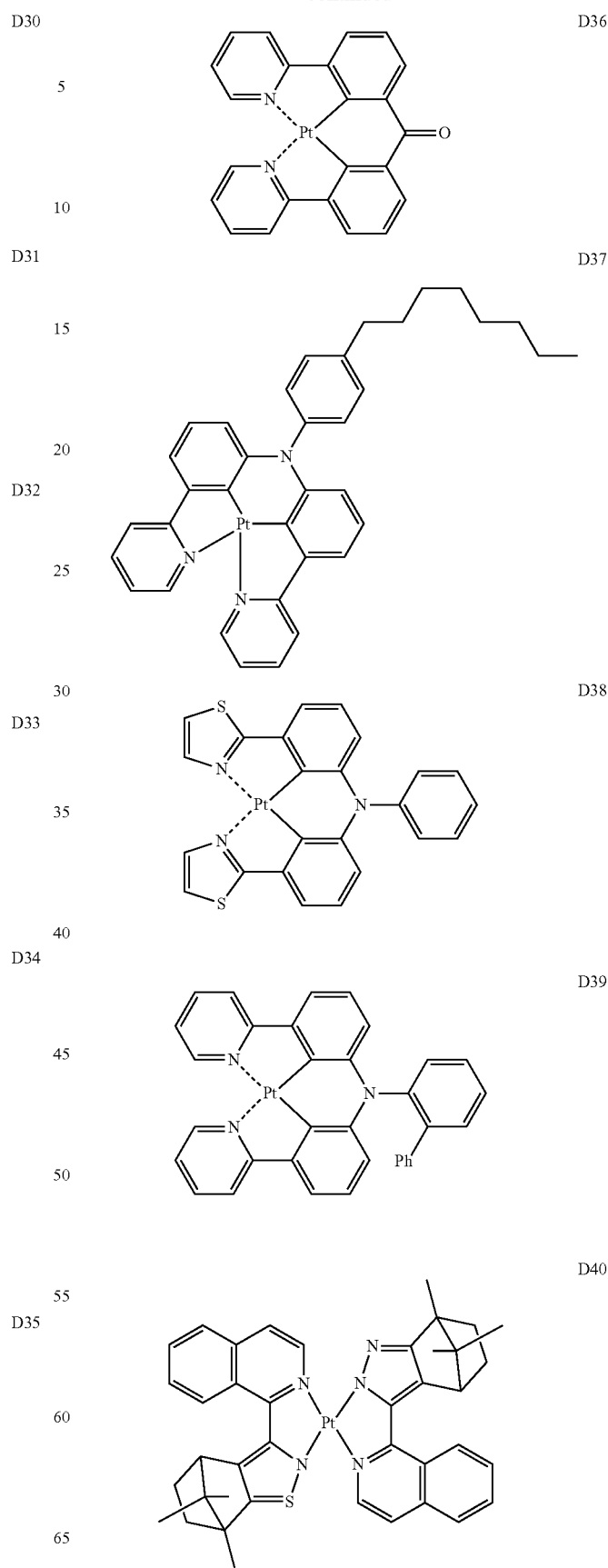

D41 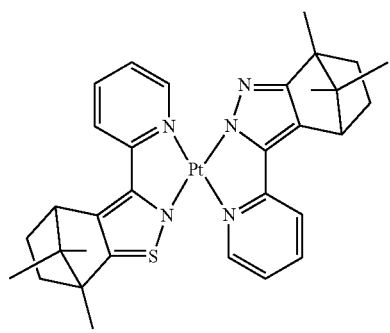
D42 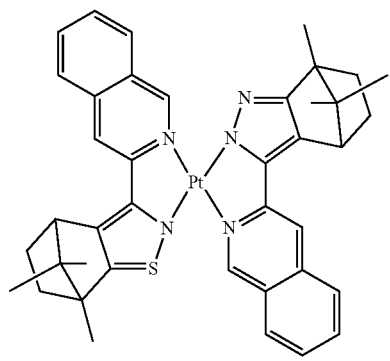
D43 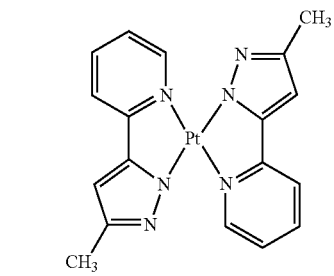
D44 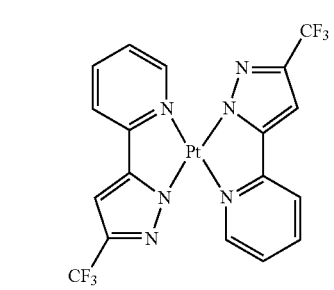
D45 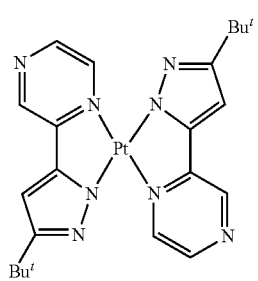
D46 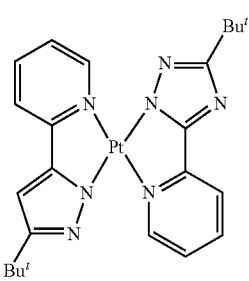
D47 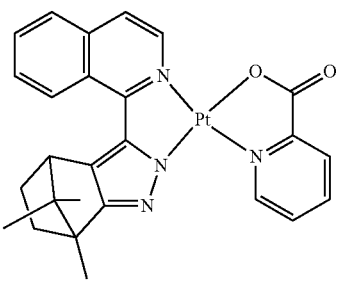
D48 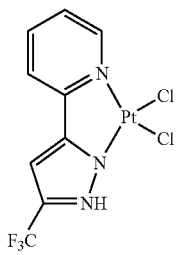
D49 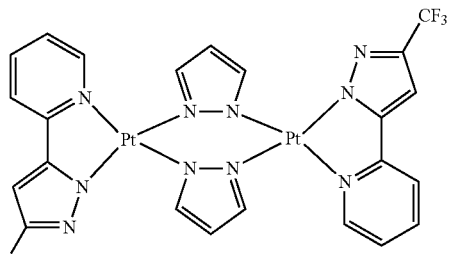
D50 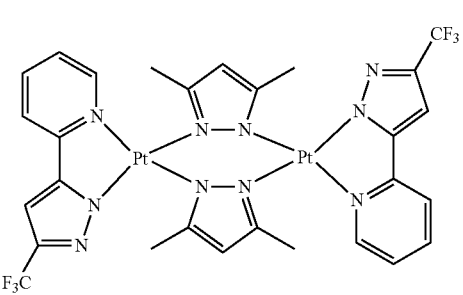

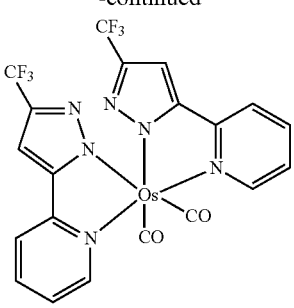

Os(fppz)₂(CO)₂

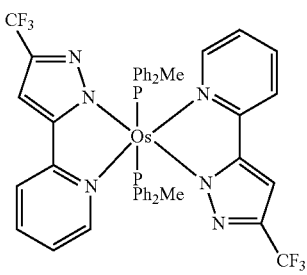

Os(fppz)₂(PPh₂Me)₂

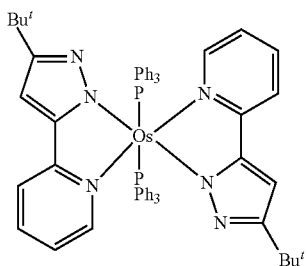

Os(bppz)₂(PPh₃)₂

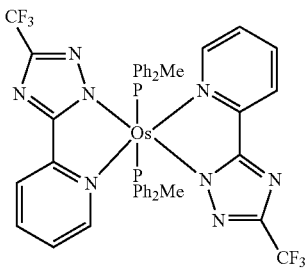

Os(fptz)₂(PPh₂Me)₂

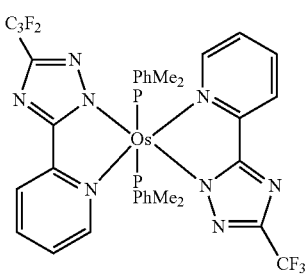

Os(hptz)₂(PPhMe₂)₂

Also, the dopant may be represented by Formula 100:

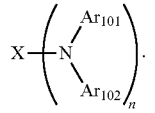

<Formula 100>

In Formula 100, X is selected from a substituted or unsubstituted $C_9$-$C_{10}$ cycloalkylene group, a substituted or unsubstituted $C_9$-$C_{10}$ cycloalkenylene group, and a substituted or unsubstituted $C_9$-$C_{60}$ arylene group; $Ar_{101}$ and $Ar_{102}$ are each independently selected from a substituted or unsubstituted $C_6$-$C_{30}$ aryl group and a substituted or unsubstituted $C_2$-$C_{30}$ heteroaryl group; and n is an integer of 2 to 4.

In one embodiment, in Formula 100, X may be selected from:
  i) an anthracenyl group, a chrysenyl group, a pyrenyl group, and a benzopyrenyl group; and
  ii) an anthracenyl group, a chrysenyl group, a pyrenyl group, and a benzopyrenyl group, each substituted with at least one selected from a deuterium atom, a fluorine atom, a cyano group, a nitro group, a methyl group, an ethyl group, an n-propyl group, an iso-propyl group, an n-butyl group, a sec-butyl group, an iso-butyl group, and a tert-butyl group.

In another embodiment, in Formula 100, X may be selected from an anthracenyl group, a chrysenyl group, a pyrenyl group, and a benzopyrenyl group.

In another embodiment, in Formula 100, X may be a pyrenylene group.

In one embodiment, in Formula 100, $Ar_{101}$ and $Ar_{102}$ may each independently be selected from:
  i) a phenyl group, a naphthyl group, and a biphenyl group; and
  ii) a phenyl group, a naphthyl group, and a biphenyl group, each substituted with at least one selected from a deuterium atom, a fluorine atom, a cyano group, a nitro group, a methyl group, an ethyl group, an n-propyl group, an iso-propyl group, an n-butyl group, a sec-butyl group, an iso-butyl group, a tert-butyl group, and a phenyl group.

In another embodiment, in Formula 100, $Ar_{101}$ and $Ar_{102}$ may each independently be selected from:
  i) a phenyl group and a biphenyl group; and
  ii) a phenyl group and a biphenyl group, each substituted with at least one selected from a fluorine atom, a methyl group, and a phenyl group.

In one embodiment, in Formula 100, n may be 2.

In some embodiments, a compound represented by Formula 100 may be one selected from Compounds 101 to 109:

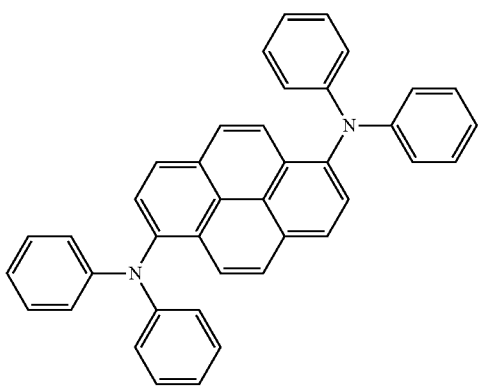

101

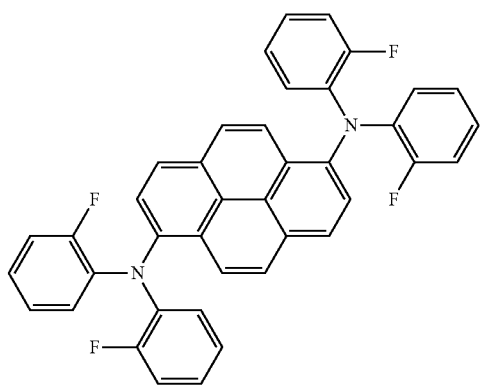

102

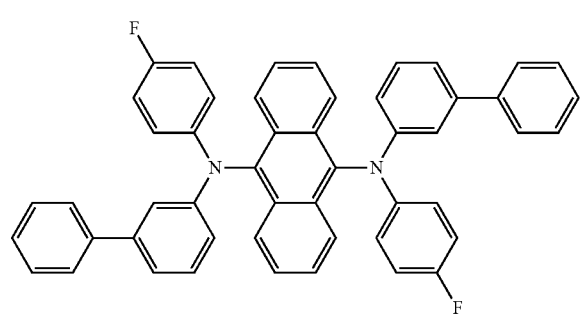

103

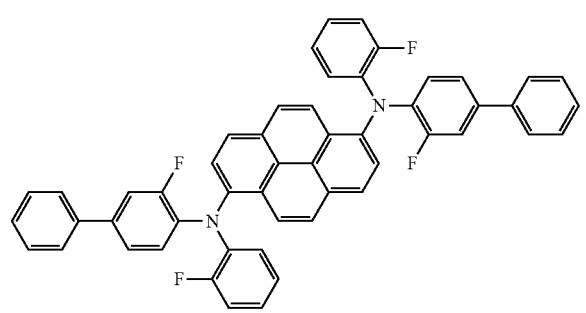

104

105

106

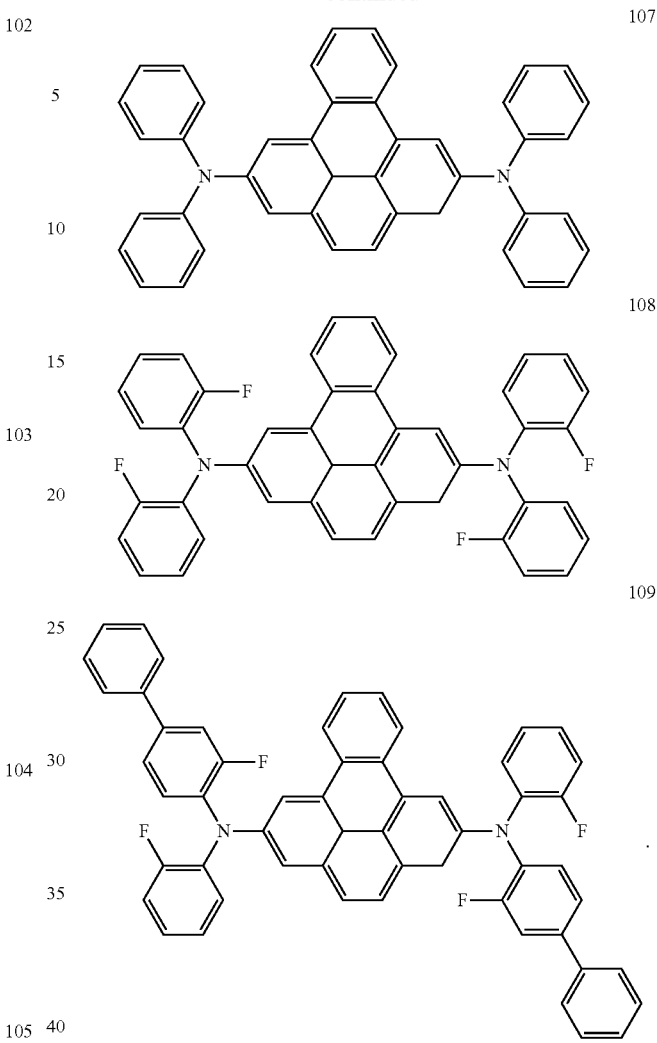

107

108

109

When the EML 133 includes a host and a dopant, an amount of the dopant in the EML 133 may be generally in the range of, for example, about 0.01 to about 15 wt % based on 100 wt % of the host.

A thickness of the EML 133 is in a range of about 200 Å to about 700 Å. Maintaining a thickness of the EML 133 within this range may help provide excellent light-emitting properties without a substantial increase in driving voltage.

When the OLED 100 is a full-color OLED, the EML 133 may be patterned as a red EML, a green EML, and a blue EML depending on a red pixel, a green pixel, and a blue pixel. In an embodiment, the indenopyridine-based compound represented by Formula 1 may be included in the blue EML as a host.

The EML 133 may have a multiple-layered structure, in which a red EML, a green EML, and a blue EML are stacked so as to emit white light, or the EML 133 may have a single-layered structure including all of a red light-emitting material, a green light-emitting material, and a blue light-emitting material. The OLED 100 including the EML 133 may emit light in full-color by further including a red color filter, a green color filter, and a blue color filter.

Next, the ETL 134 may be formed on the EML 133 by vacuum deposition, spin coating, or casting. When the ETL 134 is formed by vacuum deposition or spin coating, the deposition and coating conditions vary depending on a used compound, but generally the conditions may be about the same as the conditions for forming the HIL 131. Exemplary materials for forming the ETL include quinoline derivatives such as tris(8-quinolinolate)aluminum (Alq$_3$), 3-(biphenyl-4-yl)-5-(4-tert-butylphenyl)-4-phenyl-4H-1,2,4-triazole (TAZ), bis(2-methyl-8-quinolinolato-N1,O8)-(1,1'-biphenyl) (Balq), beryllium bis(benzoquinolin-10-olate) (Bebq$_2$), DNA, Compound 301, Compound 302, and Bphen:

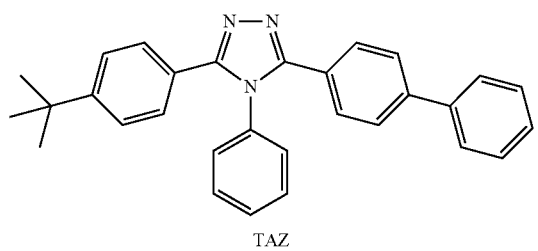

TAZ

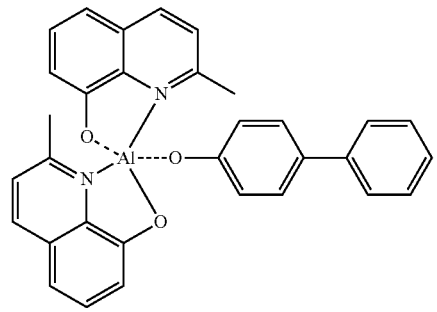

BAlq

<Compound 301>

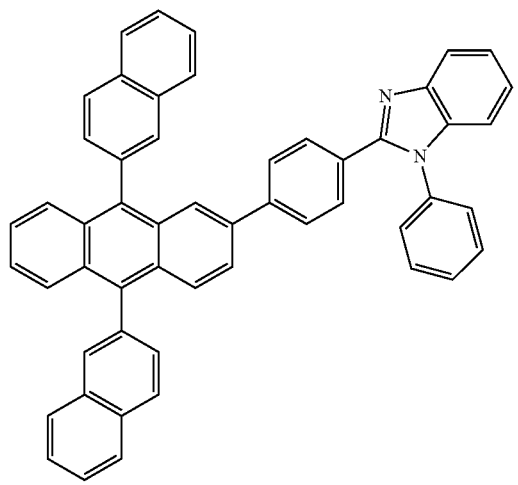

<Compound 302>

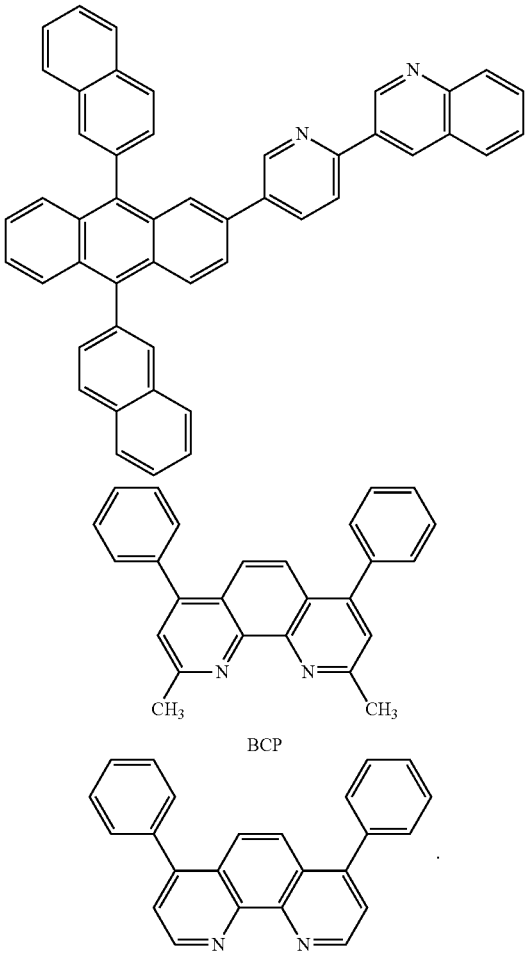

BCP

Bphen

A thickness of the ETL 134 may be in a range of about 100 Å to about 1,000 Å, for example, in a range of about 150 Å to about 500 Å. Maintaining a thickness of the ETL 134 within this range may help provide satisfactory electron transporting properties without a substantial increase in driving voltage.

The ETL 134 may further include a metal-containing material in addition to an electron transporting organic compound. The metal-containing material may include a Li-complex. Examples of the Li-complex may include a lithium quinolate (Liq) or Compound 203:

<Compound 203>

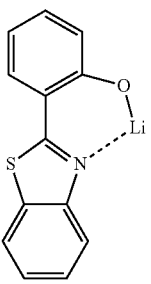

Also, the EIL 135, which facilitates electron injection from a cathode, may be formed on the ETL 134. Exemplary materials for forming the EIL 135 include LiF, NaCl, CsF, Li$_2$O, or BaO. The deposition condition of the EIL may vary according a used compound, but generally the condition may be about the same as the condition for forming the HIL 131.

A thickness of the EIL 135 may be in a range of about 1 Å to about 100 Å, for example, in a range of about 3 Å to about 90 Å. Maintaining a thickness of the EIL 135 within this range may help provide satisfactory electron injecting properties without a substantial increase in driving voltage.

The second electrode 140 is formed on the organic layer 130. The second electrode 140 may be a cathode, which is an electron injection electrode. In an embodiment, a metal for forming the second electrode 140 may include a metal having low work function, such as metal, an alloy, an electric conducting compound, and mixtures thereof. For example, the second electrode 140 may be formed as a thin film by using lithium (Li), magnesium (Mg), aluminum (Al), aluminum-lithium (Al—Li), calcium (Ca), magnesium-indium (Mg—In), or magnesium-silver (Mg—Ag), and may be transparent. In order to obtain a top-emission type OLED, the second electrode 140 may be formed as a transparent electrode by using ITO or IZO.

Also, in an embodiment, a phosphorescent dopant is included in the EML 133, and a hole blocking layer (HBL) may be formed between the ETL 134 and the EML 133 or between the H-functional layer and the EML 133 by vacuum deposition, spin coating, casting or LB deposition to help prevent triplet excitons or holes from being diffused to the ETL 134. When the HBL is formed by vacuum deposition or spin coating, the conditions thereof may vary according to a used compound, but generally the conditions may be about the same as the condition for forming the HIL 131. Exemplary HBL materials include an oxadiazole deriative, a triazole derivative, and a phenanthroline derivative. For example, BCP may be used as a HBL material:

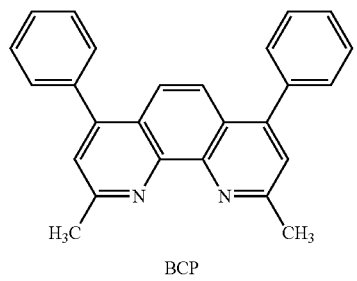 [SMILES: Cc1cc(-c2ccccc2)c2ccc3c(-c4ccccc4)cc(C)nc3c2n1 ; "BCP"]

BCP

A thickness of the HBL may be in a range of about 20 Å to about 1,000 Å, for example, in a range of about 30 Å to about 300 Å. Maintaining a thickness of the HBL is within this range may help provide excellent hole blocking properties without a substantial increase in driving voltage.

The OLED 100 has been described by referring to FIG. 1. Additional embodiments include omission of one or more of the layers illustrated in FIG. 1 (i.e., EIL, ETL, EML, HTL, and HIL), rearrangement of one or more of the layers illustrated in FIG. 1, and/or additional layers.

As used herein, examples of the unsubstituted $C_1$-$C_{60}$ alkyl group (or a $C_1$-$C_{60}$ alkyl group) include linear or branched $C_1$-$C_{60}$ alkyl groups such as methyl, ethyl, propyl, isobutyl, sec-butyl, pentyl, iso-amyl, hexyl, and the like. Examples of the substituted $C_1$-$C_{60}$ alkyl group include a group, in which at least one hydrogen in the unsubstituted $C_1$-$C_{60}$ alkyl group is substituted with one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group), each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluolenyl group, a dimethylfluolenyl group, a diphenylfluolenyl group, a carbazolyl group, a phenylcarbazolyl group, a pyridyl group, a pyrimidinyl group, a pyrazinyl group, a pyridazinyl group, a triazinyl group, a quinolyl group, and an isoquinolyl group; and —N($Q_{11}$)($Q_{12}$); and —Si($Q_{13}$)($Q_{14}$)($Q_{15}$) (here, $Q_{11}$ and $Q_{12}$ are each independently a $C_6$-$C_{60}$ aryl group or a $C_2$-$C_{60}$ heteroaryl group, and $Q_{13}$ to $Q_{15}$ are each independently a $C_1$-$C_{60}$ alkyl group, a $C_1$-$C_{60}$ alkoxy group, a $C_6$-$C_{60}$ aryl group, or $C_2$-$C_{60}$ heteroaryl group.

As used herein, the unsubstituted $C_1$-$C_{60}$ alkoxy group (or $C_1$-$C_{60}$ alkoxy group) has a formula of —OA (in this regard, A is the unsubstituted $C_1$-$C_{60}$ alkyl group as described above) and examples thereof include methoxy, ethoxy, isopropyloxy, and the like. At least one hydrogen atom of the unsubstituted $C_1$-$C_{60}$ alkoxy group may be substituted with the same substituent as in the substituted $C_1$-$C_{60}$ alkyl group described above.

As used herein, the unsubstituted $C_2$-$C_{60}$ alkenyl group (or $C_2$-$C_{60}$ alkenyl group) is interpreted to contain at least one carbon-carbon double bond in the center or at a terminal of the unsubstituted $C_2$-$C_{60}$ alkyl group. Examples of the unsubstituted $C_2$-$C_{60}$ alkenyl group include ethenyl, propenyl, butenyl, and the like. At least one hydrogen atom of the $C_2$-$C_{60}$ alkenyl group may be substituted with the same substituent as in the substituted $C_1$-$C_{60}$ alkyl group described above.

As used herein, the unsubstituted $C_2$-$C_{60}$ alkynyl group (or $C_2$-$C_{60}$ alkynyl group) is interpreted to contain at least one carbon-carbon triple bond in the center or at a terminal of the $C_2$-$C_{60}$ alkyl group defined above. Examples of the unsubstituted $C_2$-$C_{60}$ alkynyl group include ethynyl, propynyl, and the like. At least one hydrogen atom of the unsubstituted $C_2$-$C_{60}$ alkynyl group may be substituted with the same substituent as in the substituted $C_1$-$C_{60}$ alkyl group described above.

As used herein, the unsubstituted $C_3$-$C_{30}$ cycloalkyl group indicates a monovalent group of a saturated cyclic hydrocarbon having 3 to 30 carbons. Examples of the unsubstituted $C_3$-$C_{30}$ cycloalkyl group include a cyclopropyl group, a cyclobutyl group, a cyclopentyl group, a cyclohexyl group, and a cyclooctyl group. At least one hydrogen atom of the unsubstituted $C_3$-$C_{30}$ cycloalkyl group may be substituted with the same substituent as in the substituted $C_1$-$C_{60}$ alkyl group described above.

As used herein, the unsubstituted $C_3$-$C_{30}$ cycloalkenyl group indicates a ring-type unsaturated hydrocarbon group including at least one carbon-carbon double bond, but not an aromatic ring. Examples of the unsubstituted $C_3$-$C_{30}$ cycloalkenyl group include a cyclopropenyl group, a cyclobutenyl group, a cyclopentenyl group, a cyclohexenyl group, a cycloheptenyl group, a 1,3-cyclohexadienyl group, a 1,4-cyclohexadienyl group, a 2,4-cycloheptadienyl group, and a 1,5-cyclooctadienyl group. At least one hydrogen atom of the unsubstituted $C_3$-$C_{30}$ cycloalkenyl group may be substituted with the same substituent as in the substituted $C_1$-$C_{60}$ alkyl group described above.

As used herein, the unsubstituted $C_6$-$C_{60}$ aryl group indicates a monovalent group having an aromatic carbocyclic system that has 6 to 60 carbon atoms and at least one aromatic ring and the unsubstituted $C_6$-$C_{60}$ arylene group indicates a divalent group having an aromatic carbocyclic system that has 6 to 60 carbon atoms and at least one aromatic ring. If the $C_6$-$C_{60}$ aryl group and the $C_6$-$C_{60}$ arylene group each independently have two or more aromatic rings, the rings may be fused with each other. At least one hydrogen atom of each of the unsubstituted $C_6$-$C_{60}$ aryl group and the unsubstituted $C_6$-$C_{60}$ arylene group may be substituted with the same substituent as in the substituted $C_1$-$C_{60}$ alkyl group described above.

As used herein, examples of the substituted or unsubstituted $C_6$-$C_{60}$ aryl group include, but not limited to, a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- and p-fluorophenyl group, and a dichlorophenyl group), a dicyanophenyl group, a trifluoromethoxyphenyl group, an o-, m-, and p-tolyl group, an o-, m- and p-cumenyl group, a mesityl group, a phenoxyphenyl group, an (α,α-dimethylbenzene) phenyl group, a (N,N'-dimethyl)aminophenyl group, a (N,N'-diphenyeaminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolinyl group, a methylanthracenyl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coroneryl group, a trinaphthylenyl group, a heptaphenyl group, a heptacenyl, a pyranthrenyl group, and an ovalenyl group. Examples of the substituted $C_6$-$C_{60}$ aryl group may be easily understood with reference to the examples of the unsubstituted $C_6$-$C_{60}$ aryl group described above and the substituents of the substituted $C_1$-$C_{60}$ alkyl group. Examples of the substituted or unsubstituted $C_6$-$C_{60}$ arylene group may be easily understood with reference to the substituted or unsubstituted $C_6$-$C_{60}$ aryl group described above.

As used herein, the unsubstituted $C_2$-$C_{60}$ heteroaryl group indicates a monovalent group having at least one aromatic ring system including carbon rings and at least one hetero atom selected from the group consisting of N, O, P, and S as a ring-forming atom, and the unsubstituted $C_2$-$C_{60}$ heteroarylene group indicates a divalent group having at least one aromatic ring system including carbon rings and at least one hetero atom selected from the group consisting of N, O, P, and S. In this regard, if the $C_2$-$C_{60}$ heteroaryl group and the $C_2$-$C_{60}$ heteroarylene group each independently have two or more aromatic rings, the rings may be fused with each other. At least one hydrogen atom of each of the unsubstituted $C_2$-$C_{60}$ heteroaryl group and the unsubstituted $C_2$-$C_{60}$ heteroarylene group may be substituted with the same substituents as in the $C_1$-$C_{60}$ alkyl group described above.

As used herein, examples of the unsubstituted $C_2$-$C_{60}$ heteroaryl group include, but not limited to, a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, and an imidazopyrimidinyl group. Examples of the unsubstituted $C_2$-$C_{60}$ heteroarylene group may be easily understood with reference to the examples of the substituted or unsubstituted $C_2$-$C_{60}$ arylene group.

The substituted or unsubstituted $C_6$-$C_{60}$ aryloxy group has a formula of —$OA_2$, wherein $A_2$ is the substituted or unsubstituted $C_6$-$C_{60}$ aryl group as described above, and the substituted or unsubstituted $C_6$-$C_{60}$ arylthio group has a formula of —$SA_3$, wherein $A_3$ is the substituted or unsubstituted $C_6$-$C_{60}$ aryl group described above.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthesis Example 1

Synthesis of Compound 1

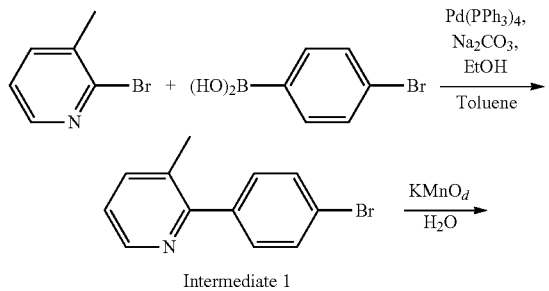

Intermediate 1

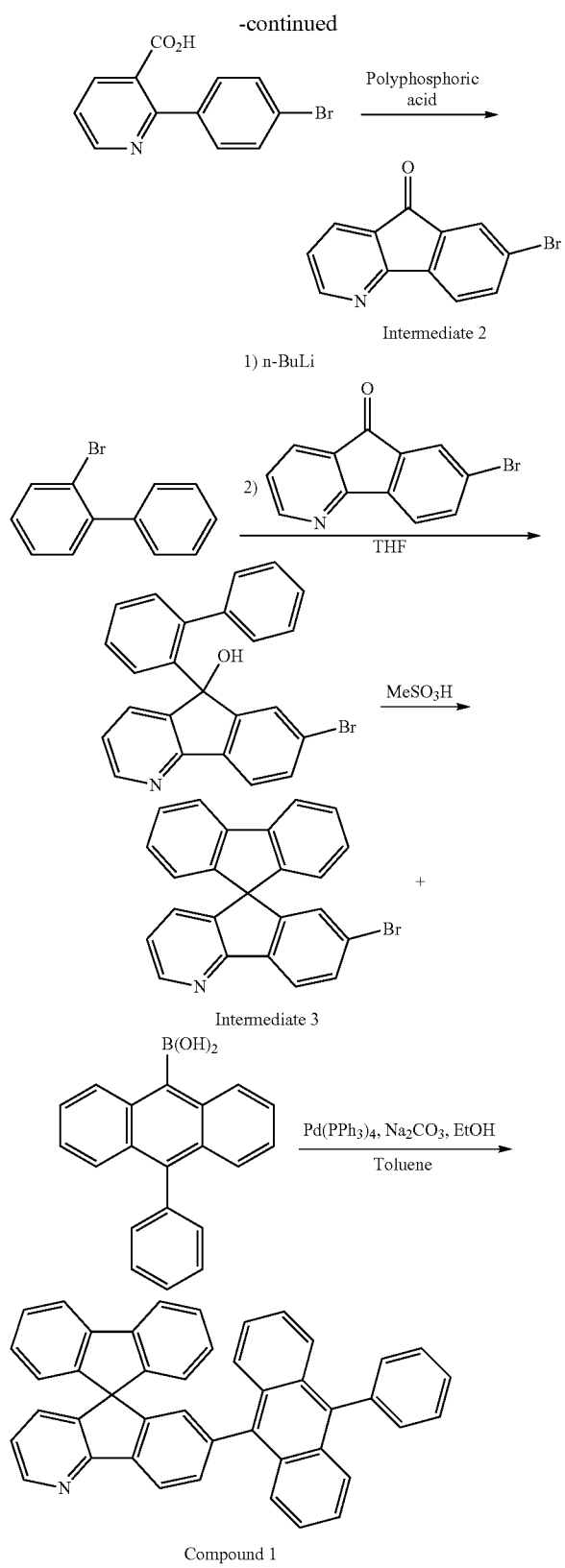

Synthesis of Intermediate 1

5 g (1 eq, 29.06 mmol) of 2-bromo-3-methylpyridine, 6.12 g (1.05 eq, 30.52 mmol) 4-bromophenylboronic acid, and 1.34 g (0.04 eq, 1.16 mmol) of tetrakis(triphenylphosphine)palladium(0) (Pd(PPh$_3$)$_4$) were put into a reaction flask and vacuum-dried, and the flask was filled with nitrogen gas. 72 ml of toluene was added into the reaction flask to dissolve the compounds. Then, 36 ml of ethanol and 36 ml (2.5 eq, 72.65 mmol) of 2.0 M sodium carbonate aqueous solution were added thereto, and the mixture was stirred while refluxing at a temperature of 120° C. for 3 hours. After the reaction was completed, the resultant solution was washed with distilled water, and an organic layer was extracted and collected using ethyl acetate. The collected anhydrous organic layer was dried by using anhydrous sulfur magnesium, and the solvent was removed therefrom by distillation under reduced pressure. The residue obtained therefrom was purified through a silica gel column chromatography to obtain 4.5 g (yield: 60%) of Intermediate 1. Intermediate 1 was confirmed by using NMR and APCI-MS.

$^1$H-NMR δ(ppm): 8.50(d, 1H), 7.60(d, 3H), 7.42(td, 2H), 7.19(d, 1H), 2.32(s, 3H)

APCI-MS (m/z): 248[M$^+$]

Synthesis of Intermediate 2

5.88 g (1 eq, 21.14 mmol) of 2-(4-bromophenyl)nicotinic acid, which was quantitatively obtained by reacting Intermediate 1 with a KMnO$_4$ aqueous solution, was put into a reaction flask, and 30 g of polyphosphoric acid was added thereto. After the reaction was completed, the resulting solution was added into a beaker containing 5 N sodium hydroxide aqueous solution, stirred at room temperature, and filtered the mixture to obtain 3.3 g (yield: 60%) of Intermediate 2 as a yellow solid. Intermediate 2 was confirmed by using NMR and APCI-MS.

$^1$H-NMR δ(ppm): 7.92(d, 1H), 7.86(s, 1H), 7.74(d, 2H), 7.25(d, 1H)

APCI-MS (m/z): 260[M$^+$]

Synthesis of Intermediate 3

3.29 g (1 eq, 14.09 mmol) of 2-bromobiphenyl was put into a reaction flask and dissolved with 150 ml of THF. 4.67 ml (14.09 eq, 8.78 mmol) of 1.6 M n-BuLi was slowly and added drop wise to the reaction flask at a temperature of −78° C. After stirring at a temperature of −78° C. for 30 minutes, 3.3 g (0.9 eq, 12.69 mmol) of Intermediate 2 was added thereto, and then stirred at room temperature for 5 minutes. After the reaction was completed, the resultant solution was washed with distilled water, and an organic layer was extracted and collected using ethyl acetate. The residue obtained from the collected organic layer by removing the solvent was put into a flask, and 5 ml of MeSO$_3$H was slowly and added drop wise thereto. The reaction solution was extracted with ethyl acetate, and an organic layer was collected. The collected anhydrous organic layer was dried by using anhydrous sulfur magnesium, and the solvent was removed therefrom by distillation under reduced pressure. The residue obtained therefrom was purified through a silica gel column chromatography to obtain 3.4 g (yield: 70%) of Intermediate 3. Intermediate 2 was confirmed by using NMR and APCI-MS.

$^1$H-NMR δ(ppm): 8.59(t, 1H), 8.00(d, 1H), 7.85(d, 2H), 7.57(dd, 1H), 7.41(t, 2H), 7.17(t, 2H), 7.06(d, 2H), 6.90(s, 1H), 6.74(d, 2H)

APCI-MS (m/z): 396[M$^+$]

Synthesis of Compound 1

3.4 g (1 eq, 8.57 mmol) of Intermediate 3, 2.81 g (1.03 eq, 9.43 mmol) of 9-phenylanthracen-10-ylboronic acid, and 396 mg (0.04 eq, 0.343 mmol) Pd(PPh$_3$)$_4$ were put into a reaction flask and vacuum-dried, and the flask was filled with nitrogen gas. 40 ml of toluene was added into the reaction flask to dissolve the compounds. Then, 15 ml of ethanol and 15 ml (2.5 eq, 21.4 mmol) of 2.0 M sodium carbonate aqueous solution were added thereto, and the mixture was stirred while refluxing at a temperature of 120° C. for 3 hours. After the reaction was completed, the resultant solution was washed with distilled water, and an organic layer was extracted and collected using ethyl acetate. The collected anhydrous organic layer was dried by using anhydrous sulfur magnesium, and the solvent was removed therefrom by distillation under reduced pressure. The residue obtained therefrom was purified through a silica gel column chromatography to obtain 3.8 g (yield: 78%) of Compound 1. Compound 1 was confirmed by using ¹H-NMR and APCI-MS.

¹H-NMR δ(ppm): 8.68(d, 1H), 8.39(d, 1H), 7.75(d, 2H), 7.58(m, 10H), 7.47(d, 1H), 7.34(m, 4H), 7.24(d, 2H), 7.15 (m, 4H), 6.87(m, 2H)

APCI-MS (m/z): 569[M⁺]

Synthesis Example 2

Synthesis of Compound 2

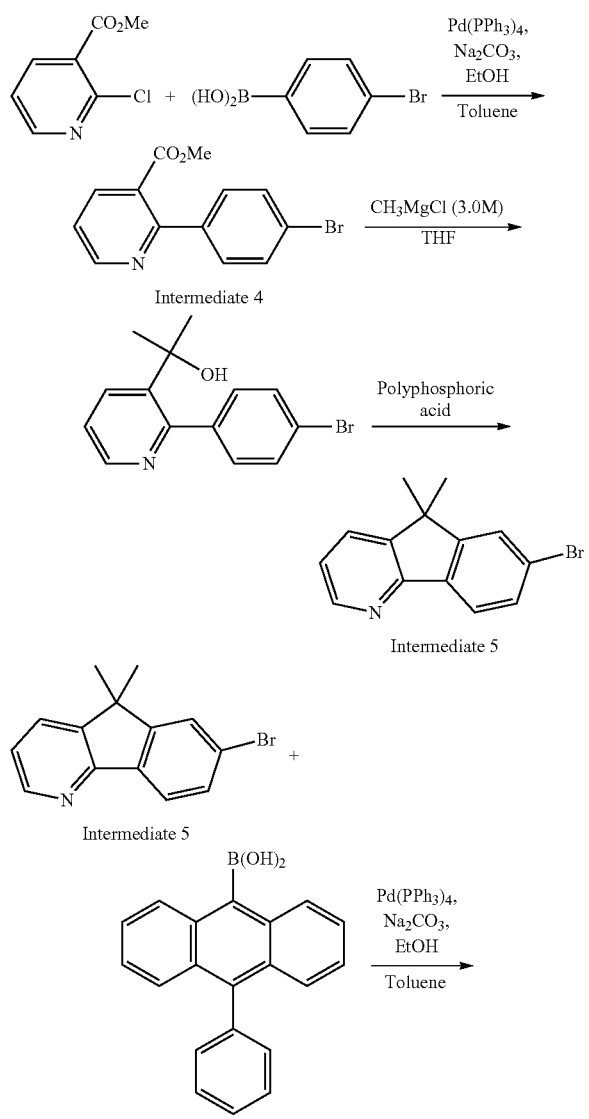

Intermediate 4

Intermediate 5

Intermediate 5

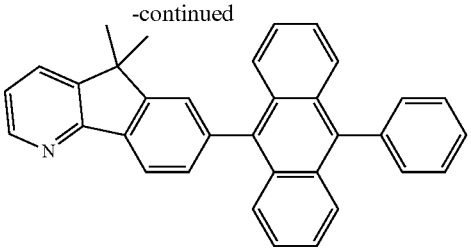

Compound 2

Synthesis of Intermediate 4

2.83 g (1 eq, 29.06 mmol) of methyl 2-chloronicotinate, 6.12 g (1.05 eq, 30.52 mmol) of 4-bromophenylboronic acid, and 1.34 g (0.04 eq, 1.16 mmol) of Pd(PPh₃)₄ were put into a reaction flask and vacuum-dried, and the flask was filled with nitrogen gas. 72 ml of toluene was added into the reaction flask to dissolve the compounds. Then, 36 ml of ethanol and 36 ml (2.5 eq, 72.65 mmol) of 2.0 M sodium carbonate aqueous solution were added thereto, and the mixture was stirred while refluxing at a temperature of 120° C. for 3 hours. After the reaction was completed, the resultant solution was washed with distilled water, and an organic layer was extracted and collected using ethyl acetate. The collected anhydrous organic layer was dried by using anhydrous sulfur magnesium, and the solvent was removed therefrom by distillation under reduced pressure. The residue obtained therefrom was purified through a silica gel column chromatography to obtain 3.37 g (yield: 60%) of Intermediate 4. Intermediate 4 was confirmed by using ¹H-NMR and APCI-MS.

¹H-NMR δ(ppm): 8.78(dd, 1H), 8.12(dd, 1H), 7.58(d, 2H), 7.42(d, 2H), 7.34(d, 1H)

APCI-MS (m/z): 292[M⁺]

Synthesis of Intermediate 5

3.37 g (1 eq, 11.54 mmol) of Intermediate 4 was put into a reaction flask and vacuum-dried, and the flask was filled with nitrogen gas. 100 ml of THF was added thereto, and then 9.6 ml (2.5 eq, 28.84 mmol) of 3.0 M methylmagnesium chloride (CH₃MgCl) was slowly and added drop wise thereto. After the reaction was completed, the reaction solution was extracted with ethyl acetate, and an organic layer was collected. The collected anhydrous organic layer was dried by using anhydrous sulfur magnesium, and the solvent was removed therefrom by distillation under reduced pressure. The residue obtained therefrom was put into a flask, 30 g of polyphosphoric acid was added thereto, and then the mixture was stirred while refluxing at a temperature of 190° C. After the reaction was completed, the reaction solution was extracted with ethyl acetate, and an organic layer was collected. The collected anhydrous organic layer was dried by using anhydrous sulfur magnesium, and the solvent was removed therefrom by distillation under reduced pressure. The obtained residue was purified through a silica gel column chromatography to obtain 1.6 g (yield: 70%) of Intermediate 5. Intermediate 5 was confirmed by using ¹H-NMR and APCI-MS.

¹H-NMR δ(ppm): 8.56(d, 1H), 7.88(d, 1H), 7.72(d, 1H), 7.62(s, 1H), 7.56(dd, 1H), 7.22(dd, 1H), 1.50(s, 6H)

APCI-MS (m/z): 274[M⁺]

Synthesis of Compound 2

1.6 g (1 eq, 5.83 mmol) of Intermediate 5, 1.91 g (1.1 eq, 6.42 mmol) of 9-phenylanthracen-10-ylboronic acid, and 270 mg (0.04 eq, 0.23 mmol) of Pd(PPh₃)₄ were put into a reaction flask and vacuum-dried, and the flask was filled with nitrogen gas. 20 ml of toluene was added into the reaction flask to dissolve the compounds. Then, 9 ml of ethanol and 9 ml (3 eq, 17.5 mmol) of 2.0 M sodium carbonate aqueous solution were added thereto, and the mixture was stirred while refluxing at a temperature of 120° C. for 3 hours. After the reaction was completed, the resultant solution was washed with distilled water, and an organic layer was extracted and collected using ethyl acetate. The collected anhydrous organic layer was dried by using anhydrous sulfur magnesium, and the solvent was removed therefrom by distillation under reduced pressure. The residue obtained therefrom was purified through a silica gel column chromatography to obtain 1.7 g (yield: 65%) of Compound 2. Compound 2 was confirmed by using $^1$H-NMR and APCI-MS.

$^1$H-NMR δ(ppm): 8.64(dd, 1H), 8.27(d, 1H), 7.73(m, 5H), 7.55(m, 7H), 736 (m, 4H), 7.27(t, 1H), 1.54(s, 6H)

APCI-MS (m/z): 447[M$^+$]

Synthesis Example 3

Synthesis of Compound 3

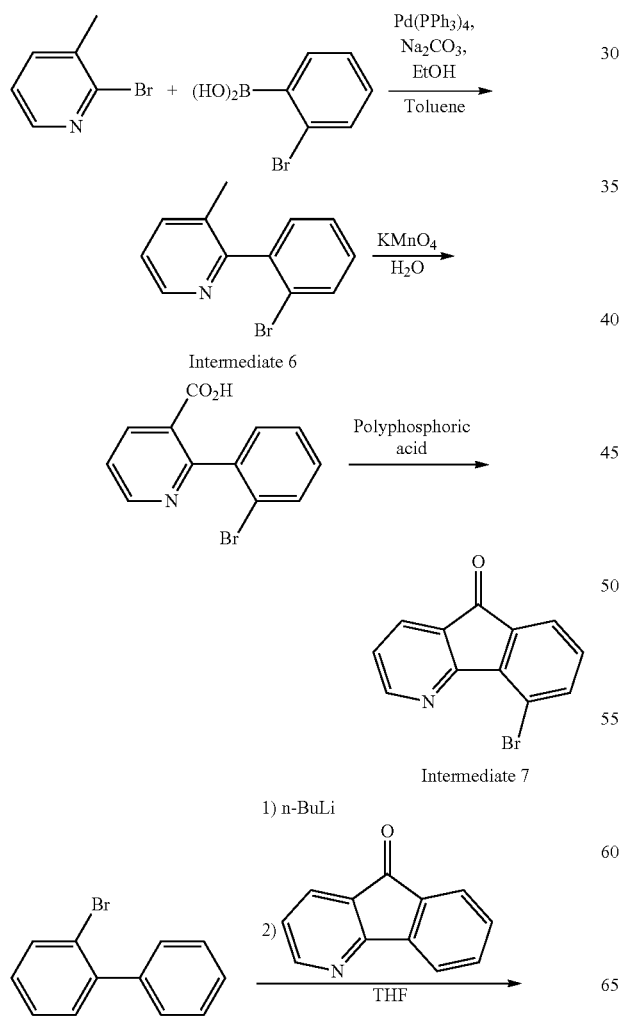

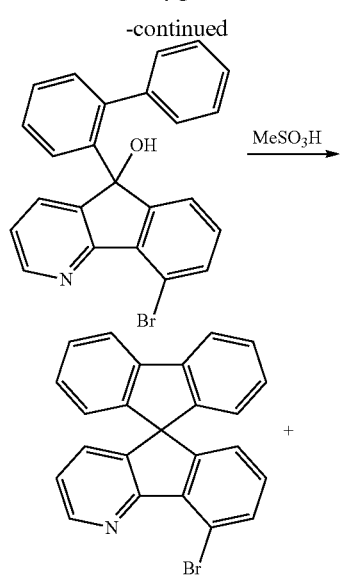

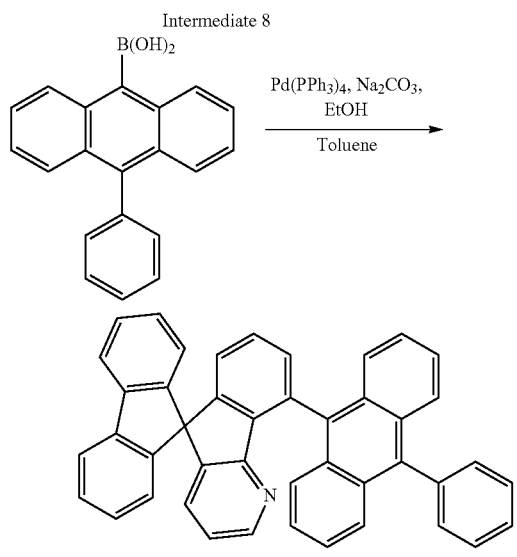

Synthesis of Intermediate 6

Intermediate 6 was synthesized in the same manner as in the synthesis of Intermediate 1, except that 2-bromophenyl boronic acid was used instead of 4-bromobiphenyl. Intermediate 6 was confirmed by using $^1$H-NMR and APCI-MS.

$^1$H-NMR δ(ppm): 8.53(d, 1H), 7.67(d, 1H), 7.60(d, 1H), 7.40(t, 1H), 7.29(m, 2H), 7.22(m, 1H), 2.16(s, 3H)

APCI-MS (m/z): 248[M$^+$]

Synthesis of Intermediate 7

3 g (yield: 89%) of Intermediate 7 was synthesized in the same manner as in the synthesis of Intermediate 2, except that Intermediate 6 was used instead of Intermediate 1. Intermediate 7 was confirmed by using $^1$H-NMR and APCI-MS.

$^1$H-NMR δ(ppm): 8.80(dd, 1H), 7.94(d, 1H), 7.76(d, 1H), 7.72(d, 1H), 7.29(m, 2H)

APCI-MS (m/z): 260[M$^+$]

Synthesis of Intermediate 8

2.6 g (yield: 90%) of Intermediate 8 was synthesized in the same manner as in the synthesis of Intermediate 3, except that Intermediate 7 was used instead of Intermediate 2. Intermediate 8 was confirmed by using $^1$H-NMR and APCI-MS.

¹H-NMR δ(ppm): 8.76(d, 1H), 7.85(d, 2H), 7.60(d, 1H), 7.40(t, 214), 7.15(t, 2H), 7.08(m, 3H), 6.70(t, 3H)

APCI-MS (m/z): 396[M⁺]

Synthesis of Compound 3

1.72 g (yield: 61%) of Compound 3 was synthesized in the same manner as in the synthesis of Compound 1, except that Intermediate 8 was used instead of Intermediate 3. Compound 3 was confirmed by using ¹H-NMR and APCI-MS.

¹H-NMR δ(ppm): 7.90(d, 2H), 7.85(dd, 1H), 7.78(m, 4H), 7.64(m, 5H), 7.42(t, 2H), 7.38(m, 6H), 7.22(d, 2H), 6.94(m, 4H), 6.68(dd, 1H)

APCI-MS (m/z): 569[M⁺]

Synthesis Example 4

Synthesis of Compound 4

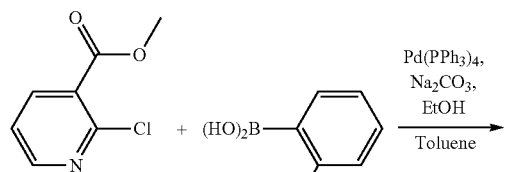

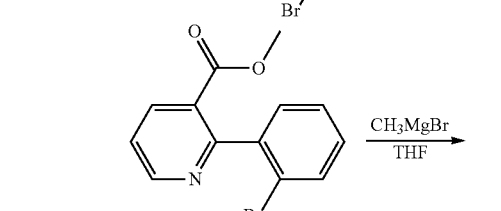

Intermediate 9

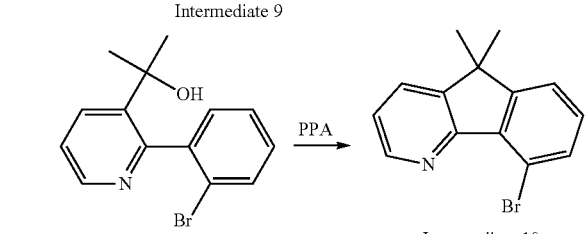

Intermediate 10

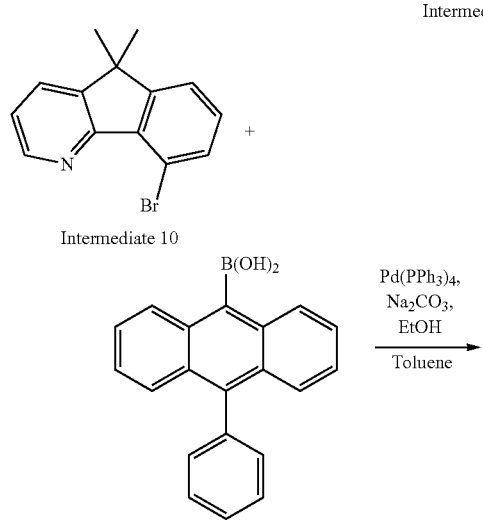

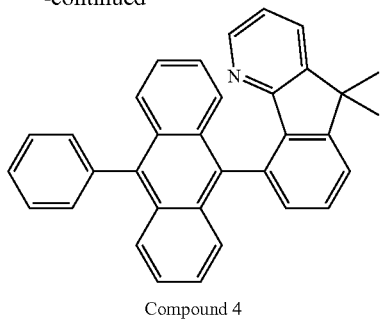

Compound 4

Synthesis of Intermediate 9

3.25 g (yield: 47%) of Intermediate 9 was synthesized in the same manner as in the synthesis of Intermediate 4, except that 2-bromophenyl boronic acid was used instead of 4-bromobiphenyl boronic acid. Intermediate 9 was confirmed by using ¹H-NMR and APCI-MS.

¹H-NMR δ(ppm): 8.83(d, 1H), 8.35(d, 1H), 7.63(d, 1H), 7.45-7.38(m, 3H), 7.29(d, 1H), 3.71(s, 3H)

APCI-MS (m/z): 292[M⁺]

Synthesis of Intermediate 10

1.13 g (yield: 60%) of Intermediate 10 was synthesized in the same manner as in the synthesis of Intermediate 5, except that Intermediate 9 was used instead of Intermediate 4, and CH₃MgBr was used instead of CH₃MgCl. Intermediate 10 was confirmed by using ¹H-NMR and APCI-MS.

¹H-NMR δ(ppm): 8.73(dd, 1H), 7.74(dd, 1H), 7.60(dd, 1H), 7.45(dd, 1H), 7.29-7.23(m, 2H), 1.48(s, 6H)

APCI-MS (m/z): 274[M⁺]

Synthesis of Compound 4

1.82 g (yield: 76%) of Compound 4 was synthesized in the same manner as in the synthesis of Compound 2, except that Intermediate 10 was used instead of Intermediate 5. Compound 4 was confirmed by using ¹H-NMR and APCI-MS.

¹H-NMR δ(ppm): 7.82(dd, 1H), 7.74(d, 2H), 7.70-7.50 (m, 10H), 7.34-7.16 (m, 5H), 6.88(dd, 1H), 1.64(s, 6H)

APCI-MS (m/z): 447[M⁺]

Example 1

As an anode, a 15 Ω/cm² (1200 Å) ITO glass substrate was cut to a size of 50 mm×50 mm×0.7 mm, washed with ultrasonic waves in isopropyl alcohol and pure water for 5 minutes each, and then cleaned with UV for 30 minutes and ozone for 10 minutes. The ITO glass substrate was mounted on a vacuum depositor.

4,4',4''-tris[2-naphthyl(phenyl)amino]triphenylamine (2-TNATA) was deposited on the ITO glass substrate to form a HIL having a thickness of 600 Å and 4,4'-bis[N-(1-naphthyl)-N-phenylamino]biphenyl (NPB) was then deposited on the HIL to form a HTL having a thickness of 300 Å.

Then, Compound 1 (as a host) and Compound 102 (as a dopant) were co-deposited on the HTL at a weight ratio of 95:5 to form an EML having a thickness of 200 Å.

Then, Compound 201 was vacuum-deposited on the EML to form an ETL having a thickness of 300 Å, LiF was deposited on the ETL to form an EIL having a thickness of 10 Å, and Al was deposited on the EIL to form a cathode having a thickness of 3,000 Å, thereby completing the manufacture of an OLED.

<Compound 201>

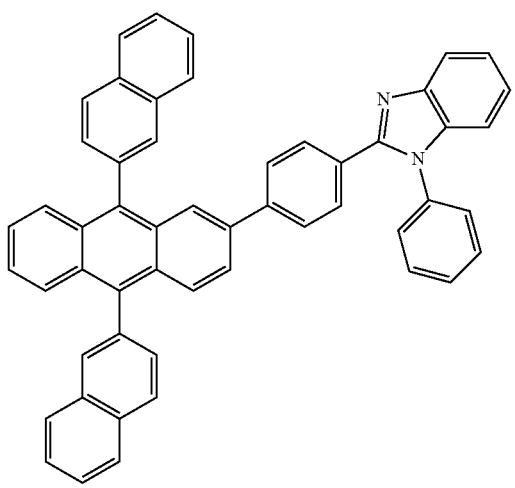

Example 2

An OLED was manufactured in the same manner as in Example 1, except that Compound 2 was used instead of Compound 1 in the formation of the EML.

Example 3

An OLED was manufactured in the same manner as in Example 1, except that Compound 3 was used instead of Compound 1 in the formation of the EML.

Example 4

An OLED was manufactured in the same manner as in Example 1, except that Compound 4 was used instead of Compound 1 in the formation of the EML.

Comparative Example 1

An OLED was manufactured in the same manner as in Example 1, except that 9,10-di(naphthalen-2-yl)anthracene (ADN) was used instead of Compound 1 in the formation of the EML.

Comparative Example 2

An OLED was manufactured in the same manner as in Example 1, except that Compound X was used instead of Compound 102 in the formation of the EML.

<Compound X>

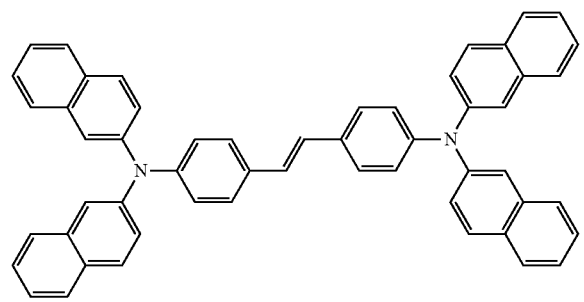

Comparative Example 3

An OLED was manufactured in the same manner as in Example 1, except that Compound A was used instead of Compound 1 in the formation of the EML.

<Compound A>

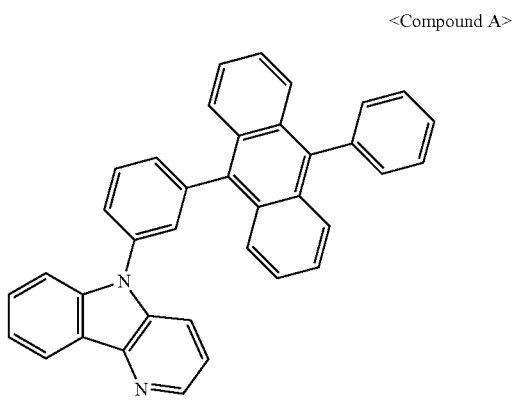 [SMILES: c1ccc(-c2c3ccccc3c(-c3cccc(-n4c5ccccc5c5ncccc54)c3)c3ccccc23)cc1]

Comparative Example 4

An OLED was manufactured in the same manner as in Example 1, except that Compound B was used instead of Compound 1 in the formation of the EML.

<Comopund B>

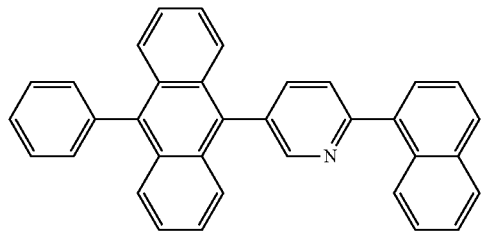

Evaluation Example

Driving voltage, brightness, and efficiency of the OLEDs of Examples 1 through 4 and Comparative Examples 1 through 4 were evaluated using a current-voltmeter, Kethley SMU 236 (available from PhotoResearch), to apply a voltage to the OLEDs, and the results are shown in Table 1 below.

TABLE 1

| | Host material | Dopant material | Driving voltage (V) | Brightness (cd/m$^2$) | Efficiency (cd/A) |
|---|---|---|---|---|---|
| Example 1 | Compound 1 | Compound 102 | 3.8 | 456 | 4.56 |
| Example 2 | Compound 2 | Compound 102 | 3.6 | 438 | 4.38 |
| Example 3 | Compound 3 | Compound 102 | 3.5 | 432 | 4.32 |
| Example 4 | Compound 4 | Compound 102 | 3.7 | 428 | 4.28 |
| Comparative Example 1 | ADN | Compound 102 | 4.4 | 328 | 3.28 |

TABLE 1-continued

| | Host material | Dopant material | Driving voltage (V) | Brightness (cd/m$^2$) | Efficiency (cd/A) |
|---|---|---|---|---|---|
| Comparative Example 2 | Compound 1 | Compound X | 4.3 | 346 | 3.46 |
| Comparative Example 3 | Compound A | Compound 102 | 4.5 | 352 | 3.52 |
| Comparative Example 4 | Compound B | Compound 102 | 4.2 | 363 | 3.63 |

Referring to Table 1, the OLEDs of Examples 1 through 4 exhibit excellent driving voltage, high brightness, and higher efficiency, as compared to the OLEDs of Comparative Examples 1 through 4.

By way of summation and review, an OLED structure may include a substrate, an anode, a hole transport layer (HTL), an emission layer (EML), an electron transport layer (ETL), and a cathode, which are sequentially stacked on the substrate. The HTL, the EML, and the ETL are organic layers formed of organic compounds.

When a voltage is applied between the anode and the cathode, holes injected from the anode move to the EML via the HTL, and electrons injected from the cathode move to the EML via the ETL. The holes and electrons are recombined with each other in the EML to generate excitons. Then, the excitons are transitioned from an excited state to a ground state, thereby generating light.

As described above, according to one or more embodiments, an OLED of high quality may be provided.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An indenopyridine-based compound represented by Formula 1:

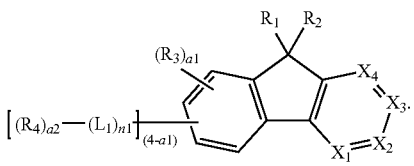

<Formula 1> wherein, in Formula 1,
$X_1$ is a nitrogen atom (N) or $C(R_{11})$; $X_2$ is N or $C(R_{12})$; $X_3$ is N or $C(R_{13})$; $X_4$ is N or $C(R_{14})$; wherein only one of $X_1$ to $X_4$ is N;
$L_1$ is selected from:
i) an anthracenylene group, a chrysenylene group, and a pyrenylene group; and ii) an anthracenylene group, a chrysenylene group, and a pyrenylene group, each substituted with at least one selected from:
a deuterium atom, a halogen atom, a hydroxyl group, a cyano group, a nitro group, a methyl group, an ethyl group, an n-propyl group, an iso-propyl group, an n-butyl group, a sec-butyl group, an iso-butyl group, and a tert-butyl group;
a phenyl group, a naphthyl group, a pyridyl group, and a triazinyl group; and
a phenyl group, a naphthyl group, a pyridyl group, and a triazinyl group, each substituted with at least one selected from a deuterium atom, a halogen atom, a hydroxyl group, a cyano group, a nitro group, a methyl group, an ethyl group, an n-propyl group, an iso-propyl group, an n-butyl group, a sec-butyl group, an iso-butyl group, and a tert-butyl group;
n1 is 1, 2, or 3;
$R_1$ and $R_2$ are each independently selected from a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, and a substituted or unsubstituted $C_2$-$C_{30}$ heteroaryl group, wherein $R_1$ and $R_2$ are optionally connected to each other to form a substituted or unsubstituted $C_6$-$C_{20}$ saturated ring or a substituted or unsubstituted $C_6$-$C_{20}$ unsaturated ring;
$R_{11}$ to $R_{14}$, $R_3$, and $R_4$ are each independently selected from a hydrogen atom, a deuterium atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, and a substituted or unsubstituted $C_6$-$C_{30}$ arylthio group; and
a1 and a2 are each independently selected from an integer of 0, 1, 2 and 3.

2. The indenopyridine-based compound as claimed in claim 1, wherein:
$L_1$ is selected from an anthracenylene group, a chrysenylene group, and a pyrenylene group.

3. The indenopyridine-based compound as claimed in claim 1, wherein n1 is an integer of 1 or 2.

4. The indenopyridine-based compound as claimed in claim 1, wherein:
a moiety represented by $(L_1)_{n1}$ is one selected from Formulae 3-1 to 3-4:

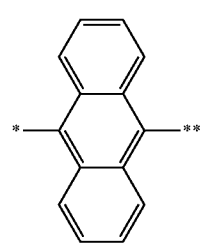

3-1

-continued

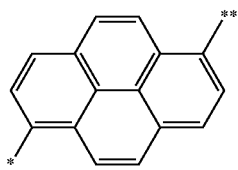
3-2

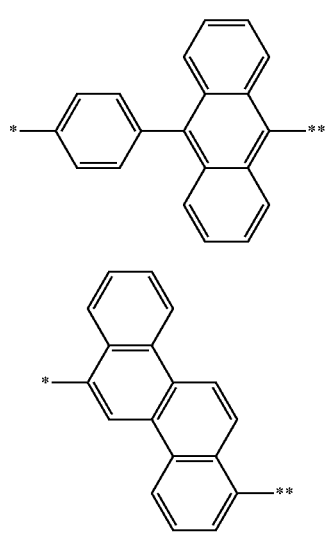
3-3

3-4 wherein, in Formulae 3-1 to 3-4,
\* is a binding site with $R_4$, and
\*\* is a binding site with an indenopyridine ring portion of Formula 1.

5. The indenopyridine-based compound as claimed in claim 1, wherein $R_1$ and $R_2$ are a phenyl group, or $R_1$ and $R_2$ combined are Formula 5:

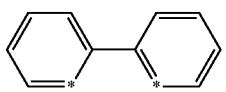
<Formula 5> wherein, in Formula 5,
\* is a binding site with an indenopyridine ring.

6. The indenopyridine-based compound as claimed in claim 1, wherein $R_{11}$ to $R_{14}$, and $R_3$ are each independently selected from a hydrogen atom, a deuterium atom, a fluorine atom, a cyano group, a nitro group, and a methyl group.

7. The indenopyridine-based compound as claimed in claim 1, wherein:
a2 is 1, 2, or 3, and
$R_4$ is selected from:
i) a phenyl group, a naphthyl group, and an anthryl group; and
ii) a phenyl group, a naphthyl group, and an anthryl group, each substituted with at least one selected from a hydrogen atom, a deuterium atom, a halogen atom, a hydroxyl group, a cyano group, a nitro group, a methyl group, an ethyl group, an n-propyl group, an iso-propyl group, a tert-butyl group, a phenyl group, a naphthyl group, and an anthryl group.

8. The indenopyridine-based compound as claimed in claim 1, wherein:

a2 is 1, 2, or 3, and
$R_4$ is selected from a phenyl group, a 1-naphthyl group, and a 2-naphthyl group.

9. The indenopyridine-based compound as claimed in claim 1, wherein a2 is an integer of 0 or 1.

10. The indenopyridine-based compound as claimed in claim 1, wherein:
a2 is 1; and
a1 is 3.

11. The indenopyridine-based compound as claimed in claim 1, wherein the indenopyridine-based compound is represented by Formula 1a:

<Formula 1a>

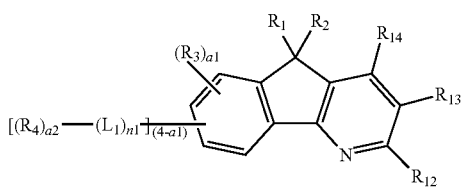

wherein, in Formula 1a,
a moiety represented by $(L_1)_{n1}$ is one selected from Formulae 3-1 to 3-4:

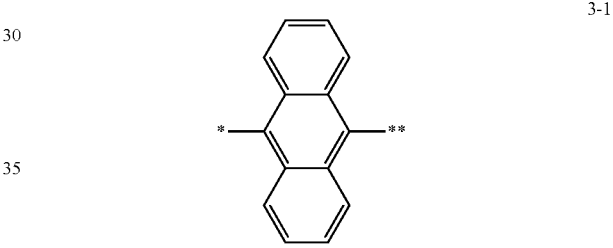
3-1

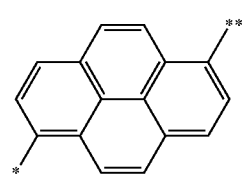
3-2

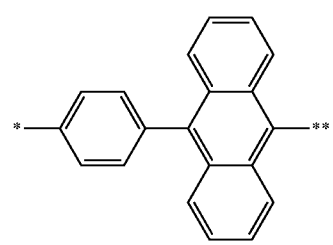
3-3

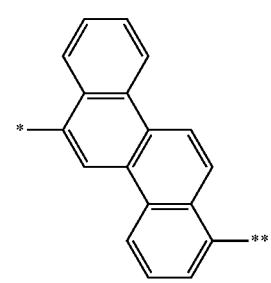
3-4 wherein, in Formulae 3-1to 3-4,

\* is a binding site with $R_4$, and

\*\* is a binding site with an indenopyridine ring portion of Formula 1a;

$R_1$ and $R_2$ are a phenyl group, or $R_1$ and $R_2$ combined are Formula 5:

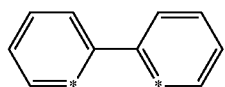

<Formula 5> wherein, in Formula 5,

\* is a binding site with an indenopyridine ring;

$R_3$ and $R_{12}$ to $R_{14}$ are each independently selected from a hydrogen atom, a deuterium atom, a fluorine atom, a cyano group, a nitro group, and a methyl group;

$R_4$ is selected from a phenyl group, a 1-naphthyl group, and a 2-naphthyl group;

a1 is 3; and a2 is an integer of 0 or 1.

12. The indenopyridine-based compound as claimed in claim 1, wherein the indenopyridine-based compound is represented by one of Formulae 1b to 1e:

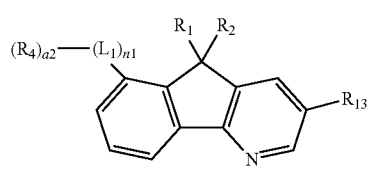

<Formula 1b>

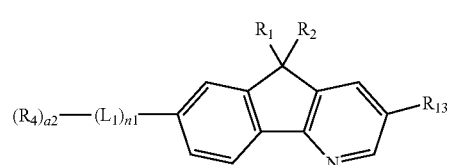

<Formula 1c>

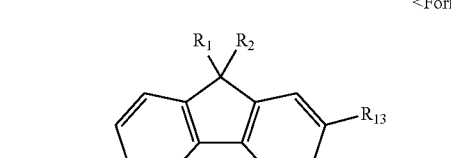

<Formula 1d>

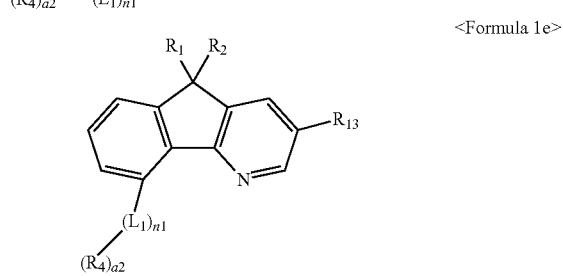

<Formula 1e> wherein, in Formulae 1b to 1e, a moiety represented by $(L_1)_{n1}$ is one selected from Formulae 3-1to 3-4:

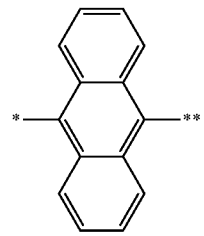

3-1

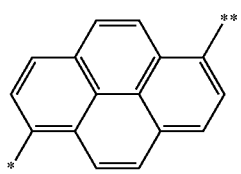

3-2

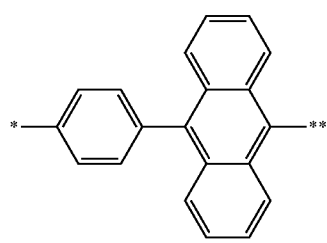

3-3

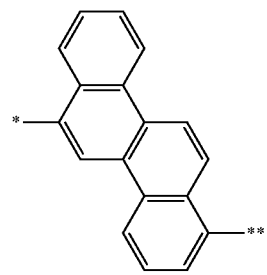

3-4 wherein, in Formulae 3-1to 3-4,

\* is a binding site with $R_4$, and

\*\* is a binding site with an indenopyridine ring portion of Formulae 1b to 1e;

$R_1$ and $R_2$ are a phenyl group, or $R_1$ and $R_2$ combined are Formula 5:

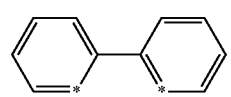

<Formula 5> wherein, in Formula 5,

\* is a binding site with an indenopyridine ring;

$R_{13}$ is selected from a hydrogen atom, a deuterium atom, a fluorine atom, a cyano group, a nitro group, and a methyl group;

$R_4$ is selected from a phenyl group, a 1-naphthyl group, and a 2-naphthyl group; and a2 is an integer of 0 or 1.

13. The indenopyridine-based compound as claimed in claim 1, wherein the indenopyridine-based compound represented by Formula 1 is one selected from Compounds 1, 3, 5, 7 to 9, 11 to 13, 15, 16, and 20 to 25:

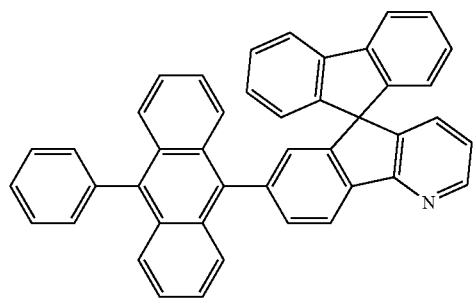
1
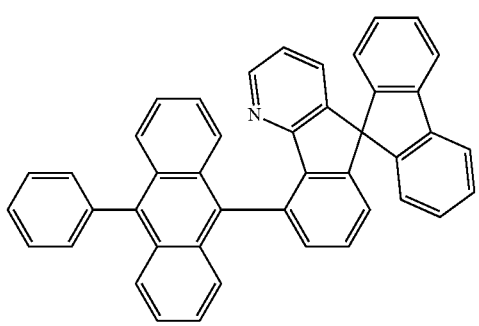
3
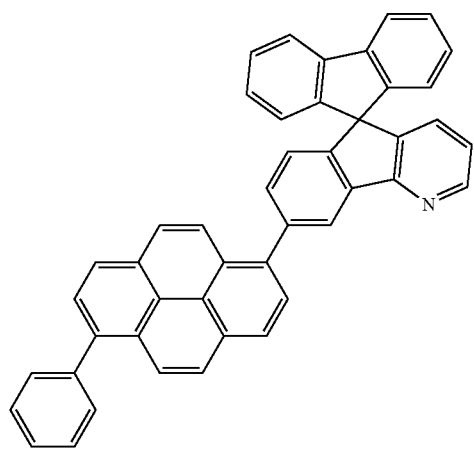
5
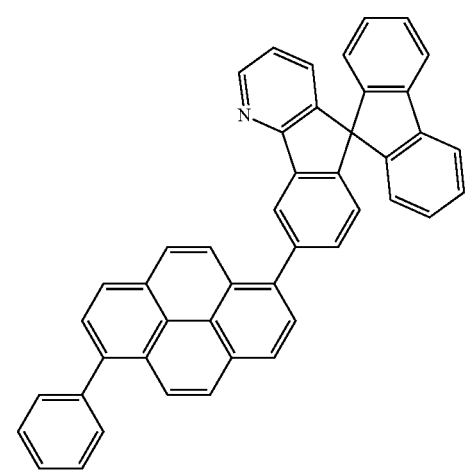
7
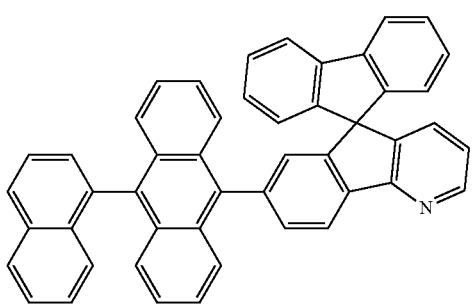
8
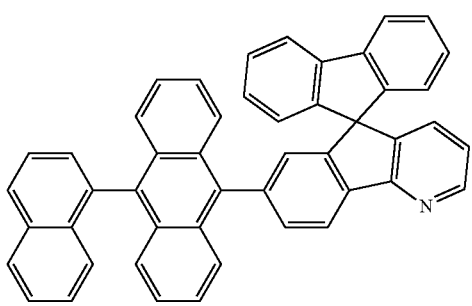
9
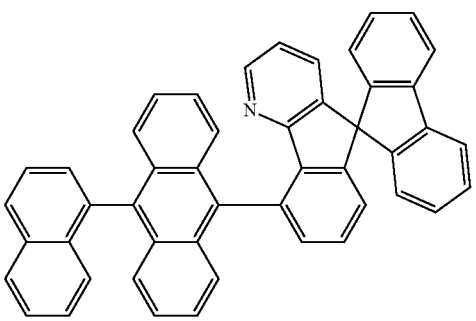
11
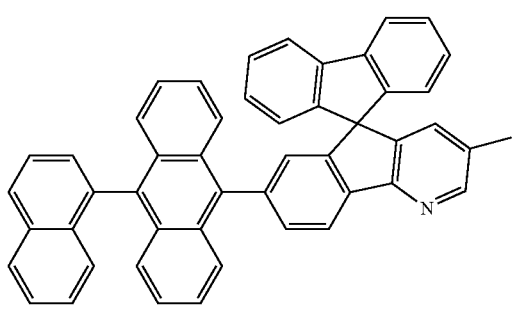
12

13
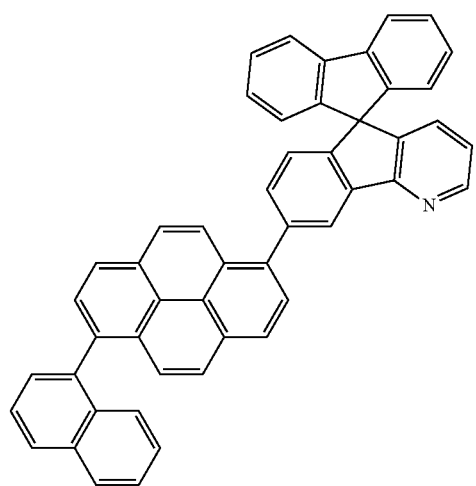
15
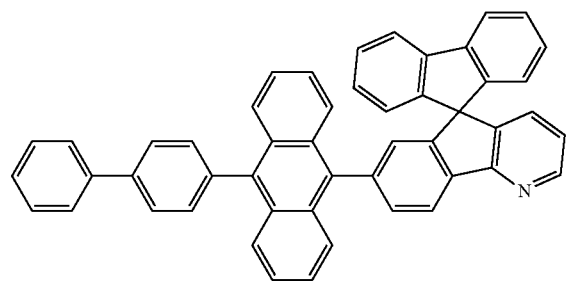
16
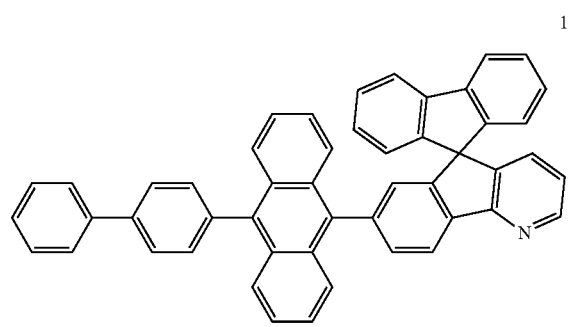
20
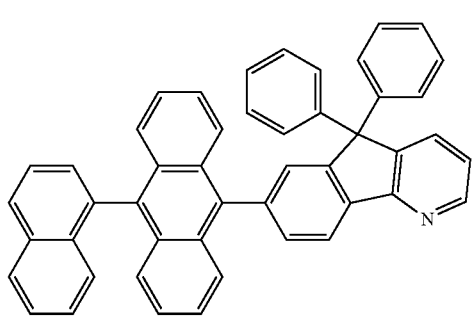
21
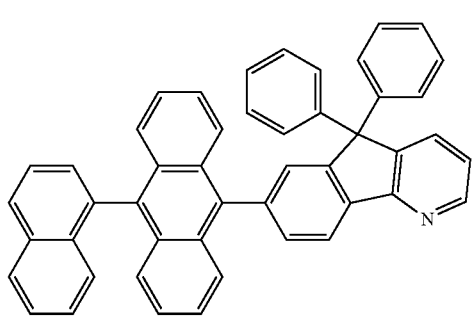
22
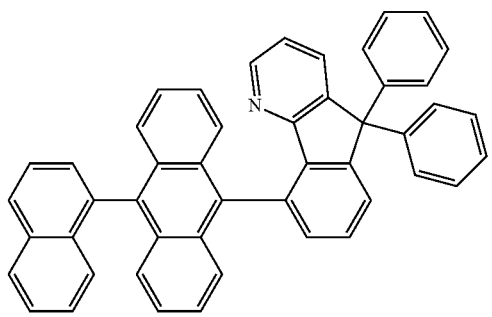
23
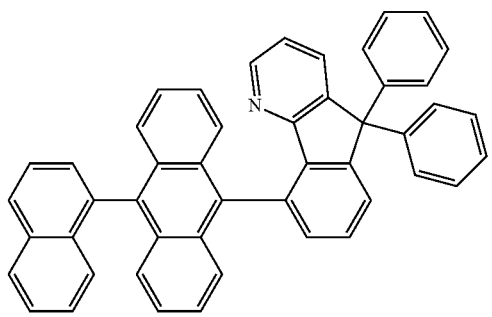
24
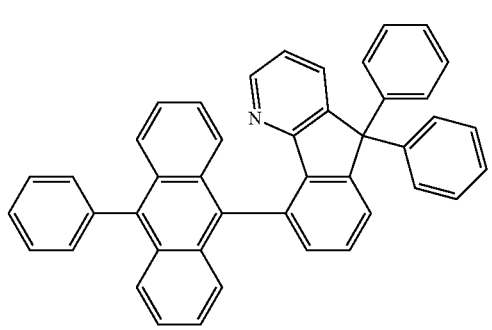

14. An organic light-emitting device (OLED), comprising:
   a first electrode;
   a second electrode facing the first electrode; and
   an organic layer that is disposed between the first electrode and the second electrode and includes an emission layer,
   wherein the organic layer includes at least one indenopyridine-based compound of claim 1.

15. The OLED as claimed in claim 14, wherein the organic layer further includes a hole transporting region including at least one selected from a hole injection layer, a hole transport layer, a functional layer having both hole injecting and transporting capabilities, a buffer layer, and an electron blocking layer between the first electrode and the emission layer, and further includes an electron transporting region including at least one selected from a hole blocking layer, an electron transport layer, and an electron injection layer between the emission layer and the second electrode.

16. The OLED as claimed in claim 14, wherein the emission layer includes the indenopyridine-based compound.

17. The OLED as claimed in claim 16, wherein the emission layer further includes a dopant, and the indenopyridine-based compound serves as a host.

18. The OLED as claimed in claim 17, wherein the dopant is an amine-based compound represented by Formula 100:

<Formula 100>

$$X \mathord{-} \left( N \begin{matrix} Ar_{101} \\ Ar_{102} \end{matrix} \right)_n$$

wherein, in Formula 100,
X is selected from an anthracenyl group, a chrysenyl group, a pyrenyl group, and a benzopyrenyl group;
$Ar_{101}$ and $Ar_{102}$ are each independently selected from
i) a phenyl group, a naphthyl group, and a biphenyl group; and
ii) a phenyl group, a naphthyl group, and a biphenyl group, each substituted with at least one of a deuterium atom, a fluorine atom, a cyano group, a nitro group, a methyl group, an ethyl group, an n-propyl group, an iso-propyl group, an n-butyl group, a sec-butyl group, an iso-butyl group, a tert-butyl group, and a phenyl group; and
n is an integer of 2 to 4.

19. The OLED as claimed in claim 17, wherein the dopant is one selected from Compounds 101 to 109:

106
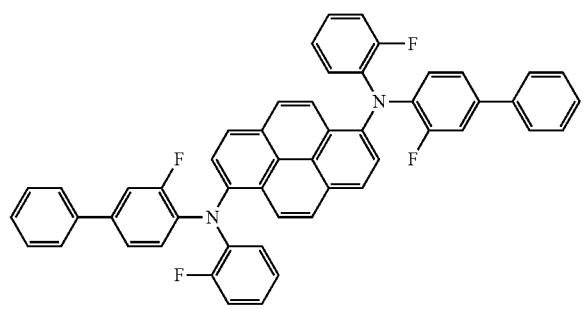
108
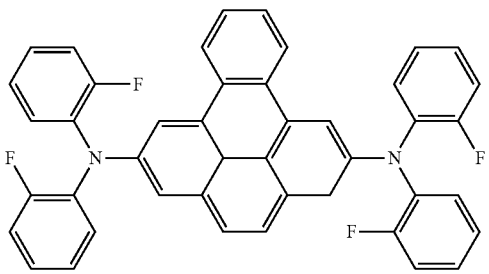
109
107
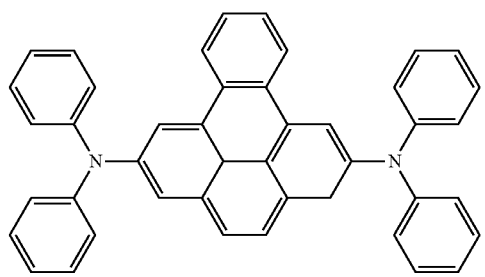
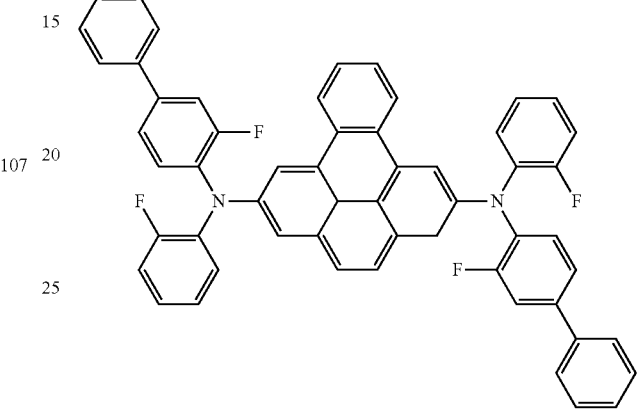
* * * * *